US011857800B1

(12) United States Patent
Cassano et al.

(10) Patent No.: US 11,857,800 B1
(45) Date of Patent: *Jan. 2, 2024

(54) PHOTOBIOMODULATION THERAPY GARMENT, METHODS AND USES

(71) Applicant: Niraxx Light Therapeutics, Inc., Irvine, CA (US)

(72) Inventors: Paolo Cassano, Lexington, MA (US); Joshua Chen, Newport Beach, CA (US)

(73) Assignee: Niraxx, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/906,713

(22) PCT Filed: Apr. 8, 2022

(86) PCT No.: PCT/US2022/071626
§ 371 (c)(1),
(2) Date: Oct. 13, 2022

(87) PCT Pub. No.: WO2022/217271
PCT Pub. Date: Oct. 13, 2022

Related U.S. Application Data

(60) Provisional application No. 63/272,363, filed on Oct. 27, 2021, provisional application No. 63/172,405, filed on Apr. 8, 2021.

(51) Int. Cl.
*A61N 5/06* (2006.01)

(52) U.S. Cl.
CPC ........ *A61N 5/06* (2013.01); *A61N 2005/0627* (2013.01); *A61N 2005/0648* (2013.01);
(Continued)

(58) Field of Classification Search
CPC .... A61N 2005/0627; A61N 2005/0648; A61N 2005/0652; A61N 2005/0659; A61N 5/06–2005/073
See application file for complete search history.

(56) References Cited

U.S. PATENT DOCUMENTS 6,443,978 B1  9/2002  Zharov
6,811,563 B2  11/2004 Savage et al.
(Continued)

FOREIGN PATENT DOCUMENTS

BR  PI1103710-5 A2  8/2013
BR  202013031418-3 U2  10/2015
(Continued)

OTHER PUBLICATIONS

Caldieraro, et al., Long-Term Near-Infrared Photobiomodulation for Anxious Depression Complicated by Takotsubo Cardiomyopathy, J. Clin. Psychopharm. 38(3): 268-269 (2018).
(Continued)

*Primary Examiner* — Jonathan T Kuo
(74) *Attorney, Agent, or Firm* — UltimatEdge IP Law Group, P.C.; Dean G. Stathakis

(57) ABSTRACT

The present specification discloses a photobiomodulation therapy garment having a garment structure configured to be worn by a user atop a skin surface with one or more near-infrared light sources integrated with the garment structure. The near-infrared light source is configured to emit near-infrared light directed to one or more regions of interest of the skin at a wavelength between 600 nm to 1600 nm and at a predetermined dosimetry and duration. A controller with a processor and memory is in communication with the near-infrared light source to control the operational parameters of the near-infrared light source.

20 Claims, 14 Drawing Sheets

(52) U.S. Cl.
CPC ............... *A61N 2005/0652* (2013.01); *A61N 2005/0659* (2013.01)

(56) References Cited

U.S. PATENT DOCUMENTS

| | | | |
|---|---|---|---|
| 6,974,224 | B2 | 12/2005 | Thomas-Benedict |
| 7,081,128 | B2 | 7/2006 | Hart et al. |
| 7,100,615 | B1 | 9/2006 | Kert |
| 7,101,384 | B2 | 9/2006 | Benedict |
| 7,128,442 | B2 | 10/2006 | Lee et al. |
| 7,303,578 | B2 | 12/2007 | De et al. |
| 7,304,201 | B2 | 12/2007 | Holloway et al. |
| 7,305,163 | B2 | 12/2007 | Williams |
| 7,309,348 | B2 | 12/2007 | Streeter et al. |
| 7,534,255 | B1 | 5/2009 | Streeter et al. |
| 7,575,589 | B2 | 8/2009 | De et al. |
| 7,686,839 | B2 | 3/2010 | Parker |
| 8,025,687 | B2 | 9/2011 | Streeter et al. |
| 8,165,684 | B2 | 4/2012 | Putz et al. |
| 8,167,921 | B2 | 5/2012 | Streeter et al. |
| 8,226,259 | B2 | 7/2012 | Van Pieterson et al. |
| 8,308,784 | B2 | 11/2012 | Streeter et al. |
| 8,374,696 | B2 | 2/2013 | Sanchez et al. |
| 8,430,919 | B2 | 4/2013 | Bornstein |
| 8,556,951 | B2 | 10/2013 | Witt et al. |
| 8,560,035 | B2 * | 10/2013 | Gonopolskiy ..... A61B 5/14552 600/323 |
| 8,702,291 | B2 | 4/2014 | Stephan |
| 8,852,254 | B2 | 10/2014 | Moscovici |
| 9,352,170 | B1 | 5/2016 | Davis |
| 9,440,092 | B2 | 9/2016 | Tapper et al. |
| 9,687,669 | B2 | 6/2017 | Stephan |
| 9,795,803 | B2 | 10/2017 | Streeter et al. |
| 9,814,426 | B2 | 11/2017 | Connor |
| 9,889,271 | B2 | 2/2018 | Adamczyk et al. |
| 9,895,077 | B2 | 2/2018 | Shahaf et al. |
| 9,993,659 | B2 | 6/2018 | Streeter et al. |
| 10,071,259 | B2 | 9/2018 | Delapp et al. |
| 10,188,872 | B2 | 1/2019 | De Taboada et al. |
| 10,272,259 | B1 | 4/2019 | Blanche |
| 10,315,042 | B2 | 6/2019 | De Taboada et al. |
| 10,357,662 | B2 | 7/2019 | De Taboada et al. |
| 10,653,889 | B2 | 5/2020 | De Taboada et al. |
| 10,683,494 | B2 | 6/2020 | Streeter et al. |
| 10,695,577 | B2 | 6/2020 | De Taboada et al. |
| 10,695,579 | B2 | 6/2020 | De Taboada et al. |
| 10,758,743 | B2 | 9/2020 | De Taboada et al. |
| 10,780,296 | B2 | 9/2020 | Zivin et al. |
| 10,857,376 | B2 | 12/2020 | De Taboada et al. |
| 10,913,943 | B2 | 2/2021 | Streeter et al. |
| 11,179,572 | B2 | 11/2021 | Taboada et al. |
| 11,219,782 | B2 | 1/2022 | Taboada et al. |
| 11,273,319 | B2 | 3/2022 | De Taboada et al. |
| 11,344,745 | B2 | 5/2022 | Nuytkens et al. |
| 11,577,094 | B2 | 2/2023 | Cassano |
| 2002/0188334 | A1 | 12/2002 | Carlgren |
| 2003/0181961 | A1 | 9/2003 | Kamei |
| 2004/0153131 | A1 | 8/2004 | Yorke |
| 2005/0024853 | A1 | 2/2005 | Thomas-Benedict |
| 2005/0177093 | A1 | 8/2005 | Barry et al. |
| 2006/0161226 | A1 | 7/2006 | McMickle |
| 2006/0167531 | A1 | 7/2006 | Gertner et al. |
| 2007/0150027 | A1 | 6/2007 | Rogers |
| 2007/0208395 | A1 | 9/2007 | Leclerc et al. |
| 2008/0077199 | A1 | 3/2008 | Shefi et al. |
| 2008/0319516 | A1 | 12/2008 | Dougal |
| 2009/0012586 | A1 | 1/2009 | Kepecs |
| 2009/0157141 | A1 | 6/2009 | Chiao et al. |
| 2010/0179469 | A1 | 7/2010 | Hammond et al. |
| 2010/0234927 | A1 | 9/2010 | Lin |
| 2011/0015707 | A1 | 1/2011 | Tucker et al. |
| 2011/0046463 | A1 * | 2/2011 | Gonopolskiy ..... A61B 5/14551 600/323 |
| 2011/0125230 | A1 | 5/2011 | Friedman et al. |
| 2011/0076529 | A1 | 6/2011 | Tucker et al. |
| 2011/0160814 | A2 | 6/2011 | Tucker et al. |
| 2012/0046716 | A1 | 2/2012 | Dougal |
| 2012/0289869 | A1 | 11/2012 | Tyler |
| 2013/0041432 | A1 | 2/2013 | Tucker et al. |
| 2013/0090520 | A1 | 4/2013 | Redfield et al. |
| 2013/0138182 | A1 | 5/2013 | Nissila et al. |
| 2014/0074010 | A1 | 3/2014 | Veres et al. |
| 2015/0165228 | A1 | 6/2015 | Lemmens et al. |
| 2015/0313496 | A1 | 11/2015 | Conner |
| 2015/0374971 | A1 | 12/2015 | Dar et al. |
| 2016/0045763 | A1 | 2/2016 | Tapper et al. |
| 2016/0106950 | A1 | 4/2016 | Vasapollo |
| 2016/0129279 | A1 | 5/2016 | Ferolito |
| 2016/0367834 | A1 | 12/2016 | Sauer |
| 2017/0333727 | A1 | 11/2017 | Kim et al. |
| 2018/0221682 | A1 | 8/2018 | Pepitone et al. |
| 2019/0060662 | A1 | 2/2019 | Pina |
| 2019/0083809 | A1 | 3/2019 | Zhang |
| 2019/0143114 | A1 | 5/2019 | Nelson |
| 2019/0299021 | A1 | 10/2019 | Kamei |
| 2020/0086138 | A1 | 3/2020 | Cassano |
| 2020/0253813 | A1 | 8/2020 | Kuhns |
| 2020/0330786 | A1 | 10/2020 | De Taboada et al. |
| 2020/0360715 | A1 | 11/2020 | Lim |
| 2021/0205634 | A1 | 7/2021 | Sverdlov et al. |
| 2022/0387818 | A1 | 12/2022 | Sverdlov et al. |

FOREIGN PATENT DOCUMENTS

| | | |
|---|---|---|
| WO | 2008029001 A1 | 3/2008 |
| WO | 2008144157 A1 | 11/2008 |
| WO | 2012130958 A1 | 10/2012 |
| WO | 2013036558 A1 | 3/2013 |
| WO | 2015069627 A1 | 5/2015 |
| WO | 2017013051 A1 | 1/2017 |
| WO | 2017019839 A1 | 2/2017 |
| WO | 2018018019 A1 | 1/2018 |
| WO | 2018051354 A1 | 3/2018 |
| WO | 2018191137 A1 | 10/2018 |
| WO | 2019053625 A1 | 3/2019 |
| WO | 2021076756 A1 | 4/2021 |
| WO | 2022197937 A1 | 9/2022 |

OTHER PUBLICATIONS

Caldieraro, et al., Transcranial Photobiomodulation for Major Depressive and Axiety Disorders and for Posttraumatic Stress Disorder, Chp. 35, pp. 479-487, in Photobiomodulation in the Brain, Hamblin & Huang, eds. (2019).

Caldieraro, et al., Photobiomodulation, Chp. 18., pp. 233-246, in The Massachusetts General Hospital Guide to Depression, Shapero, et al., eds. (2019).

Cassano, et al., Near-Infrared Transcranial Radiation for Major Depressive Disorder: Proof of Concept Study, Psychiatry J. 352979: 1-8 (2015).

Cassano, Photomedicine and Pharmaceuticals: A Brain New Deal, Photobiomodul. Photomed. Laser Surg. 37(10): 575-576 (2019).

Cassano, et al., Reported Side Effects, Weight and Blood Pressure, After Repeated Sessions of Transcranial Photobiomodulation, Photobiomodul. Photomed. Laser Surg. 37(10): 651-656 (2019).

Hamblin, et al., Photobiomodulation in the Brain, pp. 659, Hamblin & Huang, eds. (2019).

Mannu, et al., Transcranial Photobiomodulation for Fibromyalgia, Clin. Case Rep. J. 1(3): 1-2 (2020).

Mannu, et al., Transcranial Photobiomodulation to Augment Lithium in Bipolar-I Disorder, Photobiomodul. Photomed. Laser Surg. 37(10): 577-578 (2019).

Mannu, et al., Transcranial Photobiomodulation for Down Syndrome, Photobiomodul. Photomed. Laser Surg. 37(10): 579-580 (2019).

Morries, et al., Treatments for Traumatic Brain Injury with Emphasis on Transcranial Near-Infrared Laser Phototherapy, Neuropsychiatric Dis. Treat. 11: 2159-2175 (2015).

Salehpour, et al., A Protocol for Transcranial Photobiomodulation Therapy in Mice, J. Visual. Exp. 141(e59076): 1-8 (2018).

(56) References Cited

OTHER PUBLICATIONS

Salehpour, et al., Photobiomodulation for Depression in Animal Models, Chp. 14, pp. 189-205, in Photobiomodulation in the Brain, Hamblin & Huang, eds. (2019).
Salehpour, et al., Penetration Profiles of Visible and Near-Infrared Lasers and Light-Emitting Diode Light Through the Head Tissues in Animal and Human Species: A Review of Literature, Photobiomodul. Photomed. Laser Surg. 37(10): 581-595 (2019).
WIPO, PCT Form ISA210, International Search Report for International Patent Application Serial No. PCT/US2023/065563, pp. 3 (dated Aug. 16, 2023).
WIPO, PCT Form ISA237, Written Opinion for International Patent Application Serial No. PCT/US2023/065563, pp. 6 (dated Aug. 16, 2023).
Askalsky, et al., Transcranial Photobiomodulation For The Management Of Depression: Current Perspectives, Neuropsychiatric Disease and Treatment, vol. 15, pp. 18 (2019).
Cassano, et al., Effects of Transcranial Photobiomodulation with Near-Infrared Light on Sexual Dysfunction, Lasers Surg Med. 51(2): 127-135. (2019).
Cassano, et al., Review of transcranial photobiomodulation for major depressive disorder: targeting brain metabolism, inflammation, oxidative stress, and neurogenesis, Neurophotonics 3(3), 031404 (2016).
Cassano, et al., Selective photobiomodulation for emotion regulation: model-based dosimetry study, Neurophotonics 6(1), 015004 (2019).
Cassano, et al., Transcranial Photobiomodulation for the Treatment of Major Depressive Disorder. The ELATED-2 Pilot Trial, Photomedicine and Laser Surgery: vol. 36, 12, pp. 634-646 (2018).
Gabel, et al., A case control series for the effect of photobiomodulation in patients with low back pain and concurrent depression, Laser Therapy 27.3: 167-173 (2018).
Maiello, et al., Transcranial Photobiomodulation with Near-Infrared Light for Generalized Anxiety Disorder: A Pilot Study, Photobiomodulation, Photomedicine, and Laser Surgery vol. 37, pp. 644-650 (2019).
Salehpour, et al., Near-Infrared Photobiomodulation Combined with Coenzyme Q10 for Depression in a Mouse Model of Restraint Stress: Reduction in Oxidative Stress, Neuroinflammation, and Apoptosis.
Salehpour, et al., Therapeutic potential of intranasal photobiomodulation therapy for neurological and neuropsychiatric disorders: a narrative review, Rev Neurosci; 31(3): 269-286. (2020).
Salehpour, et al., Transcranial Photobiomodulation Improves Cognitive Performance in Young Healthy Adults: A Systematic Review and Meta-Analysis, Photobiomodulation, Photomedicine, and Laser Surgery vol. 37, pp. 635-643 (2019).
WIPO, PCT Form ISA210, International Search Report for PCT/US2022/071626, pp. 5 (dated Jun. 15, 2022).
WIPO, PCT Form ISA237, Written Opinion for International Patent Application Serial No. PCT/US2022/071626, pp. 10 (dated Jun. 15, 2022).
Yuan, Transcranial photobiomodulation with near-infrared light from childhood to elderliness: simulation of dosimetry, Neurophoton. 7(1), 015009 (2020).
U.S. Appl. No. 17/658,597, filed Apr. 8, 2022.

\* cited by examiner

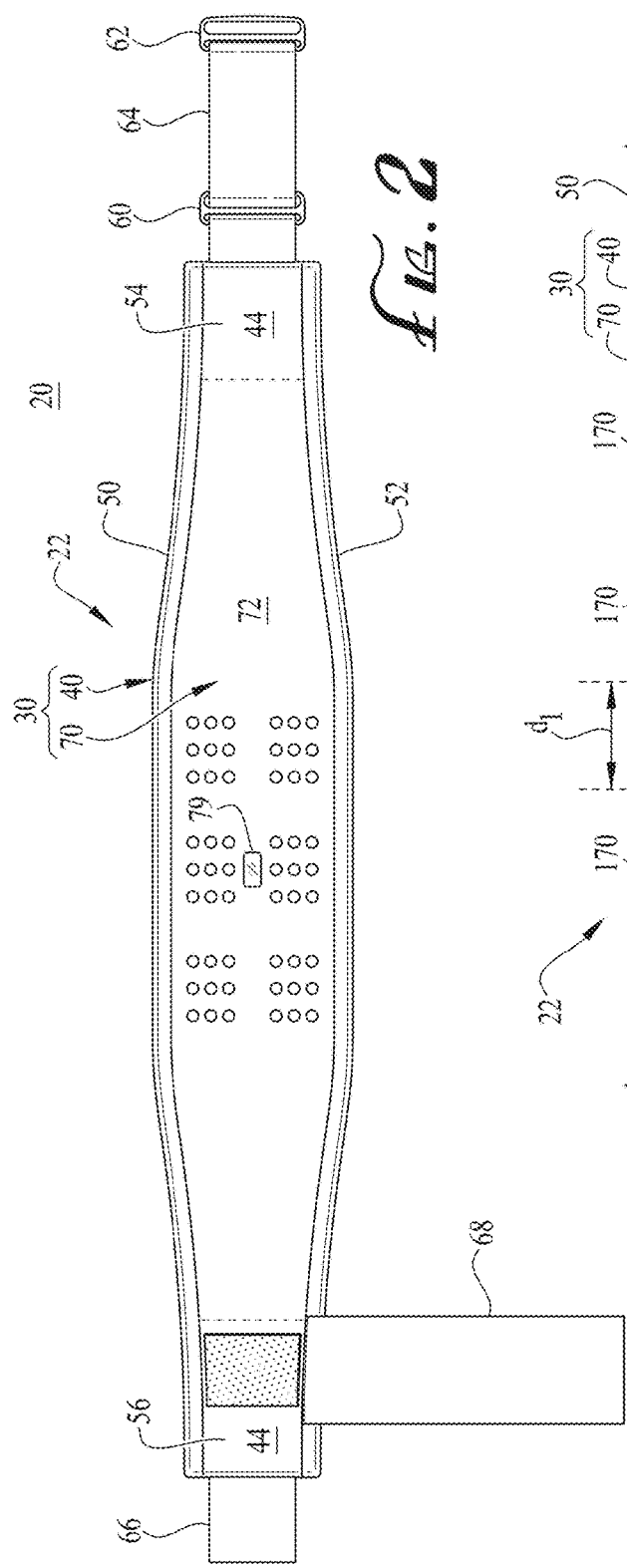
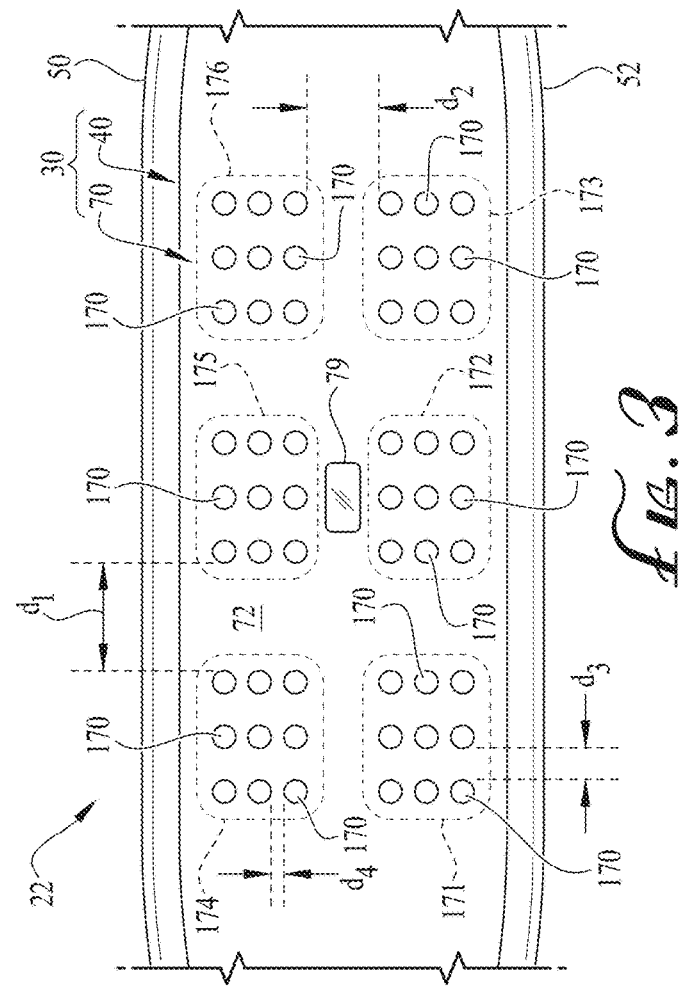

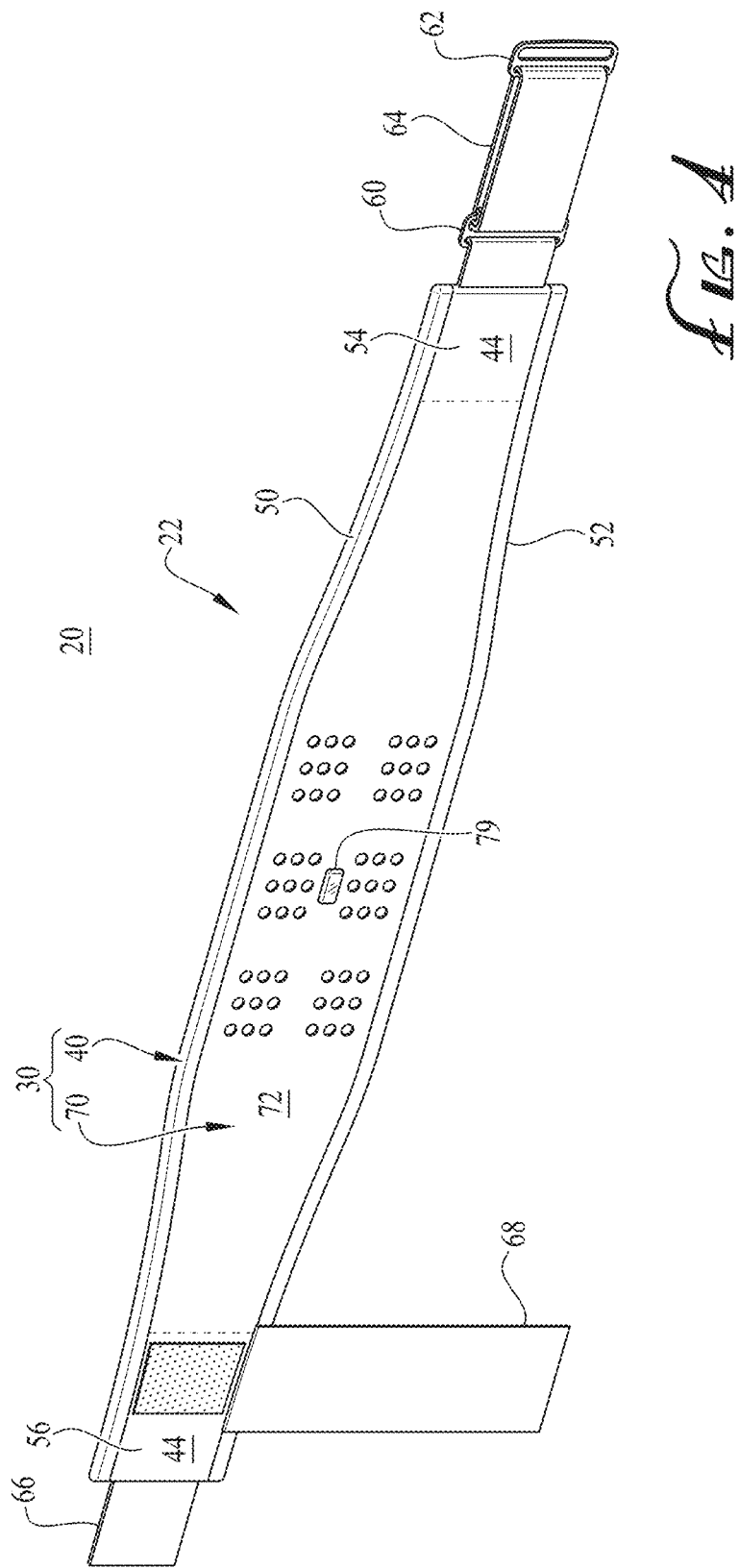

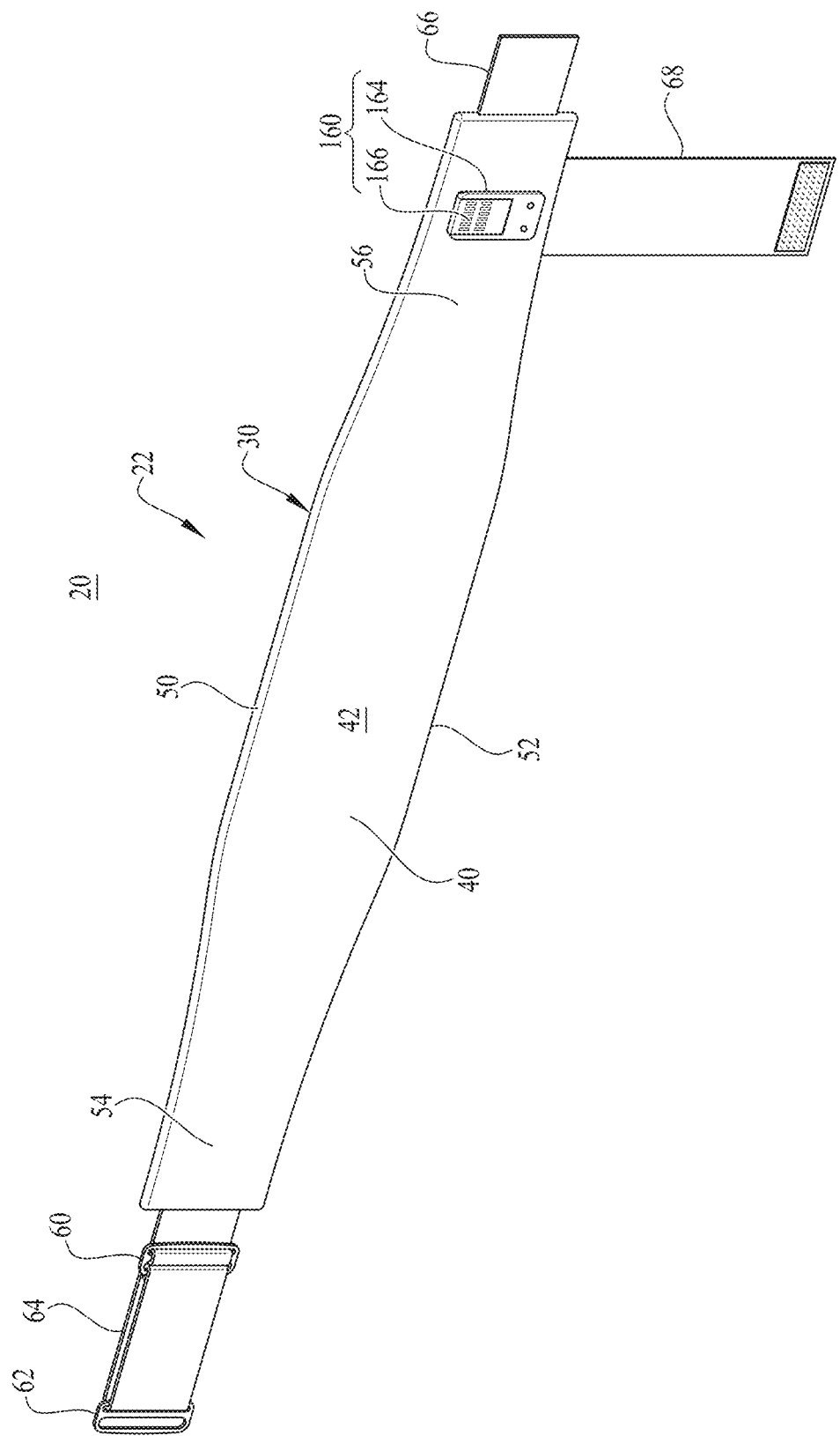

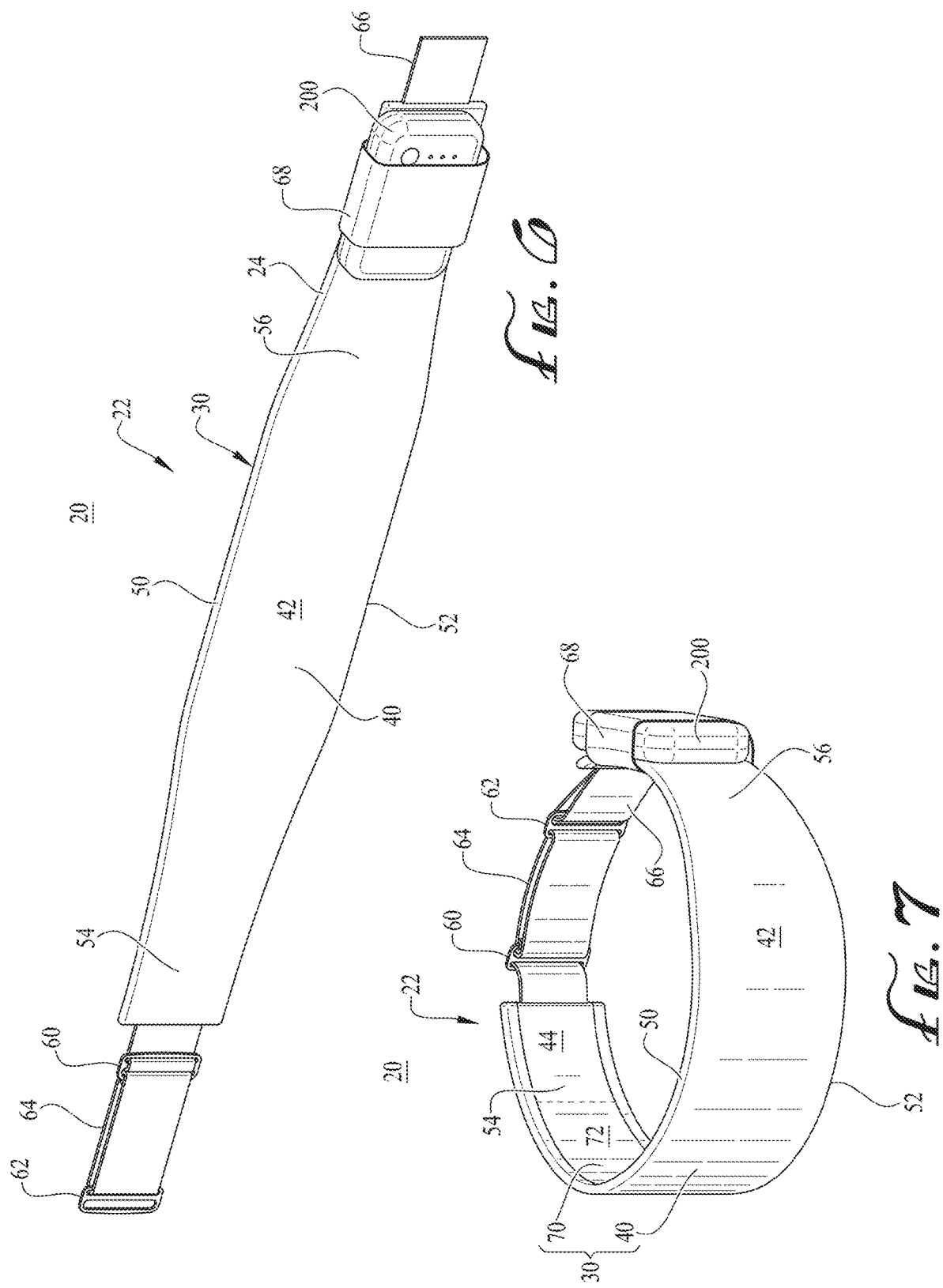

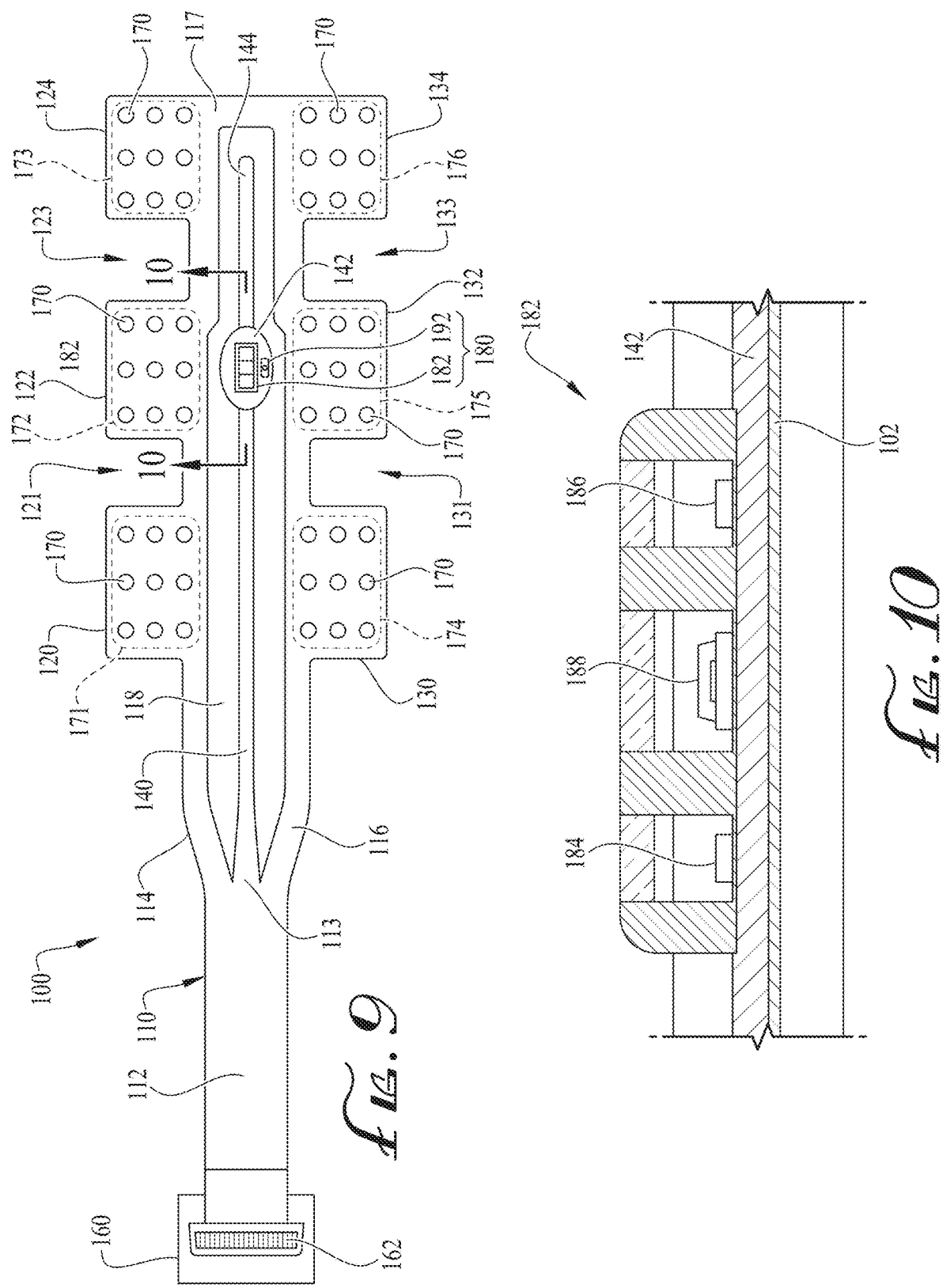

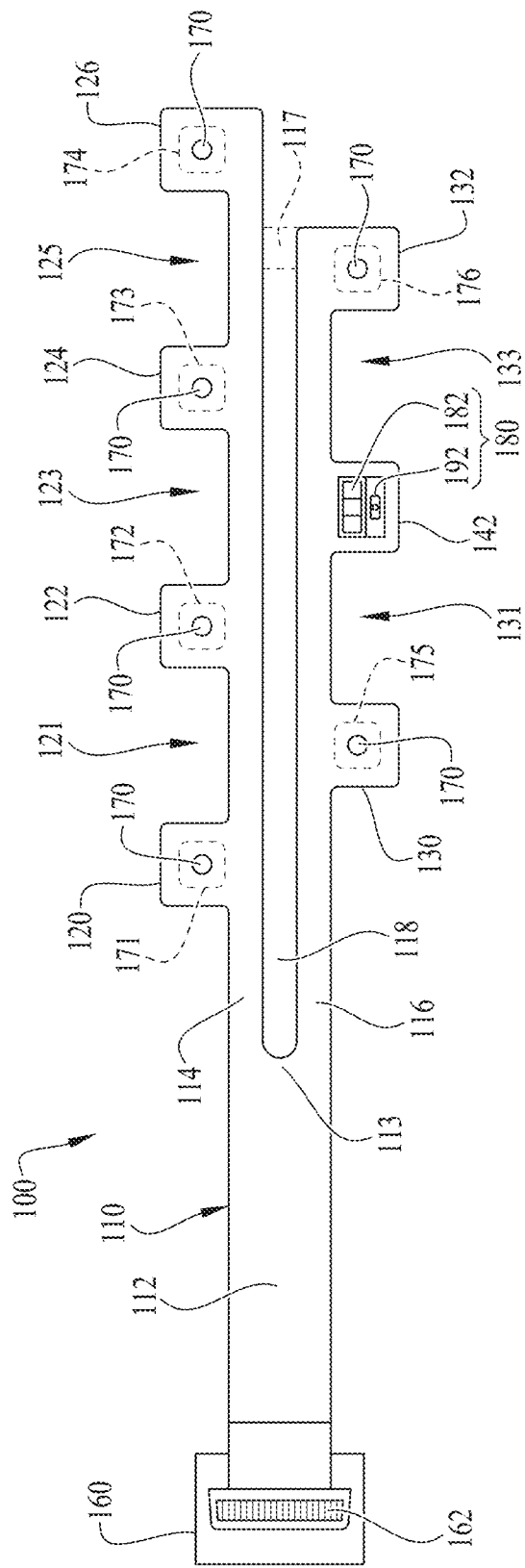

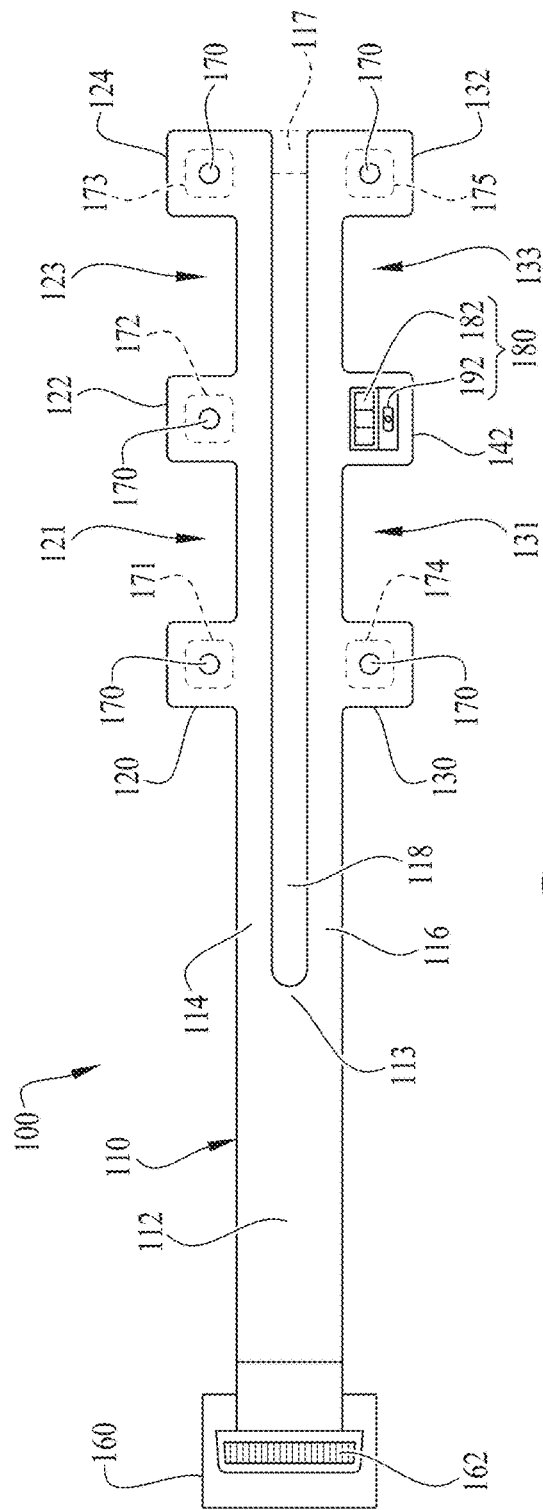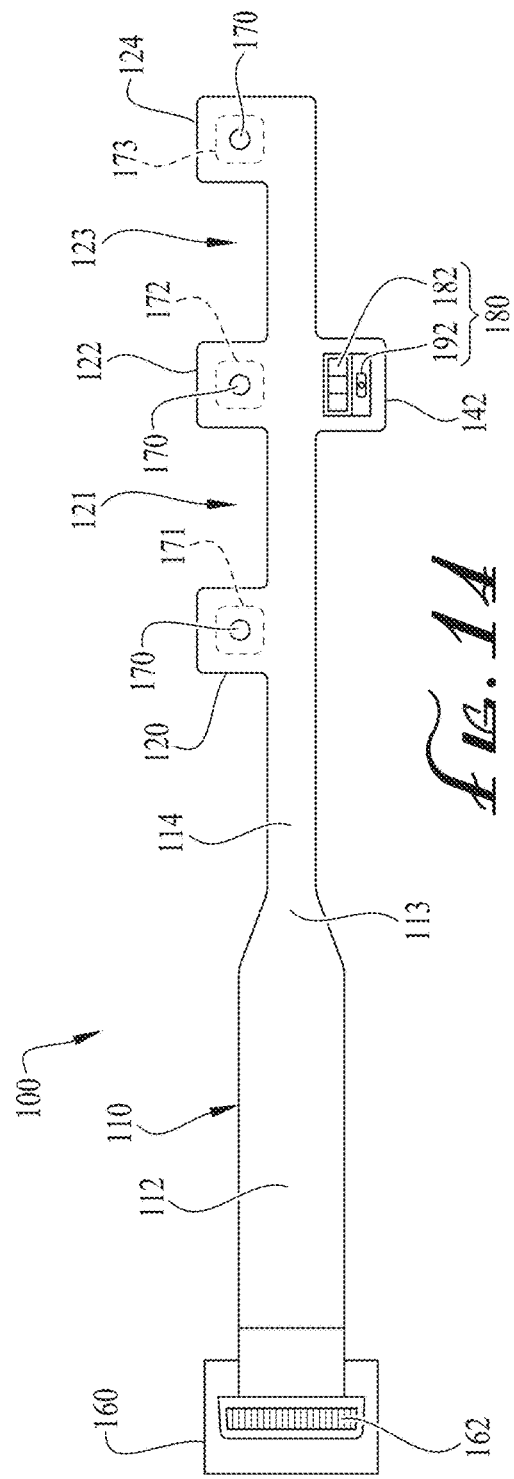

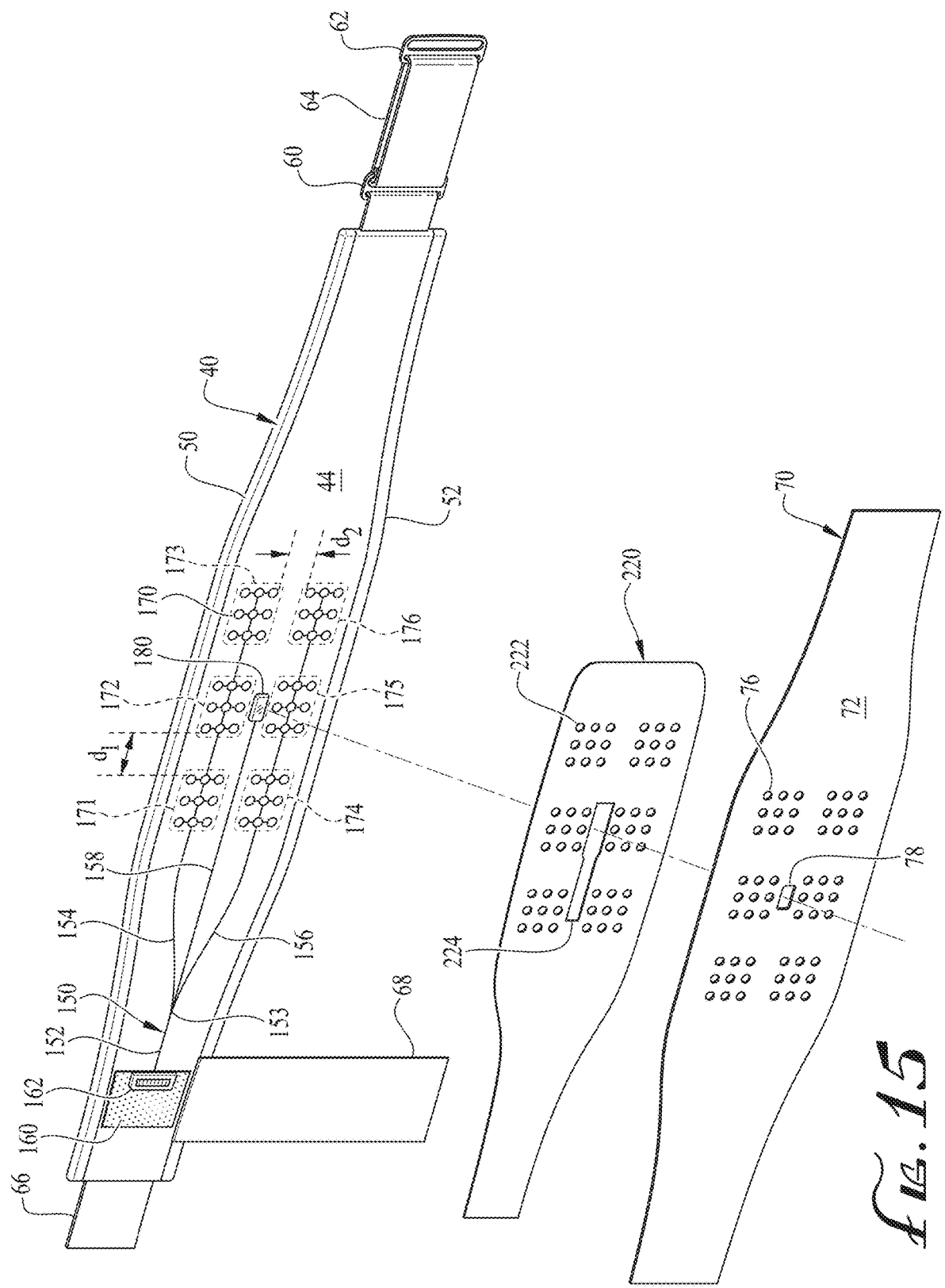

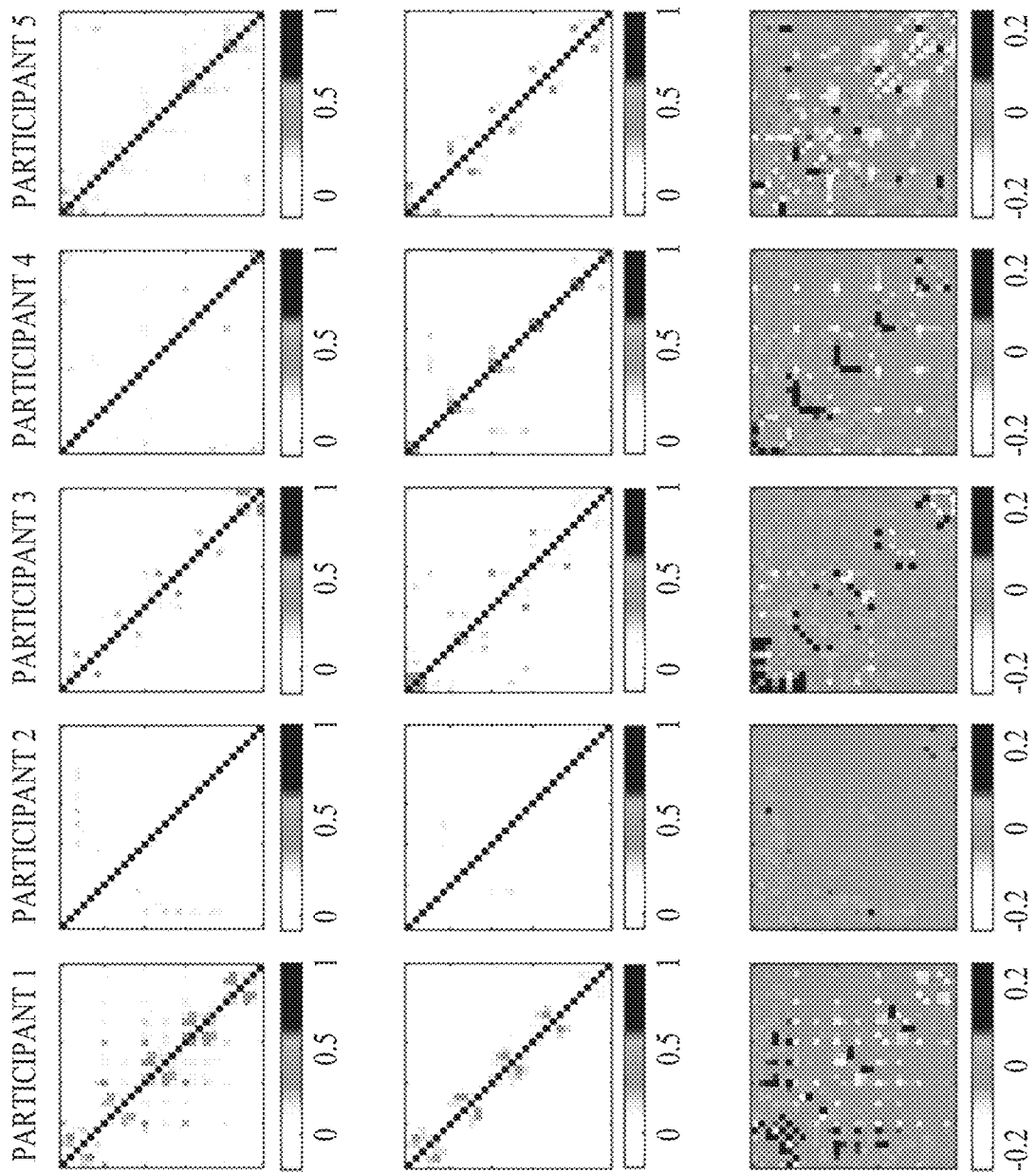

PHOTOBIOMODULATION THERAPY GARMENT, METHODS AND USES

BACKGROUND

This application is a 35 U.S.C. § 371 U.S. national stage patent application which claims the benefit of priority and is entitled to the filing date of International Patent Application PCT/US2022/071626, filed Apr. 8, 2022, an international patent application which claims the benefit of priority and is entitled to the filing date pursuant to 35 U.S.C. § 119(e) of U.S. Provisional Patent Application 63/272,363, filed Oct. 27, 2021 and U.S. Provisional Patent Application 63/172,405, filed Apr. 8, 2021, the content of each of which is hereby incorporated by reference in its entirety. by reference in its entirety.

The subject of this patent application relates generally to devices and methods for treating disorders using photobiomodulation therapy with near-infrared light.

By way of background, photobiomodulation therapy is the application of near-infrared light directed to various portions of a subject's body, for example, to the skin. Photobiomodulation therapy induces a photochemical reaction in the cells, increasing mitochondrial activity and ATP levels. The near-infrared light is calibrated to penetrate through the skin, soft tissue, cartilage, cerebrospinal fluid, and through bone structure for the purpose of providing treatment for various disorders. In an example transcranial photobiomodulation treatment, a near-infrared light source is directed to the head, such that the near-infrared light penetrates the skull to apply the light to the brain, for treating mental health related conditions like stress, fatigue, ADHD, other psychiatric, neuropsychiatric, and neurodegenerative diseases, and so on.

During treatment, one or more light source must be held in position on the user's skin for a prolonged period of time. However, the user may wish to continue with daily activities during the treatment period, requiring a portable system that remains in place during sedentary and vigorous activities, so that treatment is delivered accurately and without disturbance. Furthermore, a portable system would allow from immediate, real-time use enabling the user to undergo a photobiomodulation therapy whenever needed.

Aspects of the present invention fulfill these needs and provide further related advantages as described in the following summary.

SUMMARY

Aspects of the present invention teach certain benefits in construction and use which give rise to the exemplary advantages described below.

The present specification discloses a photobiomodulation therapy garment having a garment configured to be donned by a user atop a skin surface with one or more near-infrared light sources integrated with the garment. The near-infrared light source is configured to emit near-infrared light directed to one or more regions of interest of the skin at a wavelength between about 700 nm to about 1600 nm and at a predetermined dosimetry and duration. A controller with a processor and memory is in communication near-infrared light source to control the operational parameters of the near-infrared light source.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings, which are incorporated in and constitute a part of this specification, illustrate aspects of the disclosed subject matter in at least one of its exemplary embodiments, which are further defined in detail in the following description. Features, elements, and aspects of the disclosure are referenced by numerals with like numerals in different drawings representing the same, equivalent, or similar features, elements, or aspects, in accordance with one or more embodiments. The drawings are not necessarily to scale, emphasis instead being placed upon illustrating the principles herein described and provided by exemplary embodiments of the invention. In such drawings:

FIG. 2 is a rear plan view of an exemplary photobiomodulation therapy garment in an open configuration;

FIG. 3 is a magnified rear plan view of the photobiomodulation therapy garment of FIG. 2, illustrating an exemplary intergroup and intragroup arrangement of near-infrared light sources;

FIG. 4 is a rear perspective view of the photobiomodulation therapy garment of FIG. 2;

FIG. 5 is a front perspective view of the photobiomodulation therapy garment of FIG. 2, illustrating the terminal rail with controller detached;

FIG. 6 is a front perspective view of the photobiomodulation therapy garment of FIG. 2, illustrating a controller disclosed herein fastened to the photobiomodulation therapy garment;

FIG. 7 is a front perspective view of the photobiomodulation therapy garment of FIG. 6 in a closed configuration, illustrating the adjustment strap closed to form a band;

FIG. 9 is a top plan view of a photobiomodulation unit disclosed herein comprising a flexible printed circuit board assembly;

FIG. 10 is a magnified cross-sectional view of photobiomodulation unit of FIG. 9, taken at 10-10, illustrating a sensor disclosed herein;

FIG. 12 is a top plan view of a photobiomodulation unit disclosed herein comprising a flexible printed circuit board assembly;

FIG. 13 is a top plan view of a photobiomodulation unit disclosed herein comprising a flexible printed circuit board assembly;

FIG. 14 is a top plan view of a photobiomodulation unit disclosed herein comprising a flexible printed circuit board assembly;

FIG. 15 is an exploded rear perspective view of the photobiomodulation therapy garment disclosed herein, illustrating a liquid wire circuit assembly.

FIGS. 17A-17C show EEG scans of five participants from a research study who underwent a transcranial photobiomodulation (tPBM) treatment using a photobiomodulation therapy garment disclosed herein with FIG. 17A showing an EEG scan of each participant before a tPBM treatment; FIG. 17B showing an EEG scan of each participant after a tPBM treatment; and FIG. 17C showing merged before and after EEG scans to highlight the difference; and FIGS. 18A-18B show graphs of data obtained from an EEG scan of a participant using a photobiomodulation therapy garment disclosed herein with FIG. 18A showing percent change of frequency during use of a photobiomodulation therapy garment disclosed herein; and FIG. 18B showing change in gamma power over time during use of a photobiomodulation therapy garment disclosed herein.

Figure 1:
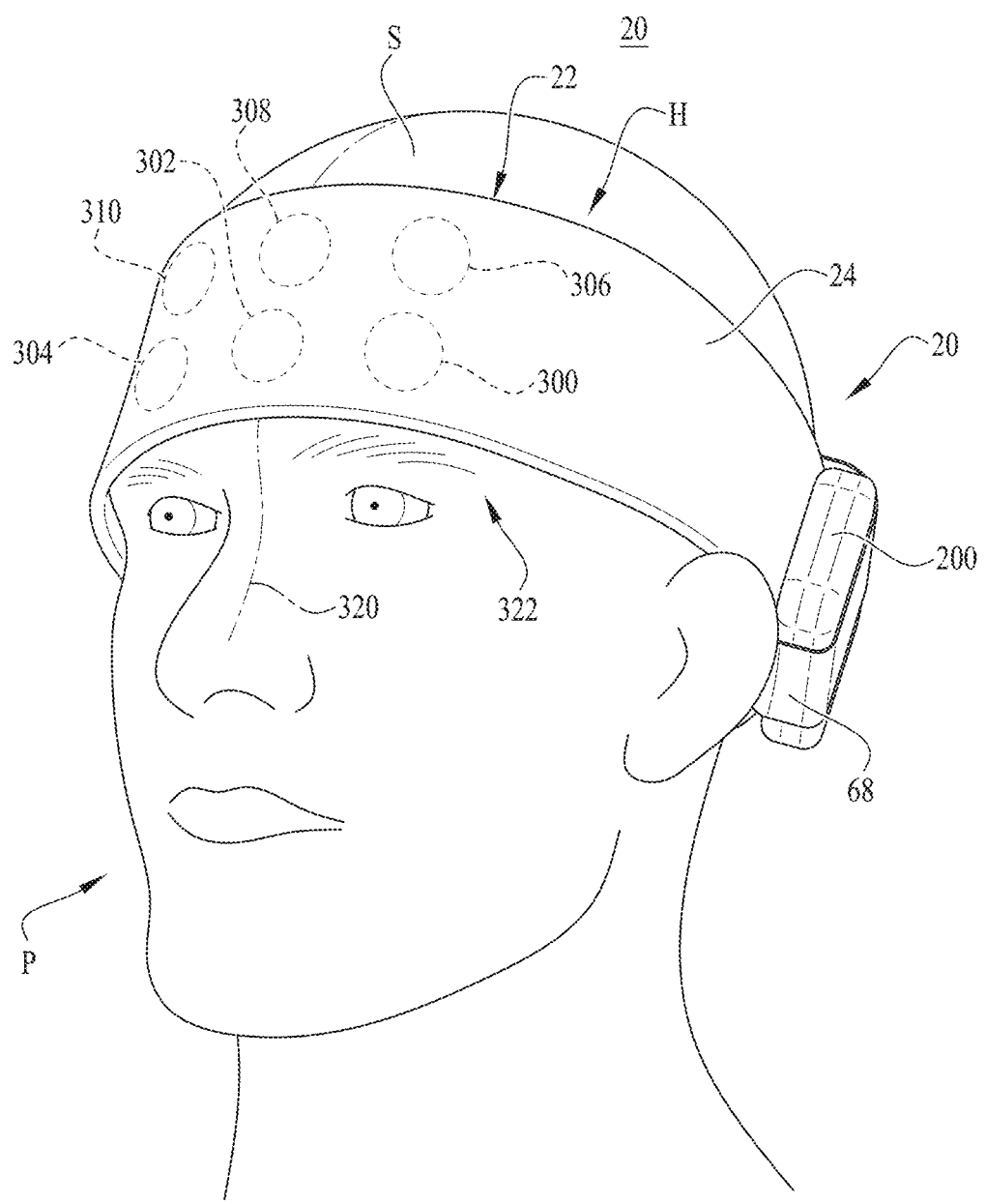
FIG. 1 is a front perspective view of an exemplary photobiomodulation therapy garment disclosed herein donned by a user.

| Listing of Reference Numbers Associated with Drawings | |
|---|---|
| Ref. No. | Element |
| P | Person |
| S | Skin surface |
| H | Head region |
| d1 | Column intergroup spacing |
| d2 | Row intergroup spacing |
| d3 | Column intragroup spacing |
| d4 | Row intragroup spacing |
| 20 | Photobiomodulation therapy garment |
| 22 | Photobiomodulation therapy headband |
| 30 | Garment of photobiomodulation therapy garment 20, 22 |
| 40 | Outer fabric sheet of garment 24 |
| 42 | Outside surface of outer fabric sheet 40 |
| 44 | Inside surface of outer fabric sheet 40 |
| 46 | Therapeutic portion of outer fabric sheet 40 |
| 50 | Top edge of garment 30 |
| 52 | Bottom edge of garment 30 |
| 54 | Right portion of garment 30 |
| 56 | Left portion of garment 30 |
| 58 | Terminal rail mount opening of garment 30 |
| 60 | Slide buckle of garment 30 |
| 62 | Slide buckle of garment 30 |
| 64 | Right head strap of garment 30 |
| 66 | Left head strap of garment 30 |
| 68 | Controller strap of garment 30 |
| 70 | Inner fabric sheet of garment 24 |
| 72 | Outside surface of inner fabric sheet 70 |
| 74 | Inside surface of inner fabric sheet 70 |
| 76 | Near-infrared light opening of inner fabric sheet 70 |
| 78 | Sensor opening of inner fabric sheet 70 |
| 79 | Sensor cover of inner fabric sheet 70 |
| 100 | Photobiomodulation unit of photobiomodulation therapy garment 20, 22 |
| 102 | Heat dissipating material of photobiomodulation 100 |
| 110 | Flexible printed circuit board assembly of photobiomodulation 100 |
| 112 | Main strip of flexible printed circuit board assembly 110 |
| 113 | Root of flexible printed circuit board assembly 110 |
| 114 | First strip of flexible printed circuit board assembly 110 |
| 116 | Second strip of flexible printed circuit board assembly 110 |
| 117 | Connecting portion of flexible printed circuit board assembly 110 |
| 118 | Sensor strip cutout of flexible printed circuit board assembly 110 |
| 120 | First mounting portion of first strip 114 |
| 121 | First cutout of first strip 114 |
| 122 | Second mounting portion of first strip 114 |
| 123 | Second cutout of first strip 114 |
| 124 | Third mounting portion of first strip 114 |
| 130 | First mounting portion of second strip 116 |
| 131 | First cutout of second strip 116 |
| 132 | Second mounting portion of second strip 116 |
| 133 | Second cutout of second strip 116 |
| 134 | Third mounting portion of second strip 116 |
| 140 | Sensor strip of flexible printed circuit board assembly 110 |
| 142 | Sensor mounting portion of sensor strip 140 |
| 144 | Sensor strip free end of sensor strip 140 |
| 150 | Liquid wire circuit assembly of photobiomodulation 100 |
| 152 | Main liquid wire tube of liquid wire circuit board assembly 150 |

-continued

| Listing of Reference Numbers Associated with Drawings | |
|---|---|
| Ref. No. | Element |
| 153 | Root of liquid wire circuit board assembly 150 |
| 154 | First liquid wire tube of liquid wire circuit board assembly 150 |
| 156 | Second liquid wire tube of liquid wire circuit board assembly 150 |
| 158 | Sensor liquid wire tube of liquid wire circuit board assembly 150 |
| 160 | Connection terminal of circuit board assembly 84 |
| 162 | Electronic circuity connector of connection terminal 160 |
| 164 | Terminal rail mount of connection terminal 160 |
| 166 | Contacts of terminal rail mount 164 |
| 170 | Near-infrared light source of photobiomodulation 100 |
| 171 | First near-infrared light source grouping of near-infrared light source 170 |
| 172 | Second near-infrared light source grouping of near-infrared light source 170 |
| 173 | Third near-infrared light source grouping of near-infrared light source 170 |
| 174 | Fourth near-infrared light source grouping of near-infrared light source 170 |
| 175 | Fifth near-infrared light source grouping of near-infrared light source 170 |
| 176 | Sixth near-infrared light source grouping of near-infrared light source 170 |
| 180 | Sensor of photobiomodulation unit 100 |
| 182 | Cardiovascular sensor of photobiomodulation 100 |
| 184 | Green LED of cardiovascular sensor 182 |
| 186 | Green LED of cardiovascular sensor 182 |
| 188 | Photodetector of cardiovascular sensor 182 or 114 |
| 192 | Temperature sensor of photobiomodulation 100 |
| 194 | Stimulator of photobiomodulation unit 100 |
| 200 | Controller of photobiomodulation therapy garment 20, 22 |
| 210 | Hot melt adhesive film of photobiomodulation therapy garment 20, 22 |
| 220 | Double-sided tape layer of photobiomodulation therapy garment 20, 22 |
| 222 | Near-infrared light source opening of double-sided tape layer 220 |
| 224 | Sensor opening of double-sided tape layer 220 |
| 300 | Fp1 site of person P |
| 302 | Fpz site of person P |
| 304 | Fp2 site of person P |
| 306 | F3 site of person P |
| 308 | Fz site of person P |
| 310 | F4 site of person P |
| 320 | Sagittal plane of person P |
| 322 | Superciliary arch region of person P |

DETAILED DESCRIPTION

The detailed descriptions set forth below in connection with the appended drawings are intended as a description of embodiments of the invention, and is not intended to represent the only forms in which the present invention may be constructed and/or utilized. The descriptions set forth the structure and the sequence of steps for constructing and operating the invention in connection with the illustrated embodiments. It is to be understood, however, that the same or equivalent structures and steps may be accomplished by different embodiments that are also intended to be encompassed within the spirit and scope of the invention.

The present system in one or more embodiments provides a photobiomodulation therapy garment. A photobiomodulation therapy garment disclosed herein comprising a garment configured to be donned by a user atop a skin surface which integrates one or more photobiomodulation units which in conjunction with a controller are configured to administer a photobiomodulation therapy. A photobiomodulation unit includes one or more near-infrared light sources, one or more sensors, and optionally one or more stimulators in electrical connection with a connection terminal. The connection terminal is also configured to operationally receive the controller in an manner that establishes an electrical connection. Each of the one or more near-infrared light sources disclosed herein is configured to emit near-infrared light at a wavelength between 600 nm to 1600 nm and at a predetermined dosimetry and duration. A controller disclosed herein has a processor and memory and is configured to control the operational parameters of the near-infrared light source. During operation, a photobiomodulation unit is configured to emit near-infrared light to one or more regions of a skin surface of a user. In some embodiments, and as shown in FIGS. 1-16, a photobiomodulation therapy garment 20 comprises a garment 30, a photobiomodulation unit 100, and a controller 200.

In some embodiments, and as shown in FIGS. 1-7, photobiomodulation therapy garment 20 can be configured as a photobiomodulation therapy headband 22 for the purpose of treating specific regions of a head H of a person P using a transcranial photobiomodulation therapy. In this configuration, person P dons photobiomodulation therapy headband 22 by wrapping snugly around head region H so that one or more near-infrared light sources disclosed herein integrated into photobiomodulation therapy headband 22 are positioned overtop and/or directed to a region of interest of skin surface S for delivering therapeutic levels of near-infrared light to a region of interest. In some embodiments, positioning of photobiomodulation therapy headband 22 as shown in FIG. 1, situates the one or more near-infrared light sources disclosed herein atop a frontal bone region of the skull of person P, approximately and/or substantially centered on midsagittal plane 320 (e.g., centered on the nose) for the purpose of administering near-infrared light for treating a disorder through the skull to a brain region of person P. Further, in these embodiments, photobiomodulation therapy headband 22 is positioned such that one the near-infrared light sources disclosed herein are approximately positioned above superciliary arch region 322 (i.e., the brown ridge above the eye sockets); and generally beneath the hairline (although the hairline varies somewhat depending on the individual). At minimum, in one or more embodiments, at least one the near-infrared light sources disclosed herein integrated within photobiomodulation therapy headband 22 should be positioned above superciliary arch region 322 or at minimum above the eye sockets, to minimize exposure of the eyes to the near-infrared light. In some embodiments, and as shown in FIG. 1, photobiomodulation therapy headband 22 is positioned to cover defined regions of interest on skin surface S comprising one or more or all of a Fp1 site 300, a Fpz site 302, a Fp2 site 304, a F3 site 306, a Fz site 308, and a F4 site 310, when photobiomodulation therapy headband 22 is donned on head H and properly positioned.

Although, photobiomodulation therapy garment 20 is illustrated as photobiomodulation therapy headband 22 in FIGS. 1-16, a photobiomodulation therapy garment disclosed herein can be constructed to be donned on a variety of body portions. In some embodiments, a photobiomodulation therapy garment disclosed herein can be configured to wrap about or conform to a wide variety of body parts, with the capability to be moved from one region of interest to another region of interest on the body. In some embodiments, a photobiomodulation therapy garment disclosed herein can be configured specifically to fit a particular body part, such as, e.g., as a head covering, a visor, a neck wrap, a shoulder wrap, a wrist wrap, or an abdominal wrap. In some embodiments, a photobiomodulation therapy garment disclosed herein can be configured to be fitted to a wide variety of body parts of an individual, with the capability to be worn by the individual, such as, e.g., a hat, a shirt, a pants, or an undergarment.

A photobiomodulation therapy garment 20 comprises a garment. Garment can be made flexible, semirigid, or rigid and is constructed to be comfortable to the user's body and configured to behave much like an item of clothing or other donned fashion accessory. In some embodiments, a garment disclosed herein is a fabric material made through weaving, knitting, spreading, felting, stitching, crocheting or bonding. In some embodiments, garment is composed of multiple layers of fabric material. For example, in some embodiments, photobiomodulation therapy garment comprises an outer fabric sheet and an inner fabric sheet. Outer fabric sheet is sized and dimensioned to serve as base for mounting one or more photobiomodulation units and a controller disclosed herein whereas inner fabric assembly is sized and dimensioned to at least cover the one or more photobiomodulation units.

For example, in some embodiments, and referring to FIGS. 2-4, & 7, 8, 15, & 16 photobiomodulation therapy headband 22 comprises garment 30 including an outer fabric sheet 40 and an inner fabric sheet 70 and a photobiomodulation unit 100 sandwiched between outer fabric sheet 40 and inner fabric sheet 70. Outer fabric sheet 40 can be made of a wide variety of natural or synthetic textiles, generally chosen for aesthetic and/or protective qualities. Inner fabric sheet 70 is configured to lie against skin surface S, and can be made of natural or synthetic textile or other material which is comfortable against skin surface S, such as space cotton or the like. As shown in FIGS. 2-7, top and bottom portions of outer fabric sheet 40 and inner fabric sheet 70 are affixed to one another to form a top edge 50 and a bottom edge 52 of garment 30 in a manner that encloses photobiomodulation unit 100 therewithin.

As shown in FIGS. 2, 4-6, 8, 15, & 16 outer fabric sheet 40 of garment 30 also comprises a right head strap 64 extends longitudinally from the right portion 54 of garment 30 and a left head strap 66 extends longitudinally from left portion 56 of garment 30. Slide buckle 60 permits length adjustment of right head strap 64 and slide buckle 62 is connected to right head strap 64 and held to right head strap 64 via a loop created by slide buckle 60. Slide buckle 62 is configured to receive the free end of left head strap 66, where left head strap 66 can include hook and loop mating portions to complete the connection. This head strap arrangement permits easy adjustment of photobiomodulation therapy headband 22 and secure attachment to head H.

Figure 8:
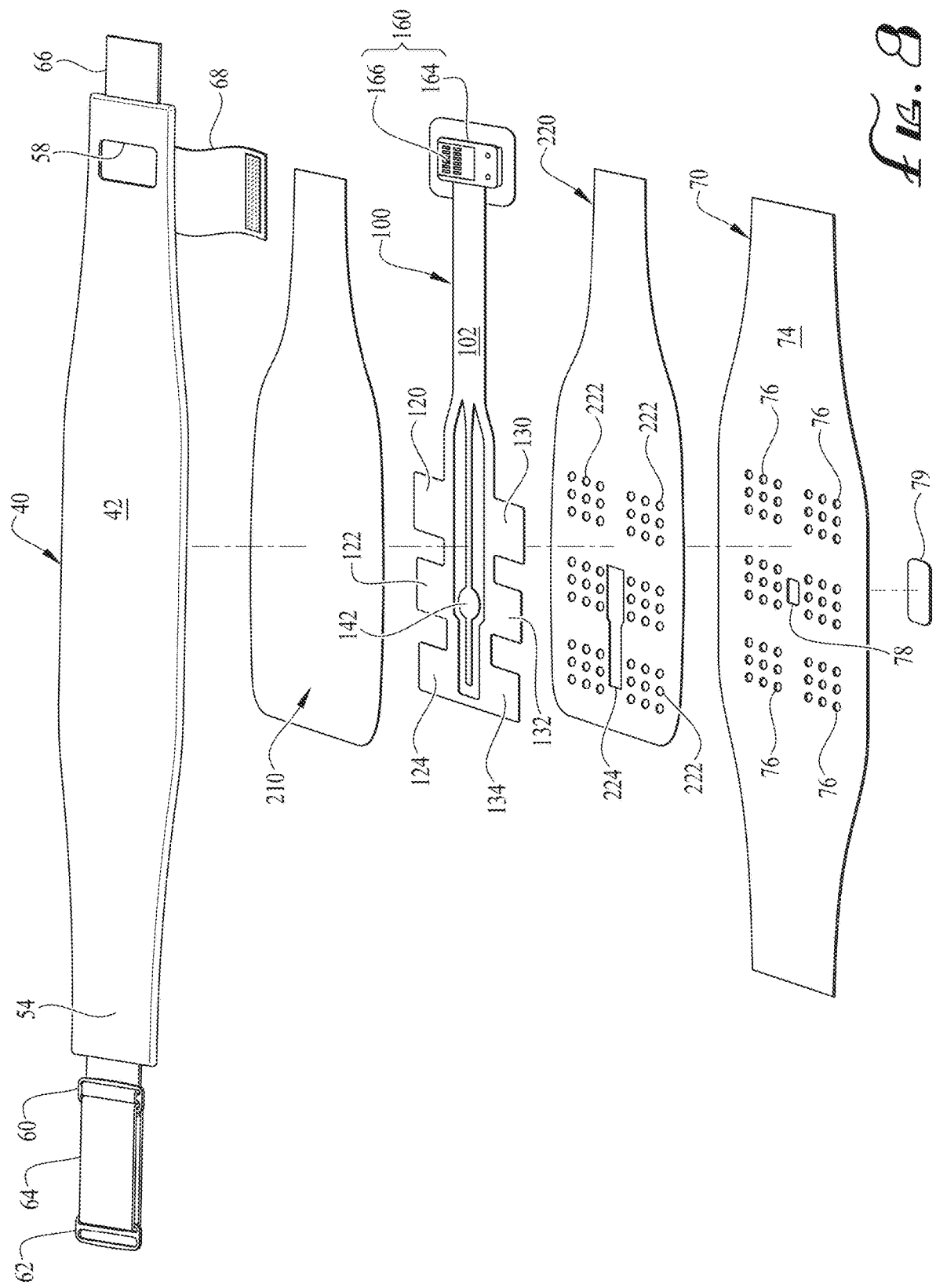
FIG. 8 is an exploded perspective view of the photobiomodulation therapy garment of FIG. 5.

As shown in FIG. 8, outer fabric sheet 40 of garment 30 comprises a terminal rail mount opening 58 sized and dimensioned to receive a terminal rail of a connection terminal disclosed herein in a manner that enables proper engagement of controller 200 to the terminal rail. Referring to FIGS. 2, 4-6, 8, 15, & 16, outer fabric sheet 40 of garment 30 also comprises controller strap 68 extends from a left portion 56 of garment 30. Controller strap 68 is configured to be wrapped about controller 200 once controller 200 is operationally engaged to photobiomodulation unit 100 in order to securely hold controller 200 against outer fabric sheet 40. Controller strap 68 has a first end securely affixed to garment 30 and the second end opposite the first end that can loop around attached controller 200 thereby reversibly securing controller 200 to garment 30 using, e.g., a hook and loop fastener, a buckle or snaps. Controller strap 68 can be composed of a non-elastic or elastic material.

Figure 16:
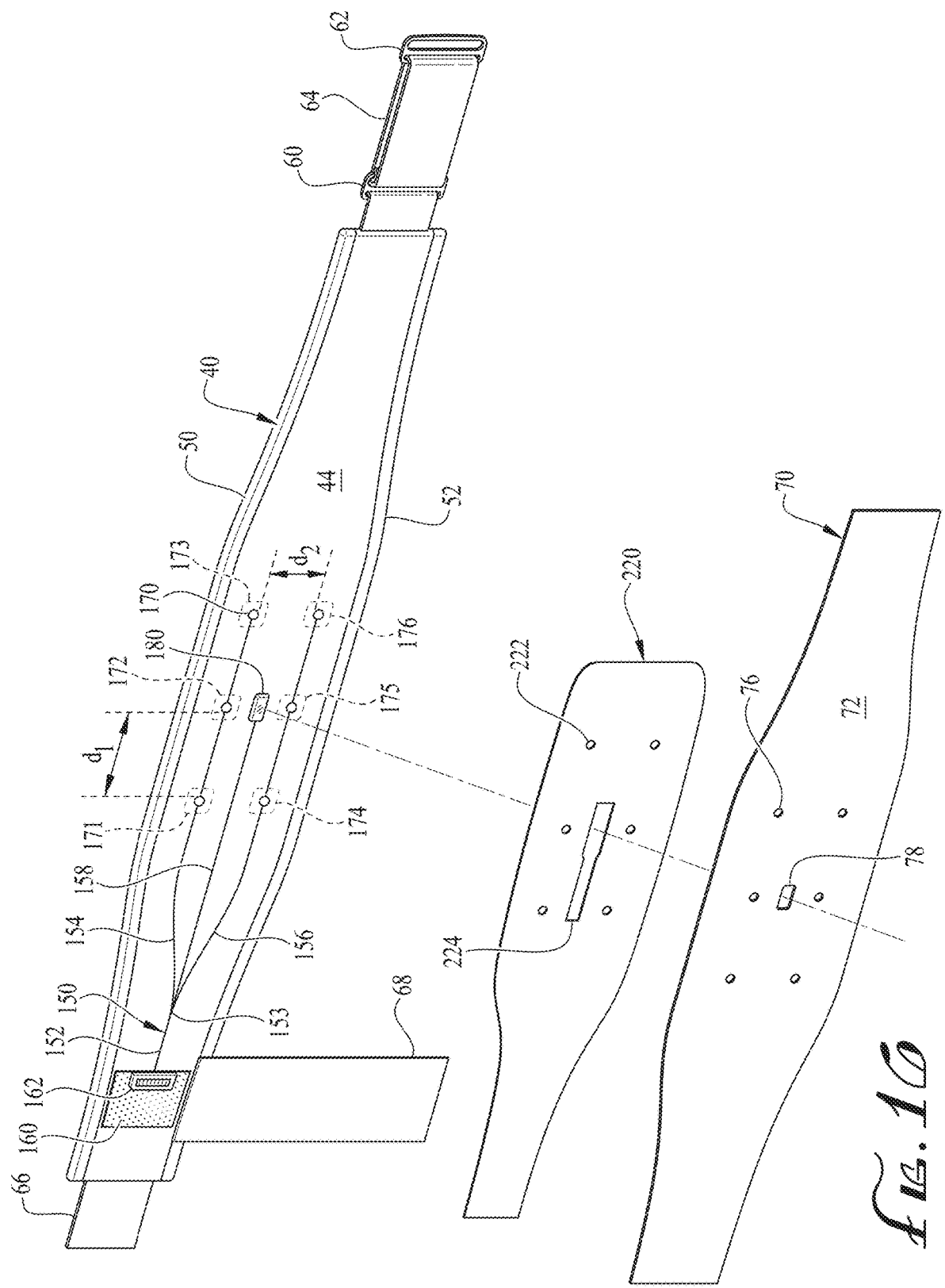
FIG. 16 is an exploded rear perspective view of the photobiomodulation therapy garment disclosed herein, illustrating a liquid wire circuit assembly.
Figures 19A, 19B:
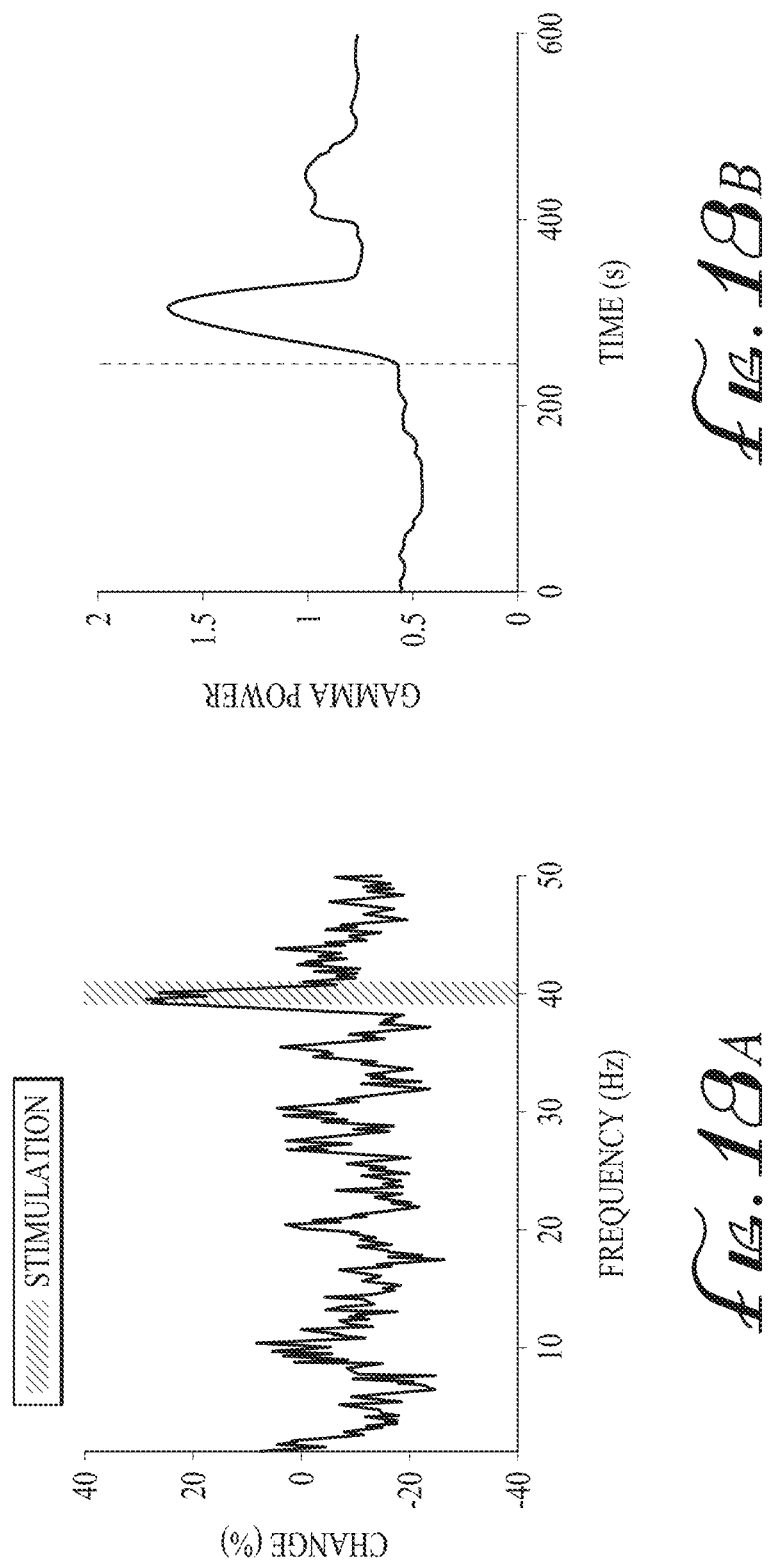

As best seen in FIGS. 8, 15 & 16, inner fabric sheet 70 of garment 30 comprises one or more near infrared light source openings 76 and one or more sensor openings 78. Each of the one or more near infrared light source openings 76 is a cutout positioned on inner fabric sheet 70 so that when assembled each opening 76 is aligned with an infrared light source disclosed herein in a manner that permits light from the infrared light source to emit through the infrared light source opening 76. Similarly, each of the one or more sensor openings 78 is a cutout positioned on inner fabric sheet 70 so that when assembled each opening 78 is aligned with a sensor disclosed herein in a manner that permits the sensor to properly function and collect information from a user through the sensor opening 78.

In some embodiments, and referring to FIGS. 2-4 & 8, inner fabric sheet 70 can include one or more sensor covers 79. Each sensor cover 79 is position over and protects each of the one or more sensors disclosed herein mounted on photobiomodulation unit 100. In addition, each of the one or more sensor covers 79 is configured to be in contact or is placed in close proximity to skin surface S when photobiomodulation therapy garment 20 is donned. Each sensor cover 79 can be attached to inner fabric sheet 70, or photobiomodulation unit 100, and/or sandwiched therebetween. Each sensor cover 79 is constructed of a thin sheet of PVC in this example embodiment, which permits the one or more sensors located thereunder to interact with skin surface S to measure bodily functions, such as one or more of a temperature, a heart rate, a blood oxygen level, and other measurable functions. Further, each sensor cover 79 provides a visible reference to assist a user in properly orientating and donning photobiomodulation therapy garment 20. For example, when placing photobiomodulation therapy headband 22 about head H, the one or more sensor covers 79 can be manually aligned with the nose, placing sensor cover 79 substantially on top of sagittal plane 320.

A photobiomodulation therapy garment 20 also includes a photobiomodulation unit. A photobiomodulation unit includes a connection terminal, one or more near-infrared light sources, one or more sensors and is configured to establish electronic communication with controller 200. In some embodiments, and referring to FIGS. 8, 9 & 11, a photobiomodulation unit 100 comprises a flexible printed circuit board assembly 110 that provides a flexible substrate housing the electrical circuitry which establishes electronic communication between a connection terminal 160 and one or more near-infrared light sources 170, such as, e.g., an infrared light, low-level laser, and/or light emitted diode (LED), one or more sensors 180, and optionally one or more stimulators 194. Connection terminal 160 (generally rigid or semirigid) includes an electronic circuity connector 162 mounted thereon, where electronic circuity connector 162 is configured to provide electronic communication between controller 200 and flexible printed circuit board assembly 110. In these embodiments, flexible printed circuit board assembly 110 is configured to provide flexibility and comfort to the wearer. For example, since photobiomodulation therapy headband 22 must closely match the contours of the forehead, flexible printed circuit board assembly 110 is designed with strategic cutouts to permit maximum flexibility and comfort. In some embodiments, and as shown in FIGS. 8 & 10, flexible printed circuit board assembly 110 comprises a heat-dissipating material 102 on the flexible substrate on the side opposite the electrical circuitry that dispels heat generating by flexible printed circuit board assembly 110 during operation of photobiomodulation therapy garment 20.

Figure 11:
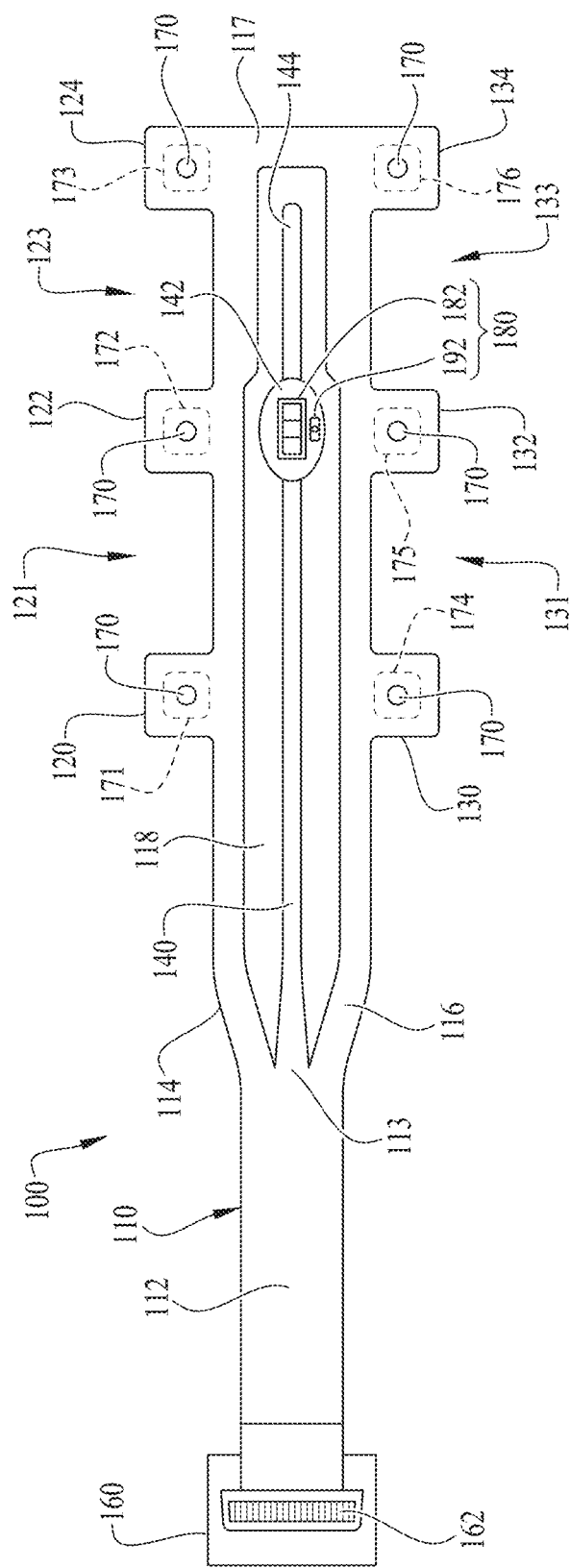
FIG. 11 is a top plan view of a photobiomodulation unit disclosed herein comprising a flexible printed circuit board assembly.

In some embodiments, and referring to FIGS. 9 & 11, flexible printed circuit board assembly 110 is a thin, flat substrate that includes a first surface and a second surface opposite the first surface and is configured as a main strip 112 which extends from connection terminal 160 and trifurcates at a root 113 into a first strip 114, a second strip 116, and a sensor strip 140 extending from the middle. First strip 114 and second strip 116 are connected distally by a connecting portion 117 and all define the bounds of cutout 118. First strip 114 and second strip 116 contain the electronic circuitry needed to establish electronic communication between each near-infrared light source 170 operationally mounted on first strip 114 or second strip 116 and connection terminal 160.

In some embodiments, first strip 114 and second strip 116 each include a series of tabs laterally extending outward therefrom, for mounting thereon near-infrared light sources disclosed herein. For example, as shown in FIGS. 9 & 11, first strip 114 includes a first mounting portion 120, a second mounting portion 122, and a third mounting portion 124, with first mounting portion 120 separated from second mounting portion 122 by a first cutout 121 therebetween, and third mounting portion 124 separated from second mounting portion 122 by a second cutout 123 therebetween. Similarly, second strip 116 includes a first mounting portion 130, a second mounting portion 132, and a third mounting portion 134, with first mounting portion 130 separated from second mounting portion 132 by a first cutout 131 therebetween, and third mounting portion 134 separated from second mounting portion 132 by a second cutout 133 therebetween. First, second, third, mounting portions 120, 122, 124 of first strip 114 and first, second, third, mounting portions 130, 132, 134 of second strip 116 act like gores to permit independent flexible bending of flexible printed circuit board assembly 110. Such flexible bending enables flexible printed circuit board assembly 110 to easily conform to the contours of one or more regions of interest of skin region S and places each of the one or more near-infrared light sources disclosed herein in close proximity to skin surface S with minimal or no gap.

In some embodiments, and referring to FIGS. 9 & 11, sensor strip 140 includes a sensor mounting portion 142 and a free end 144. Sensor strip 140 extends from root 113 into cutout 118 in a manner where cutout 118 provides clearance of sensor strip 140 from first strip 114 and second strip 116 such that sensor strip 140 is disconnected from first strip 114 and second strip 116 except at root 113. Sensor strip 140 contains the electronic circuitry needed to establish electronic communication between each sensor 180 operationally mounted on sensor strip 140 and connection terminal 160. Sensor strip 140 is relatively thin and elongated to permit bending and slight movement of sensor strip 140 relative to the remainder of flexible printed circuit board assembly 110, which is additionally permitted due to a sensor opening 224 provided by a double-sided tape 220 (see FIGS. 8, 15, & 16), which permits easy bending and fitting about head H, with little or no kinks in flexible printed circuit board assembly 110.

In some embodiments, and referring to FIGS. 5, 8, 9, 11, 15, & 16, integrally mounted to one end of flexible printed circuit board assembly 110 is connection terminal 160. Connection terminal 160 comprises electronic circuity connector 162 and a terminal rail mount 164. Electronic circuity connector 162 of connection terminal 160 is located on the same surface of flexible printed circuit board assembly 110 where one or more infrared light sources 170, one or more sensors 180, and one or more stimulators 194 are mounted and contains the electrical circuitry used to establish electronic communication with one or more infrared light sources 170, one or more sensors 180, and one or more stimulators 194. Terminal rail mount 164 of connection terminal 160 is located on flexible printed circuit board assembly 110 on the surface opposite of electronic circuitry connector 162. Terminal rail mount 164 includes a plurality of contacts 166. Terminal rail mount 164 is configured to receive controller 200 and establish electronic communication between photobiomodulation unit 100 and controller 200 which has corresponding contacts that mate with contacts 166 when connected. To permit quick connection and disconnection, controller 200 and terminal rail mount 164 include sliding joinery (e.g., dovetail or tongue and groove like joinery) to capture controller 200 within terminal rail mount 164 and force electrical contact between contacts 166 of terminal rail mount 164 and corresponding contacts protruding though controller 200. After sliding controller 200 into terminal rail mount 164, controller strap 68 is wrapped over controller 200 and fastened to inside portion 44 of outer fabric sheet 40 by a releasable connection, such as hook and loop.

In some embodiments, and referring to FIGS. 15 & 16, photobiomodulation unit 100 comprises a liquid wire circuit assembly 150 that provides electronic communication between connection terminal 160 and one or more near-infrared light sources 170, such as, e.g., an infrared light, low-level laser, and/or light emitted diode (LED), one or more sensors 180, and optionally one or more stimulators 194. A liquid wire comprises a type of metal that remains in the liquid phase at room temperature which is enclosed in a flexible tubing. Owing to its liquid phase nature, liquid metal can make good contact with objects in any shape and can maintain excellent electrical properties upon the deformation of the substrate or the covering film. Non-limiting examples of liquid metal include gallium and alloys such as eutectic gallium—indium. Liquid wire circuit assembly 150 includes connection terminal 160 with electronic circuitry connector 162 mounted thereon, where electronic circuitry connector 162 is configured to provide electrical communication between one or more liquid wire tubes of circuit assembly 150 and connection terminal 160. In these embodiments, liquid wire circuit assembly 150 is configured to provide flexibility and comfort to the wearer. For example, since photobiomodulation therapy headband 22 must closely match the contours of the forehead, liquid wire circuit assembly 150 is designed with strategic cutouts to permit maximum flexibility and comfort.

In some embodiments, and referring to FIGS. 15 & 16, liquid wire circuit assembly 150 comprises a main liquid wire tube 152 which extends from connection terminal 160 and trifurcates at a root 153 into a first liquid wire tube 154, a second liquid wire tube 156, and a sensor liquid wire tube 158 extending from the middle affixed directly to an inner surface of outer fabric sheet 40. First and second liquid wire tubes 154, 156 contain the electronic circuitry needed to establish electrical connection between each near-infrared light source 170 operationally mounted to first or second liquid wire tubes 154, 156 and connection terminal 160 which, in turn provides electrical connection to controller 200. Sensor liquid wire tube 158 contains the electronic circuitry needed to establish electrical communication between each sensor 180 and/or each stimulator 194 operationally mounted to sensor liquid wire tube 158 and connection terminal 160 which, in turn provides electrical connection to controller 200. The affixing of first and second liquid wire tubes 154, 156 and sensor liquid wire tube 158 directly to an inner surface of outer fabric sheet 40 enables liquid wire circuit assembly 150 to easily conform to the contours of one or more regions of interest of skin region S and places each of the one or more near-infrared light sources disclosed herein in close proximity to skin surface S with minimal or no gap. Although not shown, liquid wire circuit assembly 150 can be configured in an arrangement similar to the arrangements shown for flexible printed circuit board assembly 110 of FIGS. 12-14.

Referring to FIGS. 9-15, photobiomodulation unit 100 also comprises one or more near-infrared light source 170 each being configured to emit near infrared light in a wavelength range of 700 nm to 1600 nm. In some embodiments, near-infrared light source 170 emits light having a wavelength of, e.g., about 700 nm, about 750 nm, about 800 nm, about 900 nm, about 1000 nm, about 1100 nm, about 1200 nm, about 1.300 nm, about 1400 nm, or about 1500 nm. In some embodiments, near-infrared light source 170 emits light having a wavelength of, e.g., at least 700 nm, at least 750 nm, at least 800 nm, at least 850 nm, at least 900 nm, at least 1000 nm, at least 1100 nm, at least 1200 nm, at least 1.300 nm, at least 1400 nm, or at least 1500 nm. In some embodiments, near-infrared light source 170 emits light having a wavelength of, e.g., at most 700 nm, at most 750 nm, at most 800 nm, at most 850 nm, at most 900 nm, at most 1000 nm, at most 1100 nm, at most 1200 nm, at most 1.300 nm, at most 1400 nm, or at most 1500 nm.

In some embodiments, near-infrared light source 170 emits light having a wavelength of, e.g., about 700 nm to about 750 nm, about 700 nm to about 800 nm, about 700 nm to about 900 nm, about 700 nm to about 1000 nm, about 700 nm to about 1100 nm, about 700 nm to about 1200 nm, about 700 nm to about 1300 nm, about 700 nm to about 1400 nm, about 700 nm to about 1500 nm, about 750 nm to about 800 nm, about 750 nm to about 850 nm, about 750 nm to about 900 nm, about 750 nm to about 1000 nm, about 750 nm to about 1100 nm, about 750 nm to about 1200 nm, about 750 nm to about 1300 nm, about 750 nm to about 1400 nm, about 750 nm to about 1500 nm, about 800 nm to about 850 nm, about 800 nm to about 900 nm, about 800 nm to about 1000 nm, about 800 nm to about 1100 nm, about 800 nm to about 1200 nm, about 800 nm to about 1300 nm, about 800 nm to about 1400 nm, about 800 nm to about 1500 nm, about 850 nm to about 900 nm, about 850 nm to about 1000 nm, about 850 nm to about 1100 nm, about 850 nm to about 1200 nm, about 850 nm to about 1300 nm, about 850 nm to about 1400 nm, about 850 nm to about 1500 nm, about 900 nm to about 1000 nm, about 900 nm to about 1100 nm, about 900 nm to about 1200 nm, about 900 nm to about 1300 nm, about 900 nm to about 1400 nm, about 900 nm to about 1500 nm, about 1000 nm to about 1100 nm, about 1000 nm to about 1200 nm, about 1000 nm to about 1300 nm, about 1000 nm to about 1400 nm, about 1000 nm to about 1500 nm, about 1100 nm to about 1200 nm, about 1100 nm to about 1300 nm, about 1100 nm to about 1400 nm, about 1100 nm to about 1500 nm, about 1200 nm to about 1300 nm, about 1200 nm to about 1400 nm, about 1200 nm to about 1500 nm, about 1300 nm to about 1400 nm, about 1300 nm to about 1500 nm, or about 1400 nm to about 1500 nm.

In some embodiments, one or more near-infrared light source 170 are each configured to emit near infrared light in a pulse wave (or frequency) range of about 1 Hz to about 100 Hz. In some embodiments, near-infrared light source 170 emits light having a pulse wave of, e.g., about 10 Hz, about 20 Hz, about 30 Hz, about 40 Hz, about 50 Hz, about 60 Hz, about 70 Hz, about 80 Hz, about 90 Hz, or about 100 Hz. In some embodiments, near-infrared light source 170 emits light having a pulse wave of, e.g., at least 10 Hz, at least 20 Hz, at least 30 Hz, at least 40 Hz, at least 50 Hz, at least 60

Hz, at least 70 Hz, at least 80 Hz, at least 90 Hz, or at least 100 Hz. In some embodiments, near-infrared light source 170 emits light having a pulse wave of, e.g., at most 10 Hz, at most 20 Hz, at most 30 Hz, at most 40 Hz, at most 50 Hz, at most 60 Hz, at most 70 Hz, at most 80 Hz, at most 90 Hz, or at most 100 Hz. In some embodiments, near-infrared light source 170 emits light having a pulse wave of, e.g., about 10 Hz to about 20 Hz, about 10 Hz to about 30 Hz, about 10 Hz to about 40 Hz, about 10 Hz to about 50 Hz, about 10 Hz to about 60 Hz, about 10 Hz to about 70 Hz, about 10 Hz to about 80 Hz, about 10 Hz to about 90 Hz, about 10 Hz to about 100 Hz, about 20 Hz to about 30 Hz, about 20 Hz to about 40 Hz, about 20 Hz to about 50 Hz, about 20 Hz to about 60 Hz, about 20 Hz to about 70 Hz, about 20 Hz to about 80 Hz, about 20 Hz to about 90 Hz, about 20 Hz to about 100 Hz, about 30 Hz to about 40 Hz, about 30 Hz to about 50 Hz, about 30 Hz to about 60 Hz, about 30 Hz to about 70 Hz, about 30 Hz to about 80 Hz, about 30 Hz to about 90 Hz, about 30 Hz to about 100 Hz, about 40 Hz to about 50 Hz, about 40 Hz to about 60 Hz, about 40 Hz to about 70 Hz, about 40 Hz to about 80 Hz, about 40 Hz to about 90 Hz, about 40 Hz to about 100 Hz, about 50 Hz to about 60 Hz, about 50 Hz to about 70 Hz, about 50 Hz to about 80 Hz, about 50 Hz to about 90 Hz, about 50 Hz to about 100 Hz, about 60 Hz to about 70 Hz, about 60 Hz to about 80 Hz, about 60 Hz to about 90 Hz, about 60 Hz to about 100 Hz, about 70 Hz to about 80 Hz, about 70 Hz to about 90 Hz, about 70 Hz to about 100 Hz, about 80 Hz to about 90 Hz, about 80 Hz to about 100 Hz, or about 90 Hz to about 100 Hz.

In some embodiments, one or more near-infrared light source 170 are each configured to emit near infrared light in a pulse wave (or frequency) range of about 100 Hz to about 1000 Hz. In some embodiments, near-infrared light source 170 emits light having a pulse wave of, e.g., about 100 Hz, about 200 Hz, about 300 Hz, about 400 Hz, about 500 Hz, about 600 Hz, about 700 Hz, about 800 Hz, about 900 Hz, or about 1000 Hz. In some embodiments, near-infrared light source 170 emits light having a pulse wave of, e.g., at least 100 Hz, at least 200 Hz, at least 300 Hz, at least 400 Hz, at least 500 Hz, at least 600 Hz, at least 700 Hz, at least 800 Hz, at least 900 Hz, or at least 1000 Hz. In some embodiments, near-infrared light source 170 emits light having a pulse wave of, e.g., at most 100 Hz, at most 200 Hz, at most 300 Hz, at most 400 Hz, at most 500 Hz, at most 600 Hz, at most 700 Hz, at most 800 Hz, at most 900 Hz, or at most 1000 Hz. In some embodiments, near-infrared light source 170 emits light having a pulse wave of, e.g., about 100 Hz to about 200 Hz, about 100 Hz to about 300 Hz, about 100 Hz to about 400 Hz, about 100 Hz to about 500 Hz, about 100 Hz to about 600 Hz, about 100 Hz to about 700 Hz, about 100 Hz to about 800 Hz, about 100 Hz to about 900 Hz, about 100 Hz to about 1000 Hz, about 200 Hz to about 300 Hz, about 200 Hz to about 400 Hz, about 200 Hz to about 500 Hz, about 200 Hz to about 600 Hz, about 200 Hz to about 700 Hz, about 200 Hz to about 800 Hz, about 200 Hz to about 900 Hz, about 200 Hz to about 1000 Hz, about 300 Hz to about 400 Hz, about 300 Hz to about 500 Hz, about 300 Hz to about 600 Hz, about 300 Hz to about 700 Hz, about 300 Hz to about 800 Hz, about 300 Hz to about 900 Hz, about 300 Hz to about 1000 Hz, about 400 Hz to about 500 Hz, about 400 Hz to about 600 Hz, about 400 Hz to about 700 Hz, about 400 Hz to about 800 Hz, about 400 Hz to about 900 Hz, about 400 Hz to about 1000 Hz, about 500 Hz to about 600 Hz, about 500 Hz to about 700 Hz, about 500 Hz to about 800 Hz, about 500 Hz to about 900 Hz, about 500 Hz to about 1000 Hz, about 600 Hz to about 700 Hz, about 600 Hz to about 800 Hz, about 600 Hz to about 900 Hz, about 600 Hz to about 1000 Hz, about 700 Hz to about 800 Hz, about 700 Hz to about 900 Hz, about 700 Hz to about 1000 Hz, about 800 Hz to about 900 Hz, about 800 Hz to about 1000 Hz, or about 900 Hz to about 1000 Hz.

In some embodiments, one or more near-infrared light source 170 are each configured to emit near infrared light in a pulse wave (or frequency) range of about 1000 Hz to about 5000 Hz. In some embodiments, near-infrared light source 170 emits light having a pulse wave of, e.g., about 1000 Hz, about 2000 Hz, about 3000 Hz, about 4000 Hz, or about 5000 Hz. In some embodiments, near-infrared light source 170 emits light having a pulse wave of, e.g., at least 1000 Hz, at least 2000 Hz, at least 3000 Hz, at least 4000 Hz, or at least 5000 Hz. In some embodiments, near-infrared light source 170 emits light having a pulse wave of, e.g., at most 1000 Hz, at most 2000 Hz, at most 3000 Hz, at most 4000 Hz, or at most 5000 Hz. In some embodiments, near-infrared light source 170 emits light having a pulse wave of, e.g., about 1000 Hz to about 2000 Hz, about 1000 Hz to about 3000 Hz, about 1000 Hz to about 4000 Hz, about 1000 Hz to about 5000 Hz, about 2000 Hz to about 3000 Hz, about 2000 Hz to about 4000 Hz, about 2000 Hz to about 5000 Hz, about 3000 Hz to about 4000 Hz, about 3000 Hz to about 5000 Hz, or about 4000 Hz to about 5000 Hz.

In some embodiments, one or more near-infrared light source 170 are each configured to emit near infrared light in a radiant energy range of about 100 J to about 1100 J. In some embodiments, near-infrared light source 170 has a radiant energy of, e.g., about 100 J, about 200 J, about 300 J, about 400 J, about 500 J, about 600 J, about 700 J, about 800 J, about 900 J, about 1000 J, or about 1100 J. In some embodiments, near-infrared light source 170 has a radiant energy of, e.g., at least 100 J, at least 200 J, at least 300 J, at least 400 J, at least 500 J, at least 600 J, at least 700 J, at least 800 J, at least 900 J, at least 1000 J, or at least 1100 J. In some embodiments, near-infrared light source 170 has a radiant energy of, e.g., at most 100 J, at most 200 J, at most 300 J, at most 400 J, at most 500 J, at most 600 J, at most 700 J, at most 800 J, at most 900 J, at most 1000 J, or at most 1100 J. In some embodiments, near-infrared light source 170 has a radiant energy of, e.g., about 100 J to about 200 J, about 100 J to about 300 J, about 100 J to about 400 J, about 100 J to about 500 J, about 100 J to about 600 J, about 100 J to about 700 J, about 100 J to about 800 J, about 100 J to about 900 J, about 100 J to about 1000 J, about 100 J to about 1100 J, about 200 J to about 300 J, about 200 J to about 400 J, about 200 J to about 500 J, about 200 J to about 600 J, about 200 J to about 700 J, about 200 J to about 800 J, about 200 J to about 900 J, about 200 J to about 1000 J, about 200 J to about 1100 J, about 300 J to about 400 J, about 300 J to about 500 J, about 300 J to about 600 J, about 300 J to about 700 J, about 300 J to about 800 J, about 300 J to about 900 J, about 300 J to about 1000 J, about 300 J to about 1100 J, about 400 J to about 500 J, about 400 J to about 600 J, about 400 J to about 700 J, about 400 J to about 800 J, about 400 J to about 900 J, about 400 J to about 1000 J, about 400 J to about 1100 J, about 500 J to about 600 J, about 500 J to about 700 J, about 500 J to about 800 J, about 500 J to about 900 J, about 500 J to about 1000 J, about 500 J to about 1100 J, about 600 J to about 700 J, about 600 J to about 800 J, about 600 J to about 900 J, about 600 J to about 1000 J, about 600 J to about 1100 J, about 700 J to about 800 J, about 700 J to about 900 J, about 700 J to about 1000 J, about 700 J to about 1100 J, about 800 J to about 900 J, about 800 J to about 1000 J, about 800 J to about 1100 J, about 900 J to about 1000 J, about 900 J to about 1100 J, or about 1000 J to about 1100 J.

In some embodiments, one or more near-infrared light source 170 are each configured to emit near infrared light in an irradiance (flux density) range of about 5 mW/cm$^2$ to about 100 mW/cm$^2$. In some embodiments, near-infrared light source 170 has an irradiance (flux density) of, e.g., about 5 mW/cm$^2$, about 10 mW/cm$^2$, about 15 mW/cm$^2$, about 20 mW/cm$^2$, about 25 mW/cm$^2$, about 30 mW/cm$^2$, about 35 mW/cm$^2$, about 40 mW/cm$^2$, about 50 mW/cm$^2$, about 60 mW/cm$^2$, about 70 mW/cm$^2$, about 80 mW/cm$^2$, about 90 mW/cm$^2$, or about 100 mW/cm$^2$ In some embodiments, near-infrared light source 170 has an irradiance (flux density) of, e.g., at least 5 mW/cm$^2$, at least 10 mW/cm$^2$, at least 15 mW/cm$^2$, at least 20 mW/cm$^2$, at least 25 mW/cm$^2$, at least 30 mW/cm$^2$, at least 35 mW/cm$^2$, at least 40 mW/cm$^2$, at least 50 mW/cm$^2$, at least 60 mW/cm$^2$, at least 70 mW/cm$^2$, at least 80 mW/cm$^2$, at least 90 mW/cm$^2$, or at least 100 mW/cm$^2$ In some embodiments, near-infrared light source 170 has an irradiance (flux density) of, e.g., at most 5 mW/cm$^2$, at most 10 mW/cm$^2$, at most 15 mW/cm$^2$, at most 20 mW/cm$^2$, at most 25 mW/cm$^2$, at most 30 mW/cm$^2$, at most 35 mW/cm$^2$, at most 40 mW/cm$^2$, at most 50 mW/cm$^2$, at most 60 mW/cm$^2$, at most 70 mW/cm$^2$, at most 80 mW/cm$^2$, at most 90 mW/cm$^2$, or at most 100 mW/cm$^2$ In some embodiments, near-infrared light source 170 has an irradiance (flux density) of, e.g., about 5 mW/cm$^2$ to about 10 mW/cm$^2$, about 5 mW/cm$^2$ to about 15 mW/cm$^2$, about 5 mW/cm$^2$ to about 20 mW/cm$^2$, about 5 mW/cm$^2$ to about 25 mW/cm$^2$, about 5 mW/cm$^2$ to about 30 mW/cm$^2$, about 5 mW/cm$^2$ to about 35 mW/cm$^2$, about 10 mW/cm$^2$ to about 15 mW/cm$^2$, about 10 m W/cm$^2$ to about 20 mW/cm$^2$, about 10 mW/cm$^2$ to about 25 mW/cm$^2$, about 10 mW/cm$^2$ to about 30 mW/cm$^2$, about 10 mW/cm$^2$ to about 35 mW/cm$^2$, about 15 mW/cm$^2$ to about 20 mW/cm$^2$, about 15 mW/cm$^2$ to about 25 mW/cm$^2$, about 15 mW/cm$^2$ to about 30 mW/cm$^2$, about 15 mW/cm$^2$ to about 35 mW/cm$^2$, about 20 mW/cm$^2$ to about 25 mW/cm$^2$, about 20 mW/cm$^2$ to about 30 mW/cm$^2$, about 20 mW/cm$^2$ to about 35 mW/cm$^2$, about 25 mW/cm$^2$ to about 30 mW/cm$^2$, about 25 mW/cm$^2$ to about 35 mW/cm$^2$, or about 30 mW/cm$^2$ to about 35 mW/cm$^2$. In some embodiments, near-infrared light source 170 has an irradiance (flux density) of, e.g., about 20 mW/cm$^2$ to about 50 mW/cm$^2$, about 20 mW/cm$^2$ to about 60 mW/cm$^2$, about 20 mW/cm$^2$ to about 70 mW/cm$^2$, about 20 mW/cm$^2$ to about 80 mW/cm$^2$, about 20 mW/cm$^2$ to about 90 mW/cm$^2$, about 20 mW/cm$^2$ to about 100 mW/cm$^2$, about 30 mW/cm$^2$ to about 60 mW/cm$^2$, about 30 mW/cm$^2$ to about 70 mW/cm$^2$, about 30 mW/cm$^2$ to about 80 mW/cm$^2$, about 30 mW/cm$^2$ to about 90 mW/cm$^2$, about 30 mW/cm$^2$ to about 100 mW/cm$^2$, about 40 mW/cm$^2$ to about 60 mW/cm$^2$, about 40 mW/cm$^2$ to about 70 mW/cm$^2$, about 40 mW/cm$^2$ to about 80 mW/cm$^2$, about 40 mW/cm$^2$ to about 90 mW/cm$^2$, about 40 mW/cm$^2$ to about 100 mW/cm$^2$, about 50 mW/cm$^2$ to about 60 mW/cm$^2$, about 50 mW/cm$^2$ to about 70 mW/cm$^2$, about 50 mW/cm$^2$ to about 80 mW/cm$^2$, about 50 mW/cm$^2$ to about 90 mW/cm$^2$, about 50 mW/cm$^2$ to about 100 mW/cm$^2$, about 60 mW/cm$^2$ to about 70 mW/cm$^2$, about 60 mW/cm$^2$ to about 80 mW/cm$^2$, about 60 mW/cm$^2$ to about 90 mW/cm$^2$, about 60 mW/cm$^2$ to about 100 mW/cm$^2$, about 70 mW/cm$^2$ to about 80 mW/cm$^2$, about 70 mW/cm$^2$ to about 90 mW/cm$^2$, about 70 mW/cm$^2$ to about 100 mW/cm$^2$, about 80 mW/cm$^2$ to about 90 mW/cm$^2$, about 80 mW/cm$^2$ to about 100 mW/cm$^2$, or about 90 mW/cm$^2$ to about 100 mW/cm$^2$.

In some embodiments, one or more near-infrared light source 170 are each configured to emit near infrared light in an irradiance (flux density) range of about 100 mW/cm$^2$ to about 1000 mW/cm$^2$. In some embodiments, near-infrared light source 170 has an irradiance (flux density) of, e.g., about 100 mW/cm$^2$, about 200 mW/cm$^2$, about 300 mW/cm$^2$, about 400 mW/cm$^2$, about 500 mW/cm$^2$, about 600 mW/cm$^2$, about 700 mW/cm$^2$, about 800 mW/cm$^2$, about 900 mW/cm$^2$, or about 1000 mW/cm$^2$. In some embodiments, near-infrared light source 170 has an irradiance (flux density) of, e.g., at least 100 mW/cm$^2$, at least 200 mW/cm$^2$, at least 300 mW/cm$^2$, at least 400 mW/cm$^2$, at least 500 mW/cm$^2$, at least 600 mW/cm$^2$, at least 700 mW/cm$^2$, at least 800 mW/cm$^2$, at least 900 mW/cm$^2$, or at least 1000 mW/cm$^2$. In some embodiments, near-infrared light source 170 has an irradiance (flux density) of, e.g., at most 100 mW/cm$^2$, at most 200 mW/cm$^2$, at most 300 mW/cm$^2$, at most 400 mW/cm$^2$, at most 500 mW/cm$^2$, at most 600 mW/cm$^2$, at most 700 mW/cm$^2$, at most 800 mW/cm$^2$, at most 900 mW/cm$^2$, or at most 1000 mW/cm$^2$. In some embodiments, near-infrared light source 170 has an irradiance (flux density) of, e.g., about 100 mW/cm$^2$ to about 200 mW/cm$^2$, about 100 mW/cm$^2$ to about 300 mW/cm$^2$, about 100 mW/cm$^2$ to about 400 mW/cm$^2$, about 100 mW/cm$^2$ to about 500 mW/cm$^2$, about 100 mW/cm$^2$ to about 600 mW/cm$^2$, about 100 mW/cm$^2$ to about 700 mW/cm$^2$, about 100 mW/cm$^2$ to about 800 mW/cm$^2$, about 100 mW/cm$^2$ to about 900 mW/cm$^2$, about 100 mW/cm$^2$ to about 1000 mW/cm$^2$, about 200 mW/cm$^2$ to about 300 mW/cm$^2$, about 200 mW/cm$^2$ to about 400 mW/cm$^2$, about 200 mW/cm$^2$ to about 500 mW/cm$^2$, about 200 mW/cm$^2$ to about 600 mW/cm$^2$, about 200 mW/cm$^2$ to about 700 mW/cm$^2$, about 200 mW/cm$^2$ to about 800 mW/cm$^2$, about 200 mW/cm$^2$ to about 900 mW/cm$^2$, about 200 mW/cm$^2$ to about 1000 mW/cm$^2$, about 300 mW/cm$^2$ to about 400 mW/cm$^2$, about 300 mW/cm$^2$ to about 500 mW/cm$^2$, about 300 mW/cm$^2$ to about 600 mW/cm$^2$, about 300 mW/cm$^2$ to about 700 mW/cm$^2$, about 300 mW/cm$^2$ to about 800 mW/cm$^2$, about 300 mW/cm$^2$ to about 900 mW/cm$^2$, about 300 mW/cm$^2$ to about 1000 mW/cm$^2$, about 400 mW/cm$^2$ to about 500 mW/cm$^2$, about 400 mW/cm$^2$ to about 600 mW/cm$^2$, about 400 mW/cm$^2$ to about 700 mW/cm$^2$, about 400 mW/cm$^2$ to about 800 mW/cm$^2$, about 400 mW/cm$^2$ to about 900 mW/cm$^2$, about 400 mW/cm$^2$ to about 1000 mW/cm$^2$, about 500 mW/cm$^2$ to about 600 mW/cm$^2$, about 500 mW/cm$^2$ to about 700 mW/cm$^2$, about 500 mW/cm$^2$ to about 800 mW/cm$^2$, about 500 mW/cm$^2$ to about 900 mW/cm$^2$, about 500 mW/cm$^2$ to about 1000 mW/cm$^2$, about 600 mW/cm$^2$ to about 700 mW/cm$^2$, about 600 mW/cm$^2$ to about 800 mW/cm$^2$, about 600 mW/cm$^2$ to about 900 mW/cm$^2$, about 600 mW/cm$^2$ to about 1000 mW/cm$^2$, about 700 mW/cm$^2$ to about 800 mW/cm$^2$, about 700 mW/cm$^2$ to about 900 mW/cm$^2$, about 700 mW/cm$^2$ to about 1000 mW/cm$^2$, about 800 mW/cm$^2$ to about 900 mW/cm$^2$, about 800 mW/cm$^2$ to about 1000 mW/cm$^2$, or about 900 mW/cm$^2$ to about 1000 mW/cm$^2$.

In some embodiments, one or more near-infrared light source 170 are each configured to emit near infrared light in a radiant exposure (fluence) range of about 5 J/cm$^2$ to about 100 J/cm$^2$. In some embodiments, near-infrared light source 170 has a radiant exposure (fluence) of, e.g., about 5 J/cm$^2$, about 10 J/cm$^2$, about 15 J/cm$^2$, about 20 J/cm$^2$, about 30 J/cm$^2$, about 40 J/cm$^2$, about 50 J/cm$^2$, about 70 J/cm$^2$, about 70 J/cm$^2$, about 75 J/cm$^2$, about 80 J/cm$^2$, about 90 J/cm$^2$, or about 100 J/cm$^2$ In some embodiments, near-infrared light source 170 has a radiant exposure (fluence) of, e.g., at least 5 J/cm$^2$, at least 10 J/cm$^2$, at least 15 J/cm$^2$, at least 20 J/cm$^2$, at least 30 J/cm², at least 40 J/cm², at least 50 J/cm², at least 70 J/cm², at least 70 J/cm², at least 75 J/cm², at least 80 J/cm², at least 90 J/cm², or at least 100 J/cm² In some embodiments, near-infrared light source 170 has a radiant exposure (fluence) of, e.g., at most 5 J/cm², at most 10 J/cm², at most 15 J/cm², at most 20 J/cm², at most 30 J/cm², at most 40 J/cm², at most 50 J/cm², at most 70 J/cm², at most 70 J/cm², at most 75 J/cm², at most 80 J/cm², at most 90 J/cm², or at most 100 J/cm². In some embodiments, near-infrared light source 170 has a radiant exposure (fluence) of, e.g., about 5 J/cm² to about 10 J/cm², about 5 J/cm² to about 15 J/cm², about 5 J/cm² to about 20 J/cm², about 5 J/cm² to about 30 J/cm², about 5 J/cm² to about 40 J/cm², about 5 J/cm² to about 50 J/cm², about 5 J/cm² to about 60 J/cm², about 5 J/cm² to about 70 J/cm², about 5 J/cm² to about 75 J/cm², about 5 J/cm² to about 80 J/cm², about 5 J/cm² to about 90 J/cm², about 5 J/cm² to about 100 J/cm², about 10 J/cm² to about 15 J/cm², about 10 J/cm² to about 20 J/cm², about 10 J/cm² to about 30 J/cm², about 10 J/cm² to about 40 J/cm², about 10 J/cm² to about 50 J/cm², about 10 J/cm² to about 60 J/cm², about 10 J/cm² to about 70 J/cm², about 10 J/cm² to about 75 J/cm², about 10 J/cm² to about 80 J/cm², about 10 J/cm² to about 90 J/cm², about 10 J/cm² to about 100 J/cm², about 20 J/cm² to about 30 J/cm², about 20 J/cm² to about 40 J/cm², about 20 J/cm² to about 50 J/cm², about 20 J/cm² to about 60 J/cm², about 20 J/cm² to about 70 J/cm², about 20 J/cm² to about 75 J/cm², about 20 J/cm² to about 80 J/cm², about 20 J/cm² to about 90 J/cm², about 20 J/cm² to about 100 J/cm², about 30 J/cm² to about 40 J/cm², about 30 J/cm² to about 50 J/cm², about 30 J/cm² to about 60 J/cm², about 30 J/cm² to about 70 J/cm², about 30 J/cm² to about 75 J/cm², about 30 J/cm² to about 80 J/cm², about 30 J/cm² to about 90 J/cm², about 30 J/cm² to about 100 J/cm², about 40 J/cm² to about 50 J/cm², about 40 J/cm² to about 60 J/cm², about 40 J/cm² to about 70 J/cm², about 40 J/cm² to about 75 J/cm², about 40 J/cm² to about 80 J/cm², about 40 J/cm² to about 90 J/cm², about 40 J/cm² to about 100 J/cm², about 50 J/cm² to about 60 J/cm², about 50 J/cm² to about 70 J/cm², about 50 J/cm² to about 75 J/cm², about 50 J/cm² to about 80 J/cm², about 50 J/cm² to about 90 J/cm², about 50 J/cm² to about 100 J/cm², about 60 J/cm² to about 70 J/cm², about 60 J/cm² to about 80 J/cm², about 60 J/cm² to about 90 J/cm², about 60 J/cm² to about 100 J/cm², about 70 J/cm² to about 80 J/cm², about 70 J/cm² to about 90 J/cm², about 70 J/cm² to about 100 J/cm², about 80 J/cm² to about 90 J/cm², about 80 J/cm² to about 100 J/cm², or about 90 J/cm² to about 100 J/cm².

In some embodiments, one or more near-infrared light source 170 are each configured to emit near infrared light in a radiant exposure (fluence) range of about 100 J/cm² to about 1000 J/cm². In some embodiments, near-infrared light source 170 has a radiant exposure (fluence) of, e.g., about 100 J/cm², about 200 J/cm², about 300 J/cm², about 400 J/cm², about 500 J/cm², about 600 J/cm², about 700 J/cm², about 800 J/cm², about 900 J/cm², or about 1000 J/cm². In some embodiments, near-infrared light source 170 has a radiant exposure (fluence) of, e.g., at least 100 J/cm², at least 200 J/cm², at least 300 J/cm², at least 400 J/cm², at least 500 J/cm², at least 600 J/cm², at least 700 J/cm², at least 800 J/cm², at least 900 J/cm², or at least 1000 J/cm². In some embodiments, near-infrared light source 170 has a radiant exposure (fluence) of, e.g., at most 100 J/cm², at most 200 J/cm², at most 300 J/cm², at most 400 J/cm², at most 500 J/cm², at most 600 J/cm², at most 700 J/cm², at most 800 J/cm², at most 900 J/cm², or at most 1000 J/cm². In some embodiments, near-infrared light source 170 has a radiant exposure (fluence) of, e.g., about 100 J/cm² to about 200 J/cm², about 100 J/cm² to about 300 J/cm², about 100 J/cm² to about 400 J/cm², about 100 J/cm² to about 500 J/cm², about 100 J/cm² to about 600 J/cm², about 100 J/cm² to about 700 J/cm², about 100 J/cm² to about 800 J/cm², about 100 J/cm² to about 900 J/cm², about 100 J/cm² to about 1000 J/cm², about 200 J/cm² to about 300 J/cm², about 200 J/cm² to about 400 J/cm², about 200 J/cm² to about 500 J/cm², about 200 J/cm² to about 600 J/cm², about 200 J/cm² to about 700 J/cm², about 200 J/cm² to about 800 J/cm², about 200 J/cm² to about 900 J/cm², about 200 J/cm² to about 1000 J/cm², about 300 J/cm² to about 400 J/cm², about 300 J/cm² to about 500 J/cm², about 300 J/cm² to about 600 J/cm², about 300 J/cm² to about 700 J/cm², about 300 J/cm² to about 800 J/cm², about 300 J/cm² to about 900 J/cm², about 300 J/cm² to about 1000 J/cm², about 400 J/cm² to about 500 J/cm², about 400 J/cm² to about 600 J/cm², about 400 J/cm² to about 700 J/cm², about 400 J/cm² to about 800 J/cm², about 400 J/cm² to about 900 J/cm², about 400 J/cm² to about 1000 J/cm², about 500 J/cm² to about 600 J/cm², about 500 J/cm² to about 700 J/cm², about 500 J/cm² to about 800 J/cm², about 500 J/cm² to about 900 J/cm², about 500 J/cm² to about 1000 J/cm², about 600 J/cm² to about 700 J/cm², about 600 J/cm² to about 800 J/cm², about 600 J/cm² to about 900 J/cm², about 600 J/cm² to about 1000 J/cm², about 700 J/cm² to about 800 J/cm², about 700 J/cm² to about 900 J/cm², about 700 J/cm² to about 1000 J/cm², about 800 J/cm² to about 900 J/cm², about 800 J/cm² to about 1000 J/cm², or about 900 J/cm² to about 1000 J/cm².

In some embodiments, near-infrared light source 170 is a high powered infrared light source. In some embodiments, a high powered near-infrared light source has a radiant flux (power) of, e.g., about 400 mW, about 425 mW, about 450 mW, about 500 mW, about 525 mW, about 550 mW, about 575 mW or about 600 mW. In some embodiments, a high powered near-infrared light source has a radiant flux (power) of, e.g., at least 400 mW, at least 425 mW, at least 450 mW, at least 500 mW, at least 525 mW, at least 550 mW, at least 575 mW or at least 600 mW. In some embodiments, a high powered near-infrared light source has a radiant flux (power) of, e.g., at most 400 mW, at most 425 mW, at most 450 mW, at most 500 mW, at most 525 mW, at most 550 mW, at most 575 mW or at most 600 mW. In some embodiments, a high powered near-infrared light source has a radiant flux (power) of, e.g., about 400 mW to about 450 mW, about 400 mW to about 500 mW, about 400 mW to about 550 mW, about 400 mW to about 600 mW, about 450 mW to about 500 mW, about 450 mW to about 550 mW, about 450 mW to about 600 mW, about 500 mW to about 550 mW, about 500 mW to about 600 mW, or about 550 mW to about 600 mW.

In some embodiments, a high powered near-infrared light source has a radiant flux (power) of, e.g., about 100 mW, about 200 mW, about 300 mW, about 400 mW, about 500 mW, about 600 mW, about 700 mW, about 800 mW, about 900 mW, or about 1000 mW. In some embodiments, a high powered near-infrared light source has a radiant flux (power) of, e.g., at least 100 mW, at least 200 mW, at least 300 mW, at least 400 mW, at least 500 mW, at least 600 mW, at least 700 mW, at least 800 mW, at least 900 mW, or at least 1000 mW. In some embodiments, a high powered near-infrared light source has a radiant flux (power) of, e.g., at most 100 mW, at most 200 mW, at most 300 mW, at most 400 mW, at most 500 mW, at most 600 mW, at most 700 mW, at most 800 mW, at most 900 mW, or at most 1000 mW. In some embodiments, a high powered near-infrared light source has a radiant flux (power) of, e.g., about 100 mW to about 200 mW, about 100 mW to about 300 mW, about 100 mW to about 400 mW, about 100 mW to about 500 mW, about 100 mW to about 600 mW, about 100 mW to about 700 mW, about 100 mW to about 800 mW, about 100 mW to about 900 mW, about 100 mW to about 1000 mW, about 200 mW to about 300 mW, about 200 mW to about 400 mW, about 200 mW to about 500 mW, about 200 mW to about 600 mW, about 200 mW to about 700 mW, about 200 mW to about 800 mW, about 200 mW to about 900 mW, about 200 mW to about 1000 mW, about 300 mW to about 400 mW, about 300 mW to about 500 mW, about 300 mW to about 600 mW, about 300 mW to about 700 mW, about 300 mW to about 800 mW, about 300 mW to about 900 mW, about 300 mW to about 1000 mW, about 400 mW to about 500 mW, about 400 mW to about 600 mW, about 400 mW to about 700 mW, about 400 mW to about 800 mW, about 400 mW to about 900 mW, about 400 mW to about 1000 mW, about 500 mW to about 600 mW, about 500 mW to about 700 mW, about 500 mW to about 800 mW, about 500 mW to about 900 mW, about 500 mW to about 1000 mW, about 600 mW to about 700 mW, about 600 mW to about 800 mW, about 600 mW to about 900 mW, about 600 mW to about 1000 mW, about 700 mW to about 800 mW, about 700 mW to about 900 mW, about 700 mW to about 1000 mW, about 800 mW to about 900 mW, about 800 mW to about 1000 mW, or about 900 mW to about 1000 mW.

In some embodiments, a high powered near-infrared light source has a radiant intensity (brightness) of, e.g., about 150 mW/sr, about 200 mW/sr, about 250 mW/sr, about 300 mW/sr, about 350 mW/sr, about 400 mW/sr, about 450 mW/sr, about 500 mW/sr, about 550 mW/sr, about 600 mW/sr, about 650 mW/sr, about 700 mW/sr, or about 750 mW/sr. In some embodiments, a high powered near-infrared light source has a radiant intensity (brightness) of, e.g., at least 150 mW/sr, at least 200 mW/sr, at least 250 mW/sr, at least 300 mW/sr, at least 350 mW/sr, at least 400 mW/sr, at least 450 mW/sr, at least 500 mW/sr, at least 550 mW/sr, at least 600 mW/sr, at least 650 mW/sr, at least 700 mW/sr, or at least 750 mW/sr. In some embodiments, a high powered near-infrared light source has a radiant intensity (brightness) of, e.g., at most 150 mW/sr, at most 200 mW/sr, at most 250 mW/sr, at most 300 mW/sr, at most 350 mW/sr, at most 400 mW/sr, at most 450 mW/sr, at most 500 mW/sr, at most 550 mW/sr, at most 600 mW/sr, at most 650 mW/sr, at most 700 mW/sr, or at most 750 mW/sr. In some embodiments, a high powered near-infrared light source has a brightness range (or radiant intensity) of, e.g., about 150 mW/sr to about 200 mW/sr, about 150 mW/sr to about 300 mW/sr, about 150 mW/sr to about 400 mW/sr, about 150 mW/sr to about 500 mW/sr, about 150 mW/sr to about 600 mW/sr, about 150 mW/sr to about 700 mW/sr, about 150 mW/sr to about 800 mW/sr, about 200 mW/sr to about 300 mW/sr, about 200 mW/sr to about 400 mW/sr, about 200 mW/sr to about 500 mW/sr, about 200 mW/sr to about 600 mW/sr, about 200 mW/sr to about 700 mW/sr, about 200 mW/sr to about 800 mW/sr, about 300 mW/sr to about 400 mW/sr, about 300 mW/sr to about 500 mW/sr, about 300 mW/sr to about 600 mW/sr, about 300 mW/sr to about 700 mW/sr, about 300 mW/sr to about 800 mW/sr, about 400 mW/sr to about 500 mW/sr, about 400 mW/sr to about 600 mW/sr, about 400 mW/sr to about 700 mW/sr, about 400 mW/sr to about 800 mW/sr, about 500 mW/sr to about 600 mW/sr, about 500 mW/sr to about 700 mW/sr, about 500 mW/sr to about 800 mW/sr, about 600 mW/sr to about 700 mW/sr, about 600 mW/sr to about 800 mW/sr, or about 700 mW/sr to about 800 mW/sr.

In some embodiments, near-infrared light source 170 is a low powered infrared light source. In some embodiments, a low powered near-infrared light source has a radiant flux (power) of, e.g., about 30 mW, about 35 mW, about 40 mW, about 45 mW, about 50 mW, about 55 mW, about 60 mW, about 65 mW, about 70 mW, or about 75 mW. In some embodiments, a low powered near-infrared light source has a radiant flux (power) of, e.g., at least 30 mW, at least 35 mW, at least 40 mW, at least 45 mW, at least 50 mW, at least 55 mW, at least 60 mW, at least 65 mW, at least 70 mW, or at least 75 mW. In some embodiments, a low powered near-infrared light source has a radiant flux (power) of, e.g., at most 30 mW, at most 35 mW, at most 40 mW, at most 45 mW, at most 50 mW, at most 55 mW, at most 60 mW, at most 65 mW, at most 70 mW, or at most 75 mW. In some embodiments, a low powered near-infrared light source has a radiant flux (power) of, e.g., about 30 mW to about 40 mW, about 30 mW to about 50 mW, about 30 mW to about 60 mW, about 30 mW to about 70 mW, about 30 mW to about 75 mW, about 40 mW to about 50 mW, about 40 mW to about 60 mW, about 40 mW to about 70 mW, about 40 mW to about 75 mW, about 50 mW to about 60 mW, about 50 mW to about 70 mW, about 50 mW to about 75 mW, about 60 mW to about 70 mW, or about 60 mW to about 75 mW.

In some embodiments, a low powered near-infrared light source is configured to have a radiant intensity (brightness) of, e.g., about 25 mW/sr, about 50 mW/sr, about 75 mW/sr, about 100 mW/sr, about 125 mW/sr, or about 150 mW/sr. In some embodiments, a low powered near-infrared light source has a brightness (or radiant intensity) of, e.g., at least 25 mW/sr, at least 50 mW/sr, at least 75 mW/sr, at least 100 mW/sr, at least 125 mW/sr, or at least 150 mW/sr. In some embodiments, near-infrared light source 170 has a radiant intensity (brightness) of, e.g., at most 25 mW/sr, at most 50 mW/sr, at most 75 mW/sr, at most 100 mW/sr, at most 125 mW/sr, or at most 150 mW/sr. In some embodiments, a low powered near-infrared light source has a radiant intensity (brightness) of, e.g., about 25 mW/sr to about 50 mW/sr, about 25 mW/sr to about 75 mW/sr, about 25 mW/sr to about 100 mW/sr, about 25 mW/sr to about 125 mW/sr, about 25 mW/sr to about 150 mW/sr, about 50 mW/sr to about 75 mW/sr, about 50 mW/sr to about 100 mW/sr, about 50 mW/sr to about 125 mW/sr, about 50 mW/sr to about 150 mW/sr, about 75 mW/sr to about 100 mW/sr, about 75 mW/sr to about 125 mW/sr, about 75 mW/sr to about 150 mW/sr, about 100 mW/sr to about 125 mW/sr, about 100 mW/sr to about 150 mW/sr, or about 125 mW/sr to about 150 mW/sr.

Referring to FIGS. 9-15, photobiomodulation unit 100 also includes one or more sensors 180 configured to detect and collect information on one or more parameters including operational information of a photobiomodulation therapy garment 20, biometric information of the user, or other useful information to ensure proper use and efficacy. Operational information includes, without limitation, positional and safety information of photobiomodulation therapy garment 20. Biometric information includes, without limitation, body measurements and calculations related to the user. Non-limiting examples of a biometric sensor includes a neuro-conductivity sensor, a galvanometric sensor, an oxygen level sensor, a carbon dioxide level sensor, a brain oxygen level sensor, a heart rate sensor, a cortical blood flow sensor, a temperature sensor, an electroencephalogram sensor, or any combination thereof. One or more sensors 180 can also measure, record and analyze and/or transmit the information to controller 200 where measurement, recording and analysis of the information can be performed.

In one or more embodiments, as shown in FIGS. 9, 11, 15, & 16, sensor cover 79 and one or more sensors 180 thereunder or nearby are positioned between second near-infrared light source grouping 172 and fifth near-infrared light source grouping 175. This position of sensor cover 79 places it and one or more sensors 180 thereunder substantially over sagittal plane 320 of the forehead area. In some embodiments, where second near-infrared light source grouping 172 and/or fifth near-infrared light sources grouping 175 is not present, sensor cover 79 and one or more sensors 180 thereunder or nearby can be positioned on photobiomodulation therapy headband 22 at a position configured to place sensor cover 79 substantially on top of sagittal plane 320 when properly donned. In some embodiments, sensor cover 79 and one or more sensors 180 thereunder or nearby are positioned between first near-infrared light source grouping 171 and fourth near-infrared light source grouping 174. In some embodiments, sensor cover 79 and one or more sensors 180 thereunder or nearby are positioned between third near-infrared light source grouping 173 and sixth near-infrared light source grouping 176. In some embodiments, where two sensors 180 require to be spaced apart for proper functioning, one sensor cover 79 and one or more sensors 180 thereunder or nearby are positioned between first near-infrared light source grouping 171 and fourth near-infrared light source grouping 174 (or outside such groups in the direction towards left portion 56) and one sensor cover 79 and one or more sensors 180 thereunder or nearby are positioned between third near-infrared light source grouping 173 and sixth near-infrared light source grouping 176 (or outside such groups in the direction towards right portion 54).

In some embodiments, sensors 180 include a heart rate sensor and a temperature sensor. Referring to FIGS. 9 & 11-14, one or more sensor 180 includes cardiovascular sensor 182 which detects blood pulse, oxygen levels, as well as other cardiovascular characteristics. Referring to FIG. 10, which is a longitudinal cross-section of sensor mounting portion 142, cardiovascular sensor 182 comprises LED light sources 184, 186 and a photodetector 188. Light from LED light sources 184, 186 is shone on blood vessels just under skin surface S; and the portion of light reflected back is captured by photodetector 188. The signal from cardiovascular sensor 182 is transmitted to controller 200 for determining the user's cardiovascular parameters. Similarly, referring to FIGS. 9 & 11-14, one or more sensor 180 includes a temperature sensor 192 which detects skin parameters, such as, e.g., skin temperature, skin density, and skin opaqueness (color). The signal from temperature sensor 192 is transmitted to controller 200 for determining the user's skin parameters.

Photobiomodulation unit 100 can optionally include one or more stimulators 194 configured to administer a brain stimulatory or inhibitory signal. Non-limiting examples of a stimulator include a component that can generate a magnetic field useful for stimulating nerve cells in the brain, such as, e.g., a magnetic material of a material that can be magnetized using an electrical current (an electromagnet). Such a magnetic field generating component can be used to administer a transcranial magnetic stimulation therapy. In some embodiments, one or more stimulators 194 are operationally mounted to electronic circuity connector 162 or sensor liquid wire tube 158 which contains the electronic circuitry needed to establish electrical communication between each of the one or more stimulators 194 and connection terminal 160.

Referring to FIGS. 1, 6 & 7, photobiomodulation therapy garment 20 also includes controller 200. In one or more embodiments, controller 200 includes a housing enclosing an input, a hardware processor, a memory, and an output, and may include one or more of each of these elements. In one or more example embodiments, controller 200 may include a single board computer, a system on a chip, or other similar and/or known computing devices or circuits. The inputs can include one or more USB connectors and/or a short-range wireless device (e.g., a BLUETOOTH module, a Wi-Fi module, or other wireless communications devices or systems) for communicating with an external computer, such as a smart phone, desktop, laptop, tablet, other wearable computing device, server, and the like. Controller 200 can operate autonomously or semi-autonomously, or may read executable software instructions, code, or other information from the memory or a computer-readable medium, or may receive information or instructions via the input from a user, from a healthcare provider, or any another source logically connected to a computer or device, such as another networked computer, server, or artificial intelligence (AI) or machine-learning system. In some embodiments, controller 200 can be remotely accessed and operated by a third-party individual, such as for example a healthcare worker, who can monitor usage of, change operational parameters for, and/or collect data from photobiomodulation therapy garment 20, thereby providing a remote digital healthcare platform that assists a user in receiving the most effective biomodulation therapy. In some embodiments, controller 200 can be a "virtual controller" where access and operation of photobiomodulation therapy garment 20 by controller 200 is via cloud computing elements by either a healthcare provider, or any another source logically connected to a computer or device, such as another networked computer or server or AI or machine learning-based system. Controller 200 can be assessed and operated by pre-programed instructions and/or parameters, real-time instructions and/or parameters, or both.

Controller 200 is programmed to supply an electrical signal which powers each of the one or more near-infrared light sources 170, each of the one or more sensors 180, and each of the one or more stimulators 194. In addition, controller 200 in one or more embodiments is a computing device which is programmed or configured to implement the methods and algorithms which can operationally control each of the one or more near-infrared light sources 170, each of the one or more sensors 180, and each of the one or more stimulators 194. For example, in some embodiments, controller 200 operational controls one or more of the operation times of the one or more near-infrared light sources 170, the fluence level of the one or more near-infrared light sources 170, the irradiance level of the one or more near-infrared light sources 170, whether the one or more near-infrared light sources 170 are operated continuously or pulsed, which one or more of the one or more near-infrared light sources 170 are activated or deactivated, and predetermined dosimetry levels. In addition, controller 200 operationally controls each of the one or more sensors 180 and receives and analyzes information collected from each of the one or more sensors 180. In some embodiments, controller 200 operationally controls one or more of the operation times of the one or more stimulators 194, the power level of the one or more stimulators 194, whether the one or more stimulators 194 are operated continuously or pulsed, which one or more of the one or more stimulators 194 are activated or deactivated, or any combination thereof.

In some embodiments, controller 200 operationally instructs activating one or more infrared light sources 170 on the left side of midsagittal plane 320 and deactivating one or more infrared light sources 170 on the right side of midsagittal plane 320, or vice versa. In some embodiments, controller 200 operationally instructs activating one or more infrared light sources 170 on the left side and right side of midsagittal plane 320 while activating one or more infrared light sources 170 on the left side of midsagittal plane 320 at a higher level of irradiance relative to one or more infrared light sources 170 on the right side of midsagittal plane 320, or vice versa.

In some embodiments, controller 200 dynamically adjusts operational parameters of photobiomodulation therapy garment 20 using information collected from each of the one or more sensors 180, information provided by the user, or information remotely inputted by a third-party individual. Such information input is then processed by controller 200 relative to information stored in an operational database in one or more algorithms, and, based on the analysis performed in comparing collected or provided or inputted with information stored in such a database with the one or more algorithms, operational parameters of the one or more near-infrared light sources 170, each of the one or more sensors 180, and each of the one or more stimulators 194 are adjusted by executable instructions provided controller 200.

For example, cardiovascular sensor 182 obtains cardiovascular parameters from user during operation of photobiomodulation therapy garment 20 and this input information is analyzed against cardiovascular parameters stored in an operational database in order to assess actual cardiovascular parameters and adjust operation of photobiomodulation therapy garment 20 based on the therapy selected by the user or third-party individual. In some embodiments, a detected decrease in heart rate variability by cardiovascular sensor 182 and sent to controller 200 would result in controller 200 providing executable instructions to optimize the pulse wave by increasing the frequency of light emitted from the one or more near-infrared light source 170 in situations where a user or third-party individual has selected an alertness therapy. As an illustration, the initial pulse wave of photobiomodulation therapy garment 20 could be set at 40 Hz and based upon the detected heart rate variability controller 200 would increase the frequency of light emitted from the one or more near-infrared light source 170 to 50 Hz. Continuous monitoring and analysis of heart rate variability by cardiovascular sensor 182 and controller 200 could result in the 50 Hz pulse wave setting being maintained, or increased to 60 Hz or 70 Hz or more in order to establish the proper pulse wave for an alertness therapy being emitted from the one or more near-infrared light source 170. Such dynamic monitoring of heart rate variability by cardiovascular sensor 182 and controller 200 would result in continuous adjustments to the pulse wave in order to achieve optimum pulse wave of the selected alertness therapy.

In some embodiments, a detected increase in heart rate variability by cardiovascular sensor 182 and sent to controller 200 would result in controller 200 providing executable instructions to optimize the pulse wave by decreasing the frequency of light emitted from the one or more near-infrared light source 170 in situations where a user or third-party individual has selected a calmness or relaxation therapy. As an illustration, the initial pulse wave of photobiomodulation therapy garment 20 could be set at 40 Hz and based upon the detected heart rate variability controller 200 would decreasing the frequency of light emitted from the one or more near-infrared light source 170 to 30 Hz. Continuous monitoring and analysis of heart rate variability by cardiovascular sensor 182 and controller 200 could result in the 30 Hz pulse wave setting being maintained, or decreased to 10 Hz or 1 Hz in order to establish the proper pulse wave for a calmness or relaxation therapy being emitted from the one or more near-infrared light source 170. Such dynamic monitoring of heart rate variability by cardiovascular sensor 182 and controller 200 would result in continuous adjustments to the pulse wave in order to achieve optimum pulse wave of the selected calmness or relaxation therapy.

As another example, skin sensor 192 obtains information on skin parameters from a user during operation of photobiomodulation therapy garment 20 and this input information is analyzed against skin information stored in an operational database in order to assess actual skin parameters and adjust operation of photobiomodulation therapy garment 20 based on the therapy selected by the user or third-party individual. In some embodiments, a detected decrease in skin temperature by skin sensor 192 and sent to controller 200 would result in controller 200 providing executable instructions to optimize skin temperature by increasing the irradiance of light emitted from the one or more near-infrared light source 170 in situations where a user or third-party individual has selected an alertness therapy. As an illustration, the initial irradiance of photobiomodulation therapy garment 20 could be set at 250 mW/cm$^2$ and based upon the detected skin temperature controller 200 would increase the irradiance of light emitted from the one or more near-infrared light source 170 to 500 mW/cm$^2$. Continuous monitoring and analysis of skin temperature by skin sensor 192 and controller 200 could result in the 500 mW/cm$^2$ irradiance setting being maintained, or increased to 750 mW/cm$^2$ or 1000 mW/cm$^2$ or more in order to establish the proper skin temperature for an alertness therapy. Such dynamic monitoring of skin temperature by skin sensor 192 and controller 200 would result in continuous adjustments to the irradiance in order to achieve optimum skin temperature of the selected alertness therapy.

In some embodiments, a detected increase in skin temperature by skin sensor 192 and sent to controller 200 would result in controller 200 providing executable instructions to optimize skin temperature by decreasing the irradiance of light emitted from the one or more near-infrared light source 170 in situations where a user or third-party individual has selected a calmness or relaxation therapy. As an illustration, the initial irradiance of photobiomodulation therapy garment 20 could be set at 250 mW/cm$^2$ and based upon the detected skin temperature controller 200 would decrease the irradiance of light emitted from the one or more near-infrared light source 170 to 100 mW/cm$^2$. Continuous monitoring and analysis of skin temperature by skin sensor 192 and controller 200 could result in the 125 mW/cm$^2$ irradiance setting being maintained, or decreased to 75 mW/cm$^2$ or 25 mW/cm$^2$ or less in order to establish the proper skin temperature for a calmness or relaxation therapy. Such dynamic monitoring of skin temperature by skin sensor 192 and controller 200 would result in continuous adjustments to the irradiance in order to achieve optimum skin temperature of the selected calmness or relaxation herapy.

In some embodiments, a detected decrease in skin temperature by skin sensor 192 and sent to controller 200 would result in controller 200 providing executable instructions to optimize skin temperature by increasing the duty cycle of light emitted from the one or more near-infrared light source 170 in situations where a user or third-party individual has selected an alertness therapy. As an illustration, the initial duty cycle of photobiomodulation therapy garment 20 could be set at 50% and based upon the detected skin temperature controller 200 would increase the duty cycle of light emitted from the one or more near-infrared light source 170 to 60%.

Continuous monitoring and analysis of skin temperature by skin sensor 192 and controller 200 could result in the 60% duty cycle setting being maintained, or increased to 75% or more in order to establish the proper skin temperature for an alertness therapy. Such dynamic monitoring of skin temperature by skin sensor 192 and controller 200 would result in continuous adjustments to the duty cycle in order to achieve optimum skin temperature of the selected alertness therapy.

In some embodiments, a detected increase in skin temperature by skin sensor 192 and sent to controller 200 would result in controller 200 providing executable instructions to optimize skin temperature by decreasing the duty cycle of light emitted from the one or more near-infrared light source 170 in situations where a user or third-party individual has selected a calmness or relaxation therapy. As an illustration, the initial duty cycle of photobiomodulation therapy garment 20 could be set at 50% and based upon the detected skin temperature controller 200 would decrease the duty cycle of light emitted from the one or more near-infrared light source 170 to 40%. Continuous monitoring and analysis of skin temperature by skin sensor 192 and controller 200 could result in the 40% duty cycle setting being maintained, or decreased to 25% or less in order to establish the proper skin temperature for an alertness therapy. Such dynamic monitoring of skin temperature by skin sensor 192 and controller 200 would result in continuous adjustments to the duty cycle in order to achieve optimum skin temperature of the selected calmness or relaxation therapy.

In some embodiments, a detected higher skin opacity, indicative skin with higher melanin content, by skin sensor 192 and sent to controller 200 would result in controller 200 providing executable instructions to optimize skin penetration by adjusting the wavelength of light emitted from the one or more near-infrared light source 170, or a combination of wavelengths, in order to provide optimal light penetration for the selected therapy. As an illustration, the initial wavelength of photobiomodulation therapy garment 20 could be set to 900 nm and based upon the detected skin opacity controller 200 would increase the wavelength of light emitted from the one or more near-infrared light source 170 to about 970 nm. Continuous monitoring and analysis of skin opacity by skin sensor 192 and controller 200 could result in the wavelength setting being maintained, or increased to 1000 nm or more in order to establish the proper wavelength penetration into the skin for the selected therapy. Such dynamic monitoring of skin opacity by skin sensor 192 and controller 200 would result in continuous adjustments to the wavelength in order to achieve optimum skin penetration of the selected therapy.

In some embodiments, a detected lower skin opacity, indicative skin with lower melanin content, by skin sensor 192 and sent to controller 200 would result in controller 200 providing executable instructions to optimize skin penetration by adjusting the wavelength of light emitted from the one or more near-infrared light source 170, or a combination of wavelengths, in order to provide optimal light penetration for the selected therapy. As an illustration, the initial wavelength of photobiomodulation therapy garment 20 could be set to 900 nm and based upon the detected skin opacity controller 200 would decrease the wavelength of light emitted from the one or more near-infrared light source 170 to about 810 nm. Continuous monitoring and analysis of skin opacity by skin sensor 192 and controller 200 could result in the wavelength setting being maintained, or decreased to 790 nm or less in order to establish the proper wavelength penetration into the skin for the selected therapy. Such dynamic monitoring of skin opacity by skin sensor 192 and controller 200 would result in continuous adjustments to the wavelength in order to achieve optimum skin penetration of the selected therapy.

In some embodiments, a detected higher skin density, indicative skin with higher fat content, by skin sensor 192 and sent to controller 200 would result in controller 200 providing executable instructions to optimize skin penetration by adjusting the wavelength of light emitted from the one or more near-infrared light source 170 in order to provide optimal light penetration for the selected therapy. As an illustration, the initial wavelength of photobiomodulation therapy garment 20 could be set to 900 nm and based upon the detected skin density controller 200 would increase the wavelength of light emitted from the one or more near-infrared light source 170 to about 970 nm. Continuous monitoring and analysis of skin density by skin sensor 192 and controller 200 could result in the wavelength setting being maintained, or increased to 1000 nm or more in order to establish the proper wavelength penetration into the skin for the selected therapy. Such dynamic monitoring of skin density by skin sensor 192 and controller 200 would result in continuous adjustments to the wavelength in order to achieve optimum skin penetration of the selected therapy.

In some embodiments, a detected lower skin density, indicative skin with lower fat content, by skin sensor 192 and sent to controller 200 would result in controller 200 providing executable instructions to optimize skin penetration by adjusting the wavelength of light emitted from the one or more near-infrared light source 170 in order to provide optimal light penetration for the selected therapy. As an illustration, the initial wavelength of photobiomodulation therapy garment 20 could be set to 900 nm and based upon the detected skin density controller 200 would decrease the wavelength of light emitted from the one or more near-infrared light source 170 to about 810 nm. Continuous monitoring and analysis of skin density by skin sensor 192 and controller 200 could result in the wavelength setting being maintained, or decreased to 790 nm or less in order to establish the proper wavelength penetration into the skin for the selected therapy. Such dynamic monitoring of skin density by skin sensor 192 and controller 200 would result in continuous adjustments to the wavelength in order to achieve optimum skin penetration of the selected therapy.

As another example, information can be provided by a user or a third-party individual during operation of photobiomodulation therapy garment 20 and this input information is either used directly in order to adjust operation of photobiomodulation therapy garment 20 based on the therapy selected by the user, or analyzed against user-defined or third-party individual defined information stored in an operational database in order to adjust operation of photobiomodulation therapy garment 20 based on the selected therapy. As an illustration, the initial therapy of photobiomodulation therapy garment 20 could be set to an alertness therapy and based upon user input (such as, e.g., "still tired" or "feel good") or individual third-party input (based upon, e.g., monitoring of physiological or vital signs of user) controller 200 would adjust the characteristics of the light being emitted from the one or more near-infrared light source 170. Continuous user or individual third-party input into controller 200 would establish the proper light characteristics for the selected alertness therapy. Such dynamic monitoring of user or individual third-party input into controller 200 would result in continuous adjustments to the light characteristics in order to achieve optimum effect of the selected alertness therapy.

As another example, sensor 180 obtains information on mitochondrial functionality from a user during operation of photobiomodulation therapy garment 20 and this input information is analyzed against mitochondrial functionality information stored in an operational database in order to assess actual mitochondrial functionality and adjust operation of photobiomodulation therapy garment 20 based on the therapy selected by the user or third-party individual. As an illustration, the initial therapy of photobiomodulation therapy garment 20 could be set to an alertness therapy and based upon detected mitochondrial functionality (such as, e.g., $NAD^+$ or NADH levels) controller 200 would adjust the characteristics of the light being emitted from the one or more near-infrared light source 170. Continuous monitoring and analysis of skin opacity by sensor 180 and controller 200 would establish the proper light characteristics for the selected alertness therapy being emitted from the one or more near-infrared light source 170. Such dynamic monitoring of mitochondrial functionality by sensor 180 and controller 200 would result in continuous adjustments to the light characteristics in order to achieve optimum skin penetration of the selected alertness therapy.

The adjustments described in the examples in the paragraphs above made by the controller 200, and the processing performed therein on the various types of information, may be performed in conjunction with a machine learning-based framework that applies elements of artificial intelligence (AI) to analyze the information provided as input within models trained on historical or known data, such as that stored in the operational database(s) referenced above, to improve such adjustments to operational parameters of the one or more near-infrared light sources 170, each of the one or more sensors 180, and each of the one or more stimulators 194. The present invention therefore may include such a machine learning-based framework, which may be comprised of multiple elements that perform, either together or as separately-instantiated models, several of the processing aspects performed by the controller 200.

The modeling performed within the machine learning-based framework may comprise many different types of machine learning, and apply many different mathematical approaches to analyzing information and generating outputs that improve outcomes in the continuous adjustments to the operational parameters of the one or more near-infrared light sources 170, each of the one or more sensors 180, and each of the one or more stimulators 194 that are described herein. For example, in some embodiments of the present invention, the machine learning-based framework may be comprised of algorithms that apply techniques of supervised learning, reinforced learning, and other approaches of machine learning and artificial intelligence to further evaluate inputs into the controller 200.

The machine learning-based framework may be comprised of any of several different mathematical approaches. These may include statistical analyses, which are non-deterministic mathematical approaches that enable calculation of probabilities that events will or will not occur. Regression analyses are types of statistical analyses where models are used for estimating the relationships between variables of interest, such as for example a dependent variable and one or more independent variables (often called 'predictors'). This type of machine learning is used to infer causal relationships between the independent and dependent variables, and for prediction and forecasting of outcomes where such causal relationships are impactful on future states for application of the overall modeling being performed. There are many types of regression analyses, such as linear and non-linear regression, and specific approaches such as logistic regression, that enable the use of derived parameters to interpret the importance of maximum values in form of the log-odds when calculating probability values. For example, other types of logistic functions, and other types of regression analyses, may also be utilized to calculate probabilities in the present invention, and are within the scope of the present invention. Other approaches that may be utilized include, but are not limited to, decision trees, random forest classifiers, support vector machines, and probit. It is therefore to be further understood that the present invention, and the present specification, are not to be limited to any one type of mathematical model or statistical process mentioned herein, particularly as to its application in the one or more layers of machine learning.

Modeling within the machine learning-based framework may also include applications of neural networks. Neural networks generally are comprised of nodes, which are computational units having one or more biased input/output connections. Such biased connections act as transfer (or activation) functions that combine inputs and outputs in some way. Nodes are organized into multiple layers that form the neural network. There are many types of neural networks, which are computing systems that "learn" to perform tasks, without being programmed with task-specific rules, based on examples.

Neural networks generally are based on arrays of connected, aggregated nodes (or, "neurons") that transmit signals to each other in the multiple layers over the biased input/output connections. Connections, as noted above, are activation or transfer functions which "fire" these nodes and combine inputs according to mathematical equations or formulas. Different types of neural networks generally have different configurations of these layers of connected, aggregated nodes, but they can generally be described as an input layer, a middle or 'hidden' layer, and an output layer. These layers may perform different transformations on their various inputs, using different mathematical calculations or functions.

Signals are transmitted between nodes over connections, and the output of each node is calculated in a non-linear function that sums all of the inputs to that node. Weight matrices and biases are typically applied to each node, and each connection, and these weights and biases are adjusted as the neural network processes inputs and transmits them across the nodes and connections. These weights represent increases or decreases in the strength of a signal at a particular connection. Additionally, nodes may have a threshold, such that a signal is sent only if the aggregated output at that node crosses that threshold. Weights generally represent how long an activation function takes, while biases represent when, in time, such a function starts; together, they help gradients minimize over time. At least in the case of weights, they can be initialized and change (i.e., decay) over time, as a system learns what weights should be, and how they should be adjusted. In other words, neural networks evolve as they learn, and the mathematical formulas and functions that comprise neural networks design can change over time as a system improves itself.

The application of neural networks within the machine learning-based framework may include instantiations of different networks for different purposes. These include both "production" neural network(s), configured to refine the algorithms performed within the overall modeling framework to generate output data (for example, as adjusted operational parameters of the one or more near-infrared light sources 170, each of the one or more sensors 180, and each of the one or more stimulators 194), and "training" neural network(s), configured to train the production network(s) using improvements on the reasons for prior, historical outcomes that have been learned.

Recurrent neural networks are a name given to types of neural networks in which connections between nodes follow a directed temporal sequence, allowing the neural network to model temporal dynamic behavior and process sequences of inputs of variable length. These types of neural networks are deployed where there is a need for recognizing, and/or acting on, such sequences. As with neural networks generally, there are many types of recurrent neural networks.

Neural networks having a recurrent architecture may also have stored, or controlled, internal states which permit storage under direct control of the neural network, making them more suitable for inputs having a temporal nature. This storage may be in the form of connections or gates which act as time delays or feedback loops that permit a node or connection to retain data that is prior in time for modeling such temporal dynamic behavior. Such controlled internal states are referred to as gated states or gated memory, and are part of long short-term memory networks (LSTMs) and gated recurrent units (GRUs), which are names of different types of recurrent neural network architectures. This type of neural network design is utilized where desired outputs of a system are motivated by the need for memory, as storage, and as noted above, where the system is designed for processing inputs that are comprised of timed data sequences. Examples of such timed data sequences include video, speech recognition, and handwriting—where processing requires an analysis of data that changes temporally. In the present invention, where output data is in the form of operational parameters of the one or more near-infrared light sources 170, each of the one or more sensors 180, and each of the one or more stimulators 194, an understanding of the influence of various events on a state over a period of time lead to more highly accurate and reliable operational parameters that may at least impact an amount of time that stimulation is provided.

Many other types of recurrent neural networks exist. These include, for example, fully recurrent neural networks, Hopfield networks, bi-directional associative memory networks, echo state networks, neural Turing machines, and many others, all of which exhibit the ability to model temporal dynamic behavior. Any instantiation of such neural networks in the present invention may include one or more of these types, and it is to be understood that neural networks applied within the machine learning-based framework may include different ones of such types. Therefore, the present invention contemplates that many types of neural networks may be implemented, depending at least on the type of problem being analyzed Controller 200 reversibly connects to photobiomodulation therapy garment 20 by operationally engaging terminal rail mount 164. Controller 200 may optionally include a rechargeable battery positioned within the housing. Controller 200 can be detached from terminal rail mount 164 for charging the rechargeable battery therein, by using a charging connector, such as USB-C, micro-USB, or the like. Further, the charging connector can provide wired data communication with a remote computer, such as a smart phone, laptop, desktop, or other computer device. In one or more embodiments, this enables tracking of usage, and/or updating or changing operational parameters such as desired dosimetry, duration, pulsed operation, etc., and/or to update the controller firmware, and/or to change the type of photobiomodulation therapy garment 20 to which controller 200 will be attached. Controller 200 can be a universal controller, such that controller 200 can be connected to multiple embodiments of photobiomodulation therapy garment 20, such as photobiomodulation therapy headband 22, a neck region garment, a posterior cervical region garment, a carpal region garment, an abdominal region garment, and the like, each being configured to cover their respective regions when donned.

One or more near-infrared light sources 170 of photobiomodulation unit 100 can be positioned into one or more separate near-infrared light source groupings arranged in a number of intergroup patterns relative to each other and on the one or more regions of interest of skin region S to be treated by the photobiomodulation therapy. For example, there can be, e.g., one near-infrared light source grouping, two near-infrared light source groupings, three near-infrared light source groupings, four near-infrared light source groupings, five near-infrared light source groupings, six near-infrared light source groupings, seven near-infrared light source groupings, eight near-infrared light source groupings, nine near-infrared light source groupings, or ten near-infrared light source groupings. Each near-infrared light source groupings is spaced apart from the neighboring groupings, where the intergroup spacing can be the same between each near-infrared light source grouping or can vary according to the desired dosimetry and vary according to the relative locations of the desired regions of interest. The relative pattern of near-infrared light source groupings is configured to position each grouping on photobiomodulation therapy garment 20 to at least partially cover their respective regions of interest on skin surface S, which may appear to be a random pattern to the casual observer. The spacing of an intergroup pattern between each near-infrared light source grouping can be defined by a column distance d1 and by a row distance d2. The intergroup distance can be measured from the centers of the light sources. In one or more embodiments, column distance d1 and row distance d2 are at least 5 mm, or at least 10 mm, or at least 15 mm, or at least 20 mm, or at least 25 mm, or at least 30 mm, or at least 35 mm, or at least 40 mm. In a rectangular array, row distance d2 can be the same distance or differ from column distance d1.

In some embodiments, photobiomodulation unit 100 of photobiomodulation therapy garment 20 comprise one or more near-infrared light source groupings. Each of the one or more near-infrared light source groupings are positioned in a pattern that is configured to direct each light source to a particular region of interest, when photobiomodulation therapy garment 20 is correctly positioned atop forehead of person P. In some embodiments, photobiomodulation unit 100 comprise one or more near-infrared light source groupings positioned to so that when photobiomodulation therapy garment 20 is properly donned, each of the one or more near-infrared light source groupings is position in a manner that at least partially overlays or is substantially centered on a primary acupuncture meridian, a major extraordinary vessel, a minor extraordinary vessel, or any combination thereof. A primary acupuncture meridian includes, without limitation, a heart meridian, a pericardium meridian, a lung meridian, a spleen meridian, a liver meridian, a kidney meridian, a small intestine meridian, a large intestine meridian, a triple energizer meridian, a stomach meridian, a gallbladder meridian, and a bladder meridian. A major extraordinary vessel includes, without limitation, a conception vessel and a governing vessel. A minor extraordinary vessel, a penetrating vessel, a girdling vessel, a yin linking vessel, a yin motility vessel, a yang linking vessel, and a yang motility vessel.

In some embodiments, and as shown in FIGS. 3, 9, 11, 12, 15, & 16, photobiomodulation unit 100 comprises six near-infrared light source groupings, namely first near-infrared light source grouping 171, second near-infrared light source grouping 172, third near-infrared light source grouping 173, fourth near-infrared light source grouping 174, fifth near-infrared light source grouping 175, and sixth near-infrared light source grouping 176. In some embodiments, and referring to FIGS. 3, 15, 16, but also FIGS. 9 & 11, near-infrared light source groupings 171, 172, 173, 174, 175, 176 of near-infrared light sources 170 present on photobiomodulation unit 100 are arranged in a rectangular array pattern, with three columns and two rows, with each near-infrared light source grouping separated by column distance d1 and row distance d2. In these embodiments, near-infrared light source groupings 171, 172, 173, 174, 175, 176 are positioned in a pattern that is configured to direct each light source to a particular region of interest, when photobiomodulation therapy headband 22 is correctly positioned atop forehead of person P. For example, in some embodiments, near-infrared light source groupings 171, 172, 173, 174, 175, 176 are configured into photobiomodulation therapy headband 22 so that when donned atop forehead of person P, photobiomodulation therapy headband 22 is substantially positioned above superciliary arch region 322 in a manner that positions first, second, third, fourth, fifth and sixth near-infrared light source groupings 171, 172, 173, 174, 175, 176 at least above eye sockets of person P. In some embodiments, each of near-infrared light source groupings 171, 172, 173, 174, 175, 176 are positioned so that when photobiomodulation therapy headband 22 is properly donned, first near-infrared light source grouping 171 of near-infrared light source 170 is located in a first position that at least partially overlays or is substantially centered on Fp1 site 300, second near-infrared light source grouping 172 of near-infrared light source 170 is located in a second position that at least partially overlays or is substantially centered on Fpz site 302, third near-infrared light source grouping 173 of near-infrared light source 170 is located in a third position that at least partially overlays or is substantially centered on Fp2 site 304, fourth near-infrared light source grouping 174 of near-infrared light source 170 is located in a fourth position that at least partially overlays or is substantially centered on F3 site 306, fifth near-infrared light source grouping 175 of near-infrared light source 170 is located in a fifth position that at least partially overlays or is substantially centered on Fz site 308, and sixth near-infrared light source grouping 176 of near-infrared light source 170 is located in a sixth position that at least partially overlays or is substantially centered on F4 site 310.

In some embodiments, and as shown in FIG. 12, photobiomodulation unit 100 comprises six near-infrared light source groupings of near-infrared light source 170, namely first near-infrared light source grouping 171, second near-infrared light source grouping 172, third near-infrared light source grouping 173, fourth near-infrared light source grouping 174, fifth near-infrared light source grouping 175, and sixth near-infrared light source grouping 176. The six near-infrared light source groupings are organized into two inverse triangles with first, second, third, and fourth near-infrared light source groupings 171, 172, 173, 174 aligned in an upper row, and fifth and sixth near-infrared light source groupings 175, 176 aligned in a lower row. First and second near-infrared light source groupings 171, 172 are positioned to cover a region containing sites F3 306 and Fz 308 of head H and third and fourth light groupings 173, 174 are positioned to cover a region containing site Fz 308 and F4 310 of head H. Fifth near-infrared light source grouping 175 is positioned to cover a region containing sites Fp1 300 and sixth near-infrared light source grouping 176 is positioned to cover a region containing sites Fp2 304. In these embodiments, one or more sensors 180 positioned in the lower row in between fifth and sixth near-infrared light source groupings 175, 176.

In some embodiments, and as shown in FIG. 13, photobiomodulation unit 100 comprises five near-infrared light source groupings of near-infrared light source 170, namely first near-infrared light source grouping 171, second near-infrared light source grouping 172, third near-infrared light source grouping 173, fourth near-infrared light source grouping 174, and fifth near-infrared light source grouping 175. First, second, and third near-infrared light source groupings 171, 172, 173, are aligned in an upper row, and fourth and fifth near-infrared light source groupings 174, 175 aligned in a lower row, with fourth near-infrared light source grouping 174 located below first near-infrared light source grouping 171 and fifth near-infrared light source grouping 175 located below third near-infrared light source grouping 173. First, second and third near-infrared light source groupings 171, 172, 173 are positioned to cover a region containing sites F3 306, Fz 308 and F4 310 of head H. Fourth near-infrared light source grouping 174 is positioned to cover a region containing sites Fp1 300 and fifth near-infrared light source grouping 175 is positioned to cover a region containing sites Fp2 304. In these embodiments, one or more sensors 180 are located in the lower row and are positioned below second near-infrared light source grouping 172 and in between fourth near-infrared light source grouping 174 and fifth near-infrared light source grouping 175.

In some embodiments, and as shown in FIG. 14, photobiomodulation unit 100 comprises three near-infrared light source groupings of near-infrared light source 170, namely first near-infrared light source grouping 171, second near-infrared light source grouping 172, and third near-infrared light source grouping 173. First, second, and third near-infrared light source groupings 171, 172, 173, are aligned in a row and are positioned to cover a region containing sites F3 306, Fz 308 and F4 310 of head H. In these embodiments, one or more sensors 180 are positioned below second near-infrared light source grouping 172.

In some embodiments, each of near-infrared light source groupings comprises a single light near-infrared light source 170. For example, and as shown in FIGS. 11-14 & 16, each of near-infrared light source groupings 171, 172, 173, 174, 175, 176 of photobiomodulation unit 100 comprises a single light near-infrared light source 170. In embodiments where only a single light near-infrared light source 170 is present in a near-infrared light source grouping, such near-infrared light source 170 is preferably a high-powered near-infrared light source having a radiant intensity (brightness) range of about 150 mW/sr or more, and more preferably about 250 mW/sr or more.

In some embodiments, each of near-infrared light source groupings comprises a plurality light near-infrared light sources 170. For example, and as shown in FIGS. 9 & 15, each of near-infrared light source groupings 171, 172, 173, 174, 175, 176 of photobiomodulation unit 100 comprises nine light near-infrared light sources 170. In embodiments where a plurality light near-infrared light sources 170 is present in a near-infrared light source grouping, such near-infrared light source 170 can all be low-powered near-infrared light source having a radiant intensity (brightness) range of 125 mW/sr or less. In other embodiments where a plurality light near-infrared light sources 170 is present in a near-infrared light source grouping, such near-infrared light source 170 can all be a combination of both high-powered near-infrared light source having a radiant intensity (brightness) range of about 150 mW/sr or more, and more preferably about 250 mW/sr or more and low-powered near-infrared light source having a radiant intensity (brightness) range of 125 mW/sr or less.

Additionally, in embodiments where a near-infrared light source grouping comprises a plurality light near-infrared light sources 170, there is an intragroup spacing between each individual near-infrared light source 170 and the neighboring near-infrared light sources 170 within the same group. The intragroup spacing of each near-infrared light source 170 of an a near-infrared light intragrouping can be the same between each individual near-infrared light source 170 or can vary according to the desired dosimetry and vary according to the relative locations of the desired regions of interest. In some embodiments, each individual near-infrared light source 170 of each of near-infrared light source grouping is arranged in a pattern configured for desired therapeutic effect, with each individual near-infrared light source 170 being randomly relative to the other individual near-infrared light sources 170 within the same near-infrared light source group, and/or in a pattern determined by a combination of factors including a desired therapeutic effect, cost, manufacturing capabilities, and so on. The relative pattern of near-infrared light source groupings is configured to position each near-infrared light source 170 on photobiomodulation therapy garment 20 to at least partially cover their respective regions of interest on skin surface S, which may appear to be a random pattern to the casual observer.

Each individual near-infrared light source 170 within a near-infrared light intragrouping is spaced from all other individual near-infrared light sources 170 within the same intragrouping by an intragroup light source spacing. Each near-infrared light source 170 in a near-infrared light intragrouping can be arranged in a pattern that matches the location of multiple regions of interest on skin surface S. Thus, the resulting near-infrared light intragrouping can seemingly be arranged in irregular patterns that correspond to the location of multiple regions of interest on skin surface S, where each can be simultaneously at least partially covered by a corresponding grouping. As a result, the intergroup spacing and relative positioning of each near-infrared light source 170 in a near-infrared light intragrouping can vary according to the locations of the regions of interest on skin surface S.

In some embodiments, for example in a rectangular arrangement as shown in FIG. 3, the spacing between each near-infrared light source 170 of a near-infrared light intragrouping can be defined by a column spacing d3 and by a row spacing d4. The intragroup spacing can be measured from the centers of the near-infrared light source 170. In some embodiments, column spacing d3 and row spacing d4 are at least 2 mm, at least 3 mm, at least 4 mm, at least 5 mm, at least 6 mm, at least 7 mm, at least 8mm, at least 9 mm, at least 10 mm, at least 12 mm, or at least 15 mm. In a rectangular array, row spacing d3 can be the same distance or differ from column spacing d4. In such rectangular arrangement, each near-infrared light source 170 of a near-infrared light intragrouping is arranged in a n1×n2 array, where n1 and n2 each represent the number of individual near-infrared light sources 170 in a row and column, respectively. For example, an infrared light intragrouping can be a 2×2 array, a 2×3 array, a 3×2 array, a 3×3 array, a 3×4 array, a 4×3 array, a 4×4 array, a 2×5 array, a 5×2 array, a 3×5 array, a 5×3 array, a 4×5 array, a 5×4 array, a 5×5 array, and so on. In some embodiments, each near-infrared light source 170 of a near-infrared light intragrouping can be configured as a radial or circular array about a single circle or multiple concentric circles. In these embodiments, an intergroup spacing can be measured from the centers of the light sources.

In some embodiments, each of near-infrared light source of photobiomodulation therapy garment 20 is configured as near-infrared light intragrouping comprising a plurality of near-infrared light sources 170 arranged in an intragroup array. In some embodiments, near-infrared light source groups 171, 172, 173, 174, 175, 176 of photobiomodulation therapy garment 20 are each configured as near-infrared light intragrouping comprising a plurality of near-infrared light sources 170 arranged in an intragroup array, with first near-infrared light source group 171 comprising a plurality of near-infrared light sources 170 arranged in a first near-infrared light intragrouping, second near-infrared light source group 172 comprising a plurality of near-infrared light sources 170 arranged in a second near-infrared light intragrouping, third near-infrared light source group 173 comprising a plurality of near-infrared light sources 170 arranged in a third near-infrared light intragrouping, fourth near-infrared light source group 174 comprising a plurality of near-infrared light sources 170 arranged in a fourth near-infrared light intragrouping, fifth near-infrared light source group 175 comprising a plurality of near-infrared light sources 170 arranged in a fifth near-infrared light intragrouping, and sixth near-infrared light source group 176 comprising a plurality of near-infrared light sources 170 arranged in a sixth near-infrared light intragrouping.

In some embodiments, and referring to FIGS. 3, 9, & 12, near-infrared light source groupings 171, 172, 173, 174, 175, 176 of photobiomodulation therapy headband 22 are each configured as near-infrared light intragrouping comprising nine near-infrared light sources 170 arranged in a 3×3 array of three columns and three rows. In this example, d3 is greater than d4, which can create therapeutic benefits due to the combined and overlapping light patterns incident on skin surface S surface, as well as strategic gaps or areas of lesser overlap of light patterns. In the illustrated example embodiment, d3=6 mm to 7 mm and d4=9 mm to 10 mm. The overlapping pattern of incident light creates regions of varying power levels incident on skin surface S within and around each array or grouping, with areas of maximum irradiance and fluence immediately beneath each individual near-infrared light source 170, areas of lesser irradiance and fluence between closely situated individual near-infrared light sources 170, and areas of least irradiance and fluence between individual near-infrared light sources 170 situated furthest from one another. Additionally, although each near-infrared light intragrouping of near-infrared light source groupings 171, 172, 173, 174, 175, 176 is each illustrated as having the same intragroup pattern, each intragroup pattern can be configured with differing patterns and numbers of individual near-infrared light sources 170, which can be determined based on the desired form of therapy and the dosimetry required for each region of interest.

In one or more embodiments, in operation, groupings of near-infrared light sources can all be activated by controller 200 using the same operational parameters (e.g., all groupings simultaneously activated, all in pulsed mode, and all with the same power settings). In one or more embodiments, in operation, groupings of near-infrared light sources can each be activated by controller 200 with differing operational parameters, where one or more selected groupings may be activated, while other groupings remain off. Further, in one or more embodiments, controller 200 has capabilities to control the power level and/or pulsed/continuous operation for each grouping of near-infrared light sources independent of other groupings of near-infrared light sources on photobiomodulation therapy garment 20. There is a great deal of flexibility in operational parameters available. Not only can each individual grouping of near-infrared lights be individually operated, each individual near-infrared light source 170 in each grouping of near-infrared lights can be individually addressed and controlled using individual operating parameters. In this way, each individual near-infrared light source 170 can be individually addressable as a unit such that each can activated/turned on or deactivated/turned off independent of all other individual near-infrared light sources 170. Further, in one or more embodiments, each individual near-infrared light source 170 can be actuated in a pulsed or continuous mode independent of all other individual near-infrared light sources 170. Additionally, in one or more embodiments, each individual near-infrared light source 170 can be actuated using a power profile independent of all other individual light sources. In this way, a number of predefined patterns can be initiated via executable instructions from controller 200, where the patterns of activated light sources can change according to the desired therapeutic effect and location of regions of interests.

Looking now at FIGS. 8, 15 & 16, in some embodiments, photobiomodulation therapy garment 20 is assembled by sandwiching photobiomodulation unit 100 between outer fabric sheet 40 and inner fabric sheet 70. In some embodiments, and as shown in FIG. 8, a hot melt adhesive film 210, sized and shaped to cover a substantial portion or all of flexible printed circuit board assembly 110, but not to cover terminal rail mount 164 of connection terminal 160, is positioned between outer fabric sheet 40 and photobiomodulation unit 100. In some embodiments, and as shown in FIGS. 15 & 16, liquid wire circuit assembly 150 is affixed directly to outer fabric sheet 40, e.g., by using an adhesive or weaving into outer fabric sheet 40. In embodiments where photobiomodulation unit 100 comprises flexible printed circuit board assembly 110, photobiomodulation unit 100 is aligned to outer fabric sheet 40 in a manner that allows terminal rail mount 164 of connection terminal 160 to be inserted through terminal rail mount opening 58. In embodiments where photobiomodulation unit 100 comprises liquid wire circuit assembly 150, connection terminal 160 is affixed to outer fabric sheet 40 during construction of liquid wire circuit assembly 150 onto outer fabric sheet 40.

Still referring to FIGS. 8, 15 & 16, once photobiomodulation unit 100 is position on outer fabric sheet 40, a layer of double-sided tape 220, sized and shaped to cover a substantial portion or all of photobiomodulation unit 100, is positioned between photobiomodulation unit 100 and inner fabric sheet 70. Double-sided tape 220 includes one or more near infrared light source openings 222 and one or more sensor openings 224, each being cutouts configured to provide clearance for their respective components, such that double-sided tape 220 does not interfere with the operation of the one or more near-infrared light sources 170 and one or more sensors 180. If present, sensor cover 79 is properly positioned over its corresponding sensor 180. Inner fabric sheet 70 is then aligned with outer fabric sheet 40 and photobiomodulation unit 100 and positioned so that each of the one or more near-infrared light sources 170 and each of the one or more sensors 180 is properly positioned with their corresponding near infrared light source opening 76 and sensor opening 78 thereby permitting proper functioning of these components. Inner fabric sheet 70 can then be secured to outer fabric sheet 40 by sewing the edges of inner fabric sheet 70 to outer fabric sheet 40.

A photobiomodulation therapy garment disclosed herein is useful in providing a photobiomodulation therapy, including a transcranial photobiomoculation therapy. Such non-invasive light-based neuromodulation treatment requires no medication and provides long-lasting benefits by changing how a user's brain works from the neuron-level up by providing a variety of positive photochemical reactions. For example, a photobiomodulation therapy can increase neuronal mitochondria energy and adenosine triphosphate (ATP) production resulting in increased production of cellular energy. In addition, transfer of light energy can also trigger reactive oxygen species (ROS) production, which can regulate cellular and tissue-level inflammation and improve cellular repair and healing, and nitric oxide (NO) production which is critical for good blood vessel health and optimal blood flow, nutrient delivery and waste removal. This is important as inadequate cerebral blood flow and circulation can make the brain experience fuzzy memory, forgetfulness, poor concentration and even dementia. Enhanced cellular energy and increased cerebral blood flow result in increased neurogenesis and neuronal plasticity, increased neuroprotection, enhanced neural repair, and reduced inflammation. In addition, such photobiomodulation therapy provides both calming and relaxation benefits as well as improved focus and performance resulting in enhanced mental productivity, mental wellbeing and overall cognitive function.

In some embodiments, a photobiomodulation therapy garment disclosed herein is used as the sole therapeutic device. In some embodiments, a photobiomodulation therapy garment disclosed herein is used in conjunction with another therapy. In some embodiments, a photobiomodulation therapy garment disclosed herein is used in conjunction with another cognitive behavioral therapy.

In some embodiments, a photobiomodulation therapy garment disclosed herein is used in conjunction with another photobiomodulation therapy, such as, e.g., a high-power irradiance photobiomodulation therapy. In some embodiments, an individual undergoes a high-power transcranial photobiomodulation therapy using a stationary device capable of administering an irradiance of about 250 mW/cm$^2$ or more in conjunction with a low-power transcranial photobiomodulation therapy using a photobiomodulation therapy garment disclosed herein capable of administering an irradiance of about 55 mW/cm$^2$ or less. In some embodiments, a high-power photobiomodulation therapy is conducted in in a clinical or other healthcare facility setting while a low-power photobiomodulation therapy is conducted in a non-clinical setting, such as, e.g., at home, in a park, or when traveling in a vehicle. In some embodiments, a low-power transcranial photobiomodulation therapy is used to augment the effectiveness of a high-power transcranial photobiomodulation therapy and improve the treatment depression and depressive symptoms in the individual. In some embodiments, a circadian-based timing administration disclosed herein would be used to time the administration of a high-power transcranial photobiomodulation therapy, a low-power transcranial photobiomodulation therapy, or both.

In some embodiments, a photobiomodulation therapy garment disclosed herein is used in conjunction with transcranial magnetic stimulation (TMS). In some embodiments, an individual undergoes a TMS in conjunction with a low-power transcranial photobiomodulation therapy using a photobiomodulation therapy garment disclosed herein capable of administering an irradiance of about 20 mW/cm$^2$ to about 500 mW/cm$^2$. In some embodiments, a TMS is conducted in a clinical or other healthcare facility setting while a low-power photobiomodulation therapy is conducted in a non-clinical setting, such as, e.g., at home, in a park, or when traveling in a vehicle. In some embodiments, a low-power transcranial photobiomodulation therapy is used to augment the effectiveness of a TMS and improve the treatment depression and depressive symptoms in the individual. In some embodiments, a circadian-based timing administration disclosed herein would be used to time the administration of a TMS, a low-power transcranial photobiomodulation therapy, or both.

In some embodiments, a photobiomodulation therapy garment disclosed herein is used in conjunction with an evidence-based mental health practice. In some embodiments, an individual undergoes an evidence-based mental health practice in conjunction with a low-power transcranial photobiomodulation therapy using a photobiomodulation therapy garment disclosed herein capable of administering an irradiance of about 55 mW/cm$^2$ or less. An evidence-based mental health practice includes, without limitation, Evidence Based Psychotherapy (EBT), Cognitive Behavioral Therapy (CBT), Dialectical Behavioral Therapy (DBT), Exposure Therapy, Functional Family Therapy (FFT), Assertive Community Treatment (ACT), Acceptance and Commitment Therapy (ACT), Prolonged Exposure Therapy (PE), Cognitive Training and Rehab, and Motivational Interviewing (MI). In some embodiments, an evidence-based mental health practice is conducted by a therapist in a clinical or other healthcare facility setting while the low-power photobiomodulation therapy is conducted in a non-clinical setting, such as, e.g., at home, in a park, or when traveling in a vehicle. In some embodiments, an evidence-based mental health practice is conducted by a therapist in a virtual setting while the low-power photobiomodulation therapy is conducted in a non-clinical setting, such as, e.g., at home, in a park, or when traveling in a vehicle. In some embodiments, an evidence-based mental health practice is a digital-based Artificial Intelligence (AI) therapy while the low-power photobiomodulation therapy is conducted in a non-clinical setting, such as, e.g., at home, in a park, or when traveling in a vehicle. In some embodiments, a low-power transcranial photobiomodulation therapy is used to augment the effectiveness of an evidence-based mental health practice and improve the treatment depression and depressive symptoms in the individual. In some embodiments, a circadian-based timing administration disclosed herein would be used to time the administration of an evidence-based mental health practice, a low-power transcranial photobiomodulation therapy, or both.

In some embodiments, a photobiomodulation therapy garment disclosed herein is used in conjunction with an ocular light therapy, such as, e.g., a bright light therapy or blue light therapy. In some embodiments, an individual undergoes an ocular light therapy in conjunction with a transcranial photobiomodulation therapy using a photobiomodulation therapy garment disclosed herein capable of administering an irradiance of about 20 mW/cm$^2$ to about 500 mW/cm$^2$. In some embodiments, a transcranial photobiomodulation therapy can be administered on a daily basis during an ocular light therapy and/or between each of two or more ocular light therapies. In some embodiments, the transcranial photobiomodulation therapy is used to augment the effectiveness of an ocular light therapy by enhancing relaxation, calmness, and well-being. In some embodiments, a circadian-based timing administration disclosed herein would be used to time the administration of an ocular light therapy, a transcranial photobiomodulation therapy, or both.

In some embodiments, a photobiomodulation therapy garment disclosed herein is used in conjunction with a mindfulness therapy. In some embodiments, an individual practices a mindfulness therapy in conjunction with a transcranial photobiomodulation therapy using a photobiomodulation therapy garment disclosed herein capable of administering an irradiance of about 20 mW/cm$^2$ to about 300 mW/cm$^2$. In some embodiments, a transcranial photobiomodulation therapy can be administered on a daily basis during a mindfulness therapy and/or between each of two or more mindfulness therapies. In some embodiments, a transcranial photobiomodulation therapy is used to augment the effectiveness of a mindfulness therapy by enhancing relaxation, calmness, and well-being. In some embodiments, a circadian-based timing administration disclosed herein would be used to time the administration of a mindfulness therapy, a transcranial photobiomodulation therapy, or both.

In some embodiments, a photobiomodulation therapy garment disclosed herein is used in conjunction with a meditative therapy. In some embodiments, an individual practices a meditative therapy in conjunction with a transcranial photobiomodulation therapy using a photobiomodulation therapy garment disclosed herein capable of administering an irradiance of about 20 mW/cm$^2$ to about 300 mW/cm$^2$. In some embodiments, a transcranial photobiomodulation therapy can be administered on a daily basis during a meditative therapy and/or between each of two or more meditative therapies. In some embodiments, a transcranial photobiomodulation therapy is used to augment the effectiveness of a meditative therapy by enhancing relaxation, calmness, and well-being. In some embodiments, a circadian-based timing administration disclosed herein would be used to time the administration of a meditative therapy, a transcranial photobiomodulation therapy, or both.

In some embodiments, a photobiomodulation therapy using a photobiomodulation therapy garment disclosed herein, whether alone or in conjunction with another therapy, is administered based on a circadian rhythm of an individual. In some embodiments, an individual undergoes a transcranial photobiomodulation therapy using a photobiomodulation therapy garment disclosed herein in the morning hours, such as, e.g., between 6:00 am and 10:00 am. In some embodiments, an individual undergoes a transcranial photobiomodulation therapy using a photobiomodulation therapy garment disclosed herein in the afternoon/early evening hours, such as, e.g., between 3:00 pm and 7:00 pm. A photobiomodulation therapy garment disclosed herein capable of administering an irradiance of about 20 mW/cm$^2$ to about 500 mW/cm$^2$ would be used in such a circadian-based timing administration. In some embodiments, a circadian-based timing administration would be useful for the treatment depression and depressive symptoms in the individual.

Aspects of the present specification may also be described by the following embodiments:

1. A photobiomodulation therapy garment worn atop a skin surface having a region of interest, the photobiomodulation therapy garment comprising a flexible outer sheet; a flexible inner sheet having a portion to permit passage of near-infrared light therethrough, the inner sheet being configured to face the skin surface; a flexible circuit board positioned between the outer sheet and the inner sheet; a near-infrared light source mounted on the flexible circuit board and aligned with the portion of the flexible inner sheet, the near-infrared light source configured to emit near-infrared light at a wavelength between 600 nm to 1600 nm and at a predetermined dosimetry directed at the region of interest on the skin surface during a photobiomodulation treatment; and a controller having a processor and a memory, the controller being in electrical communication with the near-infrared light source through the flexible circuit board, the processor and the memory configured with executable instructions for controlling one or more of a light source operation time, a light source fluence level, a light source irradiance level, a light source pulsed operation, and a light source continuous operation.

2. The photobiomodulation therapy garment of embodiment 1 wherein the near-infrared light source is part of a grouping of near-infrared light sources arranged on the flexible circuit board and configured to be directed at the region of interest on the skin surface during the photobiomodulation treatment.

3. The photobiomodulation therapy garment of embodiments 1 or 2 wherein the grouping of near-infrared light sources are arranged with an intragroup light source spacing of at least 2 mm therebetween, or at least 3 mm therebetween, or at least 4 mm therebetween, or at least 5 mm therebetween, or at least 6 mm therebetween, or at least 7 mm therebetween, or at least 8 mm therebetween, or at least 9 mm therebetween, or at least 10 mm therebetween.

4. The photobiomodulation therapy garment of any one of embodiments 1-3 wherein the region of interest is one of an Fp1 site, an Fpz site, an Fp2 site, an F3 site, an Fz site, and an F4 site, a posterior cervical site, a carpal site, and an abdominal site, the grouping of the near-infrared light sources is configured to at least partially overlay the region of interest.

5. The photobiomodulation therapy garment of any one of embodiments 1-4 wherein a sensor is configured to detect one or more parameters indicative of a position and thereafter transmit a position signal to the controller so that the position on the skin surface can be determined.

6. The photobiomodulation therapy garment of any one of embodiments 1-5 wherein the grouping of near-infrared light sources is configured to at least partially overlay an Fp1 site, a second grouping of near-infrared light sources is configured to at least partially overlay an Fpz site, a third grouping of near-infrared light sources is configured to at least partially overlay an Fp2 site, a fourth grouping of near-infrared light sources is configured to at least partially overlay an F3 site, a fifth grouping of near-infrared light sources is configured to at least partially overlay an Fz site, a sixth grouping of near-infrared light sources is configured to at least partially overlay an F4 site.

7. The photobiomodulation therapy garment of any one of embodiments 1-6 wherein a sensor is configured to detect one or more parameters indicative of a position and thereafter transmit a position signal to the controller so that the position on the skin surface can be determined, the sensor is positioned between the second grouping of near-infrared light sources and the fifth grouping of near-infrared light sources.

8. The photobiomodulation therapy garment of any one of embodiments 1-7 wherein each of the grouping of near-infrared light sources, the second grouping of near-infrared light sources, the third grouping of near-infrared light sources, the fourth grouping of near-infrared light sources, the fifth grouping of near-infrared light sources, and the sixth grouping of near-infrared light sources are minimally separated from one another by an intergroup light source spacing that is greater than 5 mm, or that is greater than 10 mm, or that is greater than 15 mm, or that is greater than 20 mm, or that is greater than 25 mm, or that is greater than 30 mm.

9. The photobiomodulation therapy garment of any one of embodiments 1-8 wherein the grouping of near-infrared light sources is arranged in a first 3×3 array.

10. The photobiomodulation therapy garment of any one of embodiments 1-9 further comprising a second grouping of near-infrared light sources arranged in a second 3×3 array, a third grouping of near-infrared light sources arranged in a third 3×3 array, a fourth grouping of near-infrared light sources arranged in a fourth 3×3 array, a fifth grouping of near-infrared light sources arranged in a fifth 3×3 array, and a sixth grouping of near-infrared light sources arranged in a sixth 3×3 array.

11. The photobiomodulation therapy garment of any one of embodiments 1-10 wherein each of the first 3×3 array, the second 3×3 array, the third 3×3 array, the fourth 3×3 array, the fifth 3×3 array, and the sixth 3×3 array are minimally separated from one another by an intergroup light source spacing that is greater than 5 mm, or that is greater than 10 mm, or that is greater than 15 mm, or that is greater than 20 mm, or that is greater than 25 mm, or that is greater than 30 mm.

12. The photobiomodulation therapy garment of any one of embodiments 1-11 wherein each of the first 3×3 array, the second 3×3 array, the third 3×3 array, the fourth 3×3 array, the fifth 3×3 array, and the sixth 3×3 array are minimally separated from one another by an intergroup light source spacing sufficient to prevent substantial light bleed therebetween.

13. The photobiomodulation therapy garment of any one of embodiments 1-12 wherein the region of interest is one or more of an Fp1 site, an Fpz site, an Fp2 site, an F3 site, an Fz site, an F4 site, a posterior cervical site, a carpal site, and an abdominal site on the skin surface.

14. The photobiomodulation therapy garment of any one of embodiments 1-13 wherein the near-infrared light source is configured to emit near-infrared light directed to an Fp1 site, a second near-infrared light source is configured to emit near-infrared light directed to an Fpz site, third near-infrared light source is configured to emit near-infrared light directed to an Fp2 site, a fourth near-infrared light source is configured to emit near-infrared light directed to an F3 site, a fifth near-infrared light source is configured to emit near-infrared light directed to an Fz site, a sixth near-infrared light source is configured to emit near-infrared light directed to an F4 site, wherein the Fp1 site is the region of interest, the Fpz site is a second region of interest, the Fp2 site is a third region of interest, the F3 site is a fourth region of interest, the Fz site is a fifth region of interest, and the F4 site is a sixth region of interest.

15. The photobiomodulation therapy garment of any one of embodiments 1-14 wherein a sensor is configured to detect one or more parameters indicative of a position and thereafter transmit a position signal to the controller so that the position can be determined on the skin surface, wherein the sensor is positioned between the second near-infrared light source array and the fifth near-infrared light source.

16. The photobiomodulation therapy garment of any one of embodiments 1-15 wherein the sensor is one or both of a heart rate sensor and a temperature sensor.

17. The photobiomodulation therapy garment of any one of embodiments 1-16 wherein each of the near-infrared light source, the second near-infrared light source, the third near-infrared light source, the fourth near-infrared light source, the fifth near-infrared light source, and the sixth near-infrared light source are separated from one another by a light source spacing that is greater than 5 mm, or that is greater than 10 mm, or that is greater than 15 mm, or that is greater than 20 mm, or that is greater than 25 mm, or that is greater than 30 mm.

18. The photobiomodulation therapy garment of any one of embodiments 1-9 wherein the near-infrared light source is a first grouping of near-infrared light sources, the second near-infrared light source is a second grouping of near-infrared light sources, the third near-infrared light source is a third grouping of near-infrared light sources, the fourth near-infrared light source is a fourth grouping of near-infrared light sources, the fifth near-infrared light source is a fifth grouping of near-infrared light sources, and the sixth near-infrared light source is a sixth grouping of near-infrared light sources.

19. The photobiomodulation therapy garment of any one of embodiments 1-18 wherein the grouping of near-infrared light sources is arranged in a first 3×3 array, the second grouping of near-infrared light sources is arranged in a second 3×3 array, the third grouping of near-infrared light sources is arranged in a third 3×3 array, the fourth grouping of near-infrared light sources is arranged in a fourth 3×3 array, the fifth grouping of near-infrared light sources is arranged in a fifth 3×3 array, and the sixth grouping of near-infrared light sources is arranged in a sixth 3×3 array.

20. The photobiomodulation therapy garment of any one of embodiments 1-19 wherein each of the first 3×3 array, the second 3×3 array, the third 3×3 array, the fourth 3×3 array, the fifth 3×3 array, and the sixth 3×3 array are minimally separated from one another by an intergroup light source spacing that is greater than 5 mm, or that is greater than 10 mm, or that is greater than 15 mm, or that is greater than 20 mm, or that is greater than 25 mm, or that is greater than 30 mm.

21. The photobiomodulation therapy garment of any one of embodiments 1-20 wherein each of the first 3×3 array, the second 3×3 array, the third 3×3 array, the fourth 3×3 array, the fifth 3×3 array, and the sixth 3×3 array are separated from one another by an intergroup light source spacing sufficient to prevent substantial light bleed therebetween.

22. The photobiomodulation therapy garment of any one of embodiments 1-21 further comprising one or more stimulators.

23. The photobiomodulation therapy garment of embodiment 22, wherein the one or more stimulators include a component that can generate a magnetic field.

24. A photobiomodulation therapy garment comprising a garment structure configured to be donned by a user atop a skin surface; a first near-infrared light source integrated with the garment structure; a second near-infrared light source integrated with the garment structure and spaced apart from the first near-infrared light source, the first near-infrared light source and the second near-infrared light source configured to emit near-infrared light at a wavelength between 600 nm to 1600 nm and at a predetermined dosimetry, the first near-infrared light source configured to be directed toward a first region of interest on the skin surface and the second near-infrared light source configured to be directed toward a second region of interest on the skin surface when donned during a photobiomodulation treatment; and a controller having a processor and a memory, the controller being in electrical communication with the first near-infrared light source and the second near-infrared light source, and configured with executable instructions for independently controlling the operation of each of the first near-infrared light source and the second near-infrared light source.

25. The photobiomodulation therapy garment of embodiment 24 wherein the executable instructions are configured for controlling one or more of a light source operation time, a light source fluence level, a light source irradiance level, a light source pulsed operation, and a light source continuous operation.

26. The photobiomodulation therapy garment of embodiments 24 or 25 wherein a sensor is integrated with the garment structure and configured to detect one or more parameters indicative of a reference position on the skin surface, such that when the sensor is positioned atop a reference position on the skin surface the first near-infrared light source will be positioned atop the first region of interest of the skin surface and the second near-infrared light source will be positioned atop the second region of interest of the skin surface.

27. The photobiomodulation therapy garment of any one of embodiments 24-26 wherein the sensor is one or both of a heart rate sensor and a temperature sensor.

28. The photobiomodulation therapy garment of any one of embodiments 24-27 wherein the first near-infrared light source is part of a first grouping of near-infrared light sources and the second near-infrared light source is part of a second grouping of near-infrared light sources.

29. The photobiomodulation therapy garment of any one of embodiments 24-28 wherein each of the first grouping of near-infrared light sources and the second grouping of near-infrared light sources are arranged with an intragroup light source spacing of at least 2 mm therebetween, or at least 3 mm therebetween, or at least 4 mm therebetween, or at least 5 mm therebetween, or at least 6 mm therebetween, or at least 7 mm therebetween, or at least 8 mm therebetween, or at least 9 mm therebetween, or at least 10 mm therebetween.

30. The photobiomodulation therapy garment of any one of embodiments 24-29 wherein the first grouping of near-infrared light sources and the second grouping of near-infrared light sources are minimally separated from one another by an intergroup light source spacing that is greater than 5 mm, or that is greater than 10 mm, or that is greater than 15 mm, or that is greater than 20 mm, or that is greater than 25 mm, or that is greater than 30 mm.

31. The photobiomodulation therapy garment of any one of embodiments 24-30 wherein the first grouping of near-infrared light sources is arranged in a first 3×3 array and the second grouping of near-infrared light sources is arranged in a second 3×3 array.

32. The photobiomodulation therapy garment of any one of embodiments 24-31 further comprising a third grouping of near-infrared light sources arranged in a third 3×3 array, a fourth grouping of near-infrared light sources arranged in a fourth 3×3 array, a fifth grouping of near-infrared light sources arranged in a fifth 3×3 array, and a sixth grouping of near-infrared light sources arranged in a sixth 3×3 array.

33. The photobiomodulation therapy garment of any one of embodiments 24-32 wherein a Fp1 site is the first region of interest, a Fpz site is the second region of interest, a Fp2 site is a third region of interest, a F3 site is a fourth region of interest, a Fz site is a fifth region of interest, and a F4 site is a sixth region of interest; and the first 3×3 array is configured to emit near-infrared light directed to the Fp1 site, the second 3×3 array is configured to emit near-infrared light directed to the Fpz site, the third 3×3 array is configured to emit near-infrared light directed to the Fp2 site, the fourth 3×3 array is configured to emit near-infrared light directed to the F3 site, the fifth 3×3 array is configured to emit near-infrared light directed to the Fz site, the sixth 3×3 array is configured to emit near-infrared light directed to the F4 site.

34. The photobiomodulation therapy garment of any one of embodiments 24-33 wherein the first region of interest is one of an Fp1 site, an Fpz site, an Fp2 site, an F3 site, an Fz site, and an F4 site, a posterior cervical site, a carpal site, and an abdominal site.

35. The photobiomodulation therapy garment of any one of embodiments 24-34 wherein the second region of interest is one of an Fp1 site, an Fpz site, an Fp2 site, an F3 site, an Fz site, and an F4 site, a posterior cervical site, a carpal site, and an abdominal site.

36. The photobiomodulation therapy garment of any one of embodiments 24-35 further comprising a third near-infrared light source, a fourth near-infrared light source, a fifth near-infrared light source, and a sixth near-infrared light source.

37. The photobiomodulation therapy garment of any one of embodiments 24-36 wherein a Fp1 site is the first region of interest, a Fpz site is the second region of interest, a Fp2 site is a third region of interest, a F3 site is a fourth region of interest, a Fz site is a fifth region of interest, and a F4 site is a sixth region of interest; and the first near-infrared light source is configured to emit near-infrared light directed to the Fp1 site, the second near-infrared light source is configured to emit near-infrared light directed to the Fpz site, the third near-infrared light source is configured to emit near-infrared light directed to the Fp2 site, the fourth near-infrared light source is configured to emit near-infrared light directed to the F3 site, the fifth near-infrared light source is configured to emit near-infrared light directed to the Fz site, the sixth near-infrared light source is configured to emit near-infrared light directed to the F4 site.

38. The photobiomodulation therapy garment of any one of embodiments 24-37 further comprising one or more stimulators.

39. The photobiomodulation therapy garment of embodiment 38, wherein the one or more stimulators include a component that can generate a magnetic field.

Aspects of the present specification may also be described by the following embodiments:

1. A photobiomodulation therapy garment comprising: a garment configured to be donned by a user atop a skin surface, the garment comprising a first surface and a second surface opposite the first surface, the first surface being configured to face the skin surface once the garment is donned, and a photobiomodulation unit integrated within the garment, the photobiomodulation unit comprising a connection terminal, one or more near-infrared light sources, and one or more sensors, the connection terminal in electronic communication with the one or more near-infrared light sources and one or more sensors, wherein the one or more near-infrared light sources are each configured to emit near-infrared light at a wavelength between 600 nm to 1600 nm and at a predetermined dosimetry, a controller, the controller including a processor and a memory, the controller configured to operationally engage a terminal rail of the connection terminal in an manner that establishes electronic communication between the controller and the connection terminal; wherein the first surface of the garment includes a first portion comprising one or more light openings, with each of the one or more near-infrared light sources being in operational alignment with the one or more light openings to permit proper passage of near-infrared light from the one or more near-infrared light sources therethrough, wherein the first surface of the garment includes a second portion comprising one or more sensor openings with each of the one or more sensors being in operational alignment with the one or more sensor openings to permit proper functionality of the one or more sensors therethrough, and wherein the processor and the memory configured with executable instructions for independently controlling each of the one or more near-infrared light sources and each of each of the one or more sensors.

2. The photobiomodulation therapy garment of embodiment 1, wherein the garment is configured to wrap about or conform to a body part region, with the capability to be moved from one body part region to another body part region on the body.

3. The photobiomodulation therapy garment of embodiment 2, wherein the body part region is a head region, a neck region, a shoulder region, a torso region, a hand region, a wrist region, an arm region, a foot region, or a leg region, or any combination thereof.

4. The photobiomodulation therapy garment of embodiment 2, wherein the garment is a band, a wrap, a scarf, a shawl, a cloak, a robe, or a blanket.

5. The photobiomodulation therapy garment of embodiment 1, wherein the garment is sized and dimensioned to specifically fit a particular body part.

6. The photobiomodulation therapy garment of embodiment 5, wherein the particular body part is a head region, a neck region, a shoulder region, a torso region, a hand region, a wrist region, an arm region, a foot region, or a leg region, or any combination thereof.

7. The photobiomodulation therapy garment of embodiment 4, wherein the garment is a hat, a visor, a shirt, a pants, a sock, a glove, or an undergarment.

8. The photobiomodulation therapy garment of any one of embodiments 1-7, wherein each of the one or more near-infrared light sources is a near-infrared light emitting diode.

9. The photobiomodulation therapy garment of any one of embodiments 1-8, wherein each of the one or more sensors is configured to detect and collect information on one or more parameters of the garment, the photobiomodulation unit and components therein, the controller and components therein, and the user, and thereafter transmit the information to the controller.

10. The photobiomodulation therapy garment of embodiment 9, wherein the one or more parameters includes operational information of the garment, the photobiomodulation unit and components therein, and the controller and components therein, biometric information on the user, or any combination thereof.

11. The photobiomodulation therapy garment of any one of embodiments 1-10, wherein the executable instructions independently control each of the one or more near-infrared light sources.

12. The photobiomodulation therapy garment of embodiment 11, wherein the executable instructions control activation, duration of activation, deactivation, duration of deactivation, a pattern and timing of activation, a pattern and timing of deactivation, a fluence level, an irradiance level, a dosimetry level, a pulsed operation, a continuous operation, an operation time, a cycle duration, or any combination thereof for each of the one or more near-infrared light sources.

13. The photobiomodulation therapy garment of any one of embodiments 1-12, wherein the executable instructions independently control each of the one or more sensors.

14. The photobiomodulation therapy garment of embodiment 13, wherein the executable instructions control collection and analysis of the information of each of the one or more sensors.

15. The photobiomodulation therapy garment of any one of embodiments 1-14, wherein the one or more near-infrared light sources are a plurality of spaced apart near-infrared light sources.

16. The photobiomodulation therapy garment of embodiment 15, wherein the plurality of spaced apart near-infrared light source is between 3 and 6 near-infrared light sources.

17. The photobiomodulation therapy garment of embodiment 15 or 16, wherein the plurality of spaced apart near-infrared light sources is arranged in a single row.

18. The photobiomodulation therapy garment of embodiment 15 or 16, wherein the plurality of spaced apart near-infrared light sources is arranged in a plurality of rows.

19. The photobiomodulation therapy garment of embodiment 18, wherein the plurality of rows is between 2 and 6.

20. The photobiomodulation therapy garment of any one of embodiments 15-19, wherein the plurality of spaced apart near-infrared light sources is arranged in a plurality of columns.

21. The photobiomodulation therapy garment of embodiment 20, wherein the plurality of columns is between 2 and 8.

22. The photobiomodulation therapy garment of any one of embodiments 15-17, 20, or 21, wherein the plurality of near-infrared light sources are arranged in a 1×2 array, a 1×3 array, a 1×4 array, a 1×5 array, a 1×6 array, a 1×7 array, a 1×8 array of row to columns.

23. The photobiomodulation therapy garment of any one of embodiments 15-17, 20, or 21, wherein the plurality of near-infrared light sources comprise three near-infrared light sources arranged in a 1×3 array of row to columns.

24. The photobiomodulation therapy garment of any one of embodiments 17, or 20-23, wherein spacing between each of the plurality of near-infrared light sources contained in the single row is between 0.5 cm to 4 cm and the spacing between each of the plurality of near-infrared light sources contained in each of the plurality of columns is between 0.5 cm to 4 cm.

25. The photobiomodulation therapy garment of any one of embodiments 15, 16, 18-21, wherein the plurality of near-infrared light sources are arranged in a 2×2 array, a 2×3 array, a 2×4 array, a 2×5 array, a 2×6 array, a 2×7 array, a 2×8 array, 3×2 array, a 3×3 array, a 3×4 array, a 3×5 array, a 3×6 array, a 3×7 array, or a 3×8 array of rows to columns.

26. The photobiomodulation therapy garment of any one of embodiments 15, 16, 18-21, wherein the plurality of near-infrared light sources comprise six near-infrared light sources arranged in a 2×3 array of rows to columns.

27. The photobiomodulation therapy garment of any one of embodiments 15, 16, 18-21, wherein the plurality of near-infrared light sources comprise six near-infrared light sources arranged with four near-infrared light sources located in a top row and two near-infrared light sources located in a bottom row.

28. The photobiomodulation therapy garment of any one of embodiments 18-21, or 25-27, wherein spacing between each of the plurality of near-infrared light sources contained in each of the plurality of rows is between 0.5 cm to 4 cm and the spacing between each of the plurality of near-infrared light sources contained in each of the plurality of columns is between 0.5 cm to 4 cm.

29. The photobiomodulation therapy garment of any one of embodiments 15-28, wherein the plurality of near-infrared light sources are arranged in a plurality of spaced apart near-infrared light source groups, each of the plurality of near-infrared light source groups comprising a plurality of near-infrared light sources.

30. The photobiomodulation therapy garment of embodiment 29, wherein the plurality of spaced apart near-infrared light source groups is arranged in a single row.

31. The photobiomodulation therapy garment of embodiment 29, wherein the plurality of spaced apart near-infrared light source groups is arranged in a plurality of rows.

32. The photobiomodulation therapy garment of embodiment 31, wherein the plurality of rows is between 2 and 6.

33. The photobiomodulation therapy garment of any one of embodiments 29-32, wherein the plurality of spaced apart near-infrared light source groups is arranged in a plurality of columns.

34. The photobiomodulation therapy garment of embodiment 33, wherein the plurality of columns is between 2 and 8.

35. The photobiomodulation therapy garment of any one of embodiments 29, 30, 33, or 34, wherein the plurality of near-infrared light source groups are arranged in a 1×2 array, a 1×3 array, a 1×4 array, a 1×5 array, a 1×6 array, a 1×7 array, a 1×8 array of row to columns.

36. The photobiomodulation therapy garment of any one of embodiments 30, or 33-35, wherein spacing between each of the plurality of near-infrared light source groups contained in the single row is between 0.5 cm to 4 cm and the spacing between each of the plurality of near-infrared light source groups contained in each of the plurality of columns is between 0.5 cm to 4 cm.

37. The photobiomodulation therapy garment of any one of embodiments 29, 31-34, wherein the plurality of near-infrared light source groups are arranged in a 2×2 array, a 2×3 array, a 2×4 array, a 2×5 array, a 2×6 array, a 2×7 array, a 2×8 array, 3×2 array, a 3×3 array, a 3×4 array, a 3×5 array, a 3×6 array, a 3×7 array, or a 3×8 array of rows to columns.

38. The photobiomodulation therapy garment of any one of embodiments 31-34, or 37, wherein spacing between each of the plurality of near-infrared light source groups contained in each of the plurality of rows is between 0.5 cm to 4 cm and the spacing between each of the plurality of near-infrared light source groups contained in each of the plurality of columns is between 0.5 cm to 4 cm.

39. The photobiomodulation therapy garment of any one of embodiments 29-38, wherein the plurality of spaced apart near-infrared light sources is arranged in a single row.

40. The photobiomodulation therapy garment of any one of embodiments 29-38, wherein the plurality of spaced apart near-infrared light sources is arranged in a plurality of rows.

41. The photobiomodulation therapy garment of embodiment 40, wherein the plurality of rows is between 2 and 6.

42. The photobiomodulation therapy garment of any one of embodiments 39-41, wherein the plurality of spaced apart near-infrared light sources is arranged in a plurality of columns.

43. The photobiomodulation therapy garment of embodiment 42, wherein the plurality of columns is between 2 and 8.

44. The photobiomodulation therapy garment of any one of embodiments 39, 42, or 43, wherein the plurality of near-infrared light sources are arranged in a 1×2 array, a 1×3 array, a 1×4 array, a 1×5 array, a 1×6 array, a 1×7 array, a 1×8 array of row to columns.

45. The photobiomodulation therapy garment of any one of embodiments 39, or 42-44, wherein spacing between each of the plurality of near-infrared light sources contained in the single row is between 1 mm to 4 mm and the spacing between each of the plurality of near-infrared light sources contained in each of the plurality of columns is between 1 mm to 4 mm.

46. The photobiomodulation therapy garment of any one of embodiments 40-43, wherein the plurality of near-infrared light sources are arranged in a 2×2 array, a 2×3 array, a 2×4 array, a 2×5 array, a 2×6 array, a 2×7 array, a 2×8 array, 3×2 array, a 3×3 array, a 3×4 array, a 3×5 array, a 3×6 array, a 3×7 array, or a 3×8 array of rows to columns.

47. The photobiomodulation therapy garment of any one of embodiments 40-43, wherein the plurality of near-infrared light sources comprise nine near-infrared light sources arranged in a 3×3 array of rows to columns.

48. The photobiomodulation therapy garment of any one of embodiments 40-43, 46, or 47, wherein spacing between each of the plurality of near-infrared light sources contained in each of the plurality of rows is between 1 mm to 4 mm and the spacing between each of the plurality of near-infrared light sources contained in each of the plurality of columns is between 1 mm to 4 mm.

49. The photobiomodulation therapy garment of any one of embodiments 1-48 further comprising one or more stimulators.

50. The photobiomodulation therapy garment of embodiment 49, wherein the one or more stimulators include a component that can generate a magnetic field 51. The photobiomodulation therapy garment of any one of embodiments 1-50, wherein the skin surface comprises a forehead site, a posterior cervical site, a carpal site, an abdominal site, or any combination thereof.

52. The photobiomodulation therapy garment of embodiment 51, wherein the forehead site comprises a dorsolateral prefrontal cortex region, a frontal eye fields region, or both.

53. The photobiomodulation therapy garment of embodiment 51, wherein the forehead site comprises an Fp1 site, an Fpz site, an Fp2 site, an F3 site, an Fz site, an F4 site, or any combination thereof.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to a photobiomodulation therapy garment, or methods and uses disclosed herein.

Example 1

Photobiomodulation Therapy Garment

In one example arrangement of transcranial photobiomodulation therapy garment 20, specifically photobiomodulation therapy headband 22, has six infrared light source intergroups arranged in two rows with three intergroups in each row. The infrared light source intergroups are configured on photobiomodulation therapy headband 22 in a manner where each intergroup at least partially overlays or is substantially centered over sites Fp1 300, Fpz 302, Fp2 304, F3 5306, Fz 308, and F4 310. The estimated total area of skin surface S and tissue beneath exposed to the near-infrared light is about 5.3 cm$^2$ to about 5.7 cm$^2$ and provides a photobiomodulation therapy to dorsolateral prefrontal cortex (dIPFC) and frontal eye fields (FEF). Each infrared light source intergroup has nine LEDs in a 3×3 rectangular array. Each LED has about 55 mW of power, with peak optical output being about 99 mW, and emits infrared light having an average wavelength of 800 nm to about 850 nm and pulse wave of 40 Hz. The average irradiance over the treatment area is about 16 mW/cm$^2$ to about 20 mW/cm$^2$, with areas of maximum irradiance potentially up to about 240 mW/cm$^2$ to about 365 mW/cm$^2$. The average fluence over the treatment area is about 40 J/cm$^2$ to about 45 J/cm$^2$, with areas of maximum fluence potentially up to about 665 J/cm$^2$ to about 998 J/cm$^2$. The total energy incident during the treatment session is about 2.0 kJ to about 2.5 kJ. Controller 200 operates the LEDs continuously (not pulsed) for 10 minutes to 25 minutes.

In an alternative configuration, one or more of the six infrared light sources intergroup of photobiomodulation therapy headband 22 has a combination of both high-powered and low-powered infrared light sources 170. For example, the upper left and upper right infrared light source intergroups can have the center infrared light source 170 of the 3×3 array be a high-powered infrared light source and the remaining infrared light sources 170 being low-powered infrared light sources.

In an alternative configuration, photobiomodulation therapy headband 22 exhibits an average irradiance over the treatment area is about 31 mW/cm$^2$ to about 35 mW/cm$^2$, with areas of maximum irradiance potentially up to about 445 mW/cm$^2$ to about 670 mW/cm$^2$. In addition, the average fluence over the treatment area is about 38 J/cm$^2$ to about 60 J/cm$^2$, with areas of maximum fluence potentially up to about 665 J/cm$^2$ to about 1,005 J/cm$^2$. The total energy incident during the treatment session is about 2.0 kJ to about 5.0 kJ.

Example 2

Photobiomodulation Therapy Garment

In another example arrangement of transcranial photobiomodulation therapy garment 20, specifically photobiomodulation therapy headband 22, has three infrared light source intergroups arranged in one row. The infrared light source intergroups are configured on photobiomodulation therapy headband 22 in a manner where each intergroup at least partially overlays or is substantially centered over sites Fp1 300, Fpz 302, and Fp2 304. The estimated total area of skin surface S and tissue beneath exposed to the near-infrared light is about 2.8 cm$^2$ to about 3.3 cm$^2$ and provides a photobiomodulation therapy to the frontal eye fields (FEF). Each infrared light source intergroup has nine low powered LEDs in a 3×3 rectangular array. Each infrared light source intergroup has nine LEDs in a 3×3 rectangular array. Each LED has about 55 mW of power, with peak optical output being about 99 mW, and emits infrared light having an average wavelength of 800 nm to about 850 nm and pulse wave of 40 Hz (range 0 Hz to 100 Hz). The average irradiance over the treatment area is about 31 mW/cm$^2$ to about 35 mW/cm$^2$, with areas of maximum irradiance potentially up to about 80 mW/cm$^2$ to about 105 mW/cm$^2$. The average fluence over the treatment area is about 58 J/cm$^2$ to about 63 J/cm$^2$, with areas of maximum fluence potentially up to about 145 J/cm$^2$ to about 185 J/cm$^2$. The total energy incident during the treatment session is about 1.2 kJ to about 3.0 kJ. Controller 200 operates the LEDs continuously (not pulsed) for 10 minutes to 40 minutes.

In an alternative configuration, controller 200 operates the LEDs in a pulsed operation at 40 Hz and 50% duty cycle (variable range being 5% to 100%) for 30 minutes to about 40 minutes. Average irradiance, average areas of maximum irradiance, and average fluence are as described above, with peak irradiance being about 66 mW/cm$^2$ to about 67 mW/cm$^2$, peak areas of maximum irradiance potentially up to about 160 mW/cm$^2$ to about 205 mW/cm$^2$, and peak fluence over the treatment area maximum fluence being potentially up to about 145 J/cm$^2$ to about 185 J/cm$^2$.

In an alternative configuration, controller 200 operates the LEDs in a pulsed operation at 40 Hz and 33% duty cycle (variable range being 5% to 100%) for 30 minutes to about 40 minutes. Average irradiance, average areas of maximum irradiance, and average fluence are as described above, with peak irradiance being about 99 mW/cm$^2$ to about 101 mW/cm$^2$, peak areas of maximum irradiance potentially up to about 240 mW/cm$^2$ to about 310 mW/cm$^2$, and peak fluence over the treatment area maximum fluence being potentially up to about 145 J/cm$^2$ to about 185 J/cm$^2$. The total energy incident during the treatment session is approximately 2.3 kJ.

In an alternative configuration, controller 200 operates the LEDs in a pulsed operation at 10 Hz or 40 Hz and 20% duty cycle (variable range being 5% to 100%) for 30 minutes to about 40minutes. Average irradiance, average areas of maximum irradiance, and average fluence are as described above, with peak irradiance being about 165 mW/cm$^2$ to about 167 mW/cm$^2$, peak areas of maximum irradiance potentially up to about 405 mW/cm$^2$ to about 510 mW/cm$^2$, and peak fluence over the treatment area maximum fluence being potentially up to about 145 J/cm$^2$ to about 185 J/cm$^2$. The total energy incident during the treatment session is approximately 2.3 kJ.

Example 3

Photobiomodulation Therapy Garment

In another example arrangement of transcranial photobiomodulation therapy garment 20, specifically photobiomodulation therapy headband 22, has six infrared light source intergroups arranged in two rows with four intergroups in the top row and two intergroups in the row and organized as two inverse triangles. The infrared light source intergroups are configured on photobiomodulation therapy headband 22 in a manner where one inverse triangle arrangement at least partially overlays or is substantially centered over sites F3 306, Fz 308, and Fp1 300 and the other inverse triangle arrangement at least partially overlays or is substantially centered over sites Fz 308, F4 310, and Fp2 304. The estimated total area of skin surface S and tissue beneath exposed to the near-infrared light is about 7.5 cm$^2$ to about 9 cm$^2$ (each inverse triangle arrangement covering about 3.75 cm$^2$ to about 4.5 cm$^2$) and provides a photobiomodulation therapy to the dorsolateral prefrontal cortex (dIPFC). Each infrared light source intergroup has one high powered LED. Each LED has 500 mW of power, with peak optical output being 500 mW to 1,000 mW, and emits infrared light having an average wavelength of 800 nm to about 850 nm and pulse wave of between 10 Hz to about 40 Hz (range of 0 Hz to 5,000 Hz). The average irradiance over the treatment area is about 50 mW/cm$^2$ to about 300 mW/cm$^2$, with areas of maximum irradiance potentially up to about 500 mW/cm$^2$ to about 1,000 mW/cm$^2$. The average fluence over the treatment area is about 40 J/cm$^2$ to about 120 J/cm$^2$, with areas of maximum fluence potentially up to about 450 J/cm$^2$ to about 1,025 J/cm$^2$. The total energy incident during the treatment session is about 0.4 kJ to about 2.1 kJ. Controller 200 operates the LEDs in a pulsed operation at between about 10 Hz and about 40 Hz and 20% duty cycle (variable range being 5% to 100%) for 10 minutes to about 40 minutes.

In an alternative configuration, each LED has 500 mW of power and emits infrared light having an average wavelength of 960 nm to about 1,100 nm and pulse wave of between 0 Hz to about 100 Hz and potentially up to 5,000 Hz.

Example 4

Photobiomodulation Therapy Garment

In another example arrangement of transcranial photobiomodulation therapy garment 20, specifically photobiomodulation therapy headband 22, has five infrared light source intergroups arranged in two rows with three intergroups in the top row and two intergroups in the bottom row and organized in a manner where one of each intergroup is located below one of the outside intergroups from the top row. The infrared light source intergroups are configured on photobiomodulation therapy headband 22 in a manner where infrared light source intergroups in the top row at least partially overlays or is substantially centered over sites F3 306, Fz 308, and F4 310, one of the intergroups in the bottom row at least partially overlays or is substantially centered over site Fp1 300 and the other intergroups in the bottom row at least partially overlays or is substantially centered over site Fp2 304. The estimated total area of skin surface S and tissue beneath exposed to the near-infrared light is about 7.5 cm$^2$ to about 8 cm$^2$ and provides a photobiomodulation therapy to the dorsolateral prefrontal cortex (dIPFC) and the frontal eye fields (FEF). Each infrared light source intergroup has one high powered LED. Each LED has 500 mW of power, with peak optical output being 500 mW to 1,000 mW, and emits infrared light having an average wavelength of 800 nm to about 850 nm and pulse wave of between 10 Hz to about 40 Hz (having an adjustable range of 0 Hz to 5,000 Hz). The average irradiance over the treatment area is about 50 mW/cm$^2$ to about 300 mW/cm$^2$, with areas of maximum irradiance potentially up to about 500 mW/cm$^2$ to about 1,000 mW/cm$^2$. The average fluence over the treatment area is about 40 J/cm$^2$ to about 120 J/cm$^2$, with areas of maximum fluence potentially up to about 450 J/cm$^2$ to about 1,025 J/cm$^2$. The total energy incident during the treatment session is about 0.4 kJ to about 2.1 kJ. Controller 200 operates the LEDs in a pulsed operation at between about 10 Hz and about 40 Hz and 20% duty cycle (variable range being 5% to 100%) for 10 minutes to about 40 minutes.

In an alternative configuration, each LED has 500 mW of power and emits infrared light having an average wavelength of 960 nm to about 1,100 nm and pulse wave of between 0 Hz to about 100 Hz and potentially up to 5,000 Hz.

Example 5

Photobiomodulation Therapy Garment

In another example arrangement of transcranial photobiomodulation therapy garment 20, specifically photobiomodulation therapy headband 22, has three infrared light source intergroups arranged in one row. The infrared light source intergroups are configured on photobiomodulation therapy headband 22 in a manner where each intergroup at least partially overlays or is substantially centered over sites F3 306, Fz 308 and F4 310. The estimated total area of skin surface S and tissue beneath exposed to the near-infrared light is about 2.8 cm² to about 3.3 cm² and provides a photobiomodulation therapy to the dorsolateral prefrontal cortex (dlPFC). Each infrared light source intergroup has one high powered LED. Each LED has 500 mW of power, with peak optical output being 500 mW to 1,000 mW, and emits infrared light having an average wavelength of 800 nm to about 850 nm and pulse wave of between 10 Hz to about 40 Hz. The average irradiance over the treatment area is about 50 mW/cm² to about 300 mW/cm², with areas of maximum irradiance potentially up to about 500 mW/cm² to about 1,000 mW/cm². The average fluence over the treatment area is about 6 J/cm² to about 12 J/cm², with areas of maximum fluence potentially up to about 450 J/cm² to about 1,025 J/cm². The total energy incident during the treatment session is about 0.15 kJ to about 1.8 kJ. Controller 200 operates the LEDs in a pulsed operation at between about 10 Hz and about 40 Hz and 20% duty cycle (variable range being 5% to 100%) for 10 minutes to about 40 minutes.

In an alternative configuration, each LED has 500 mW of power and emits infrared light having an average wavelength of 860 nm to about 1,100 nm and pulse wave of between 0 Hz to about 100 Hz and potentially up to 5,000 Hz.

Example 6 tPBM Treatment Increases Functional Conductivity of Neurons

A research study was conducted to assess the neuronal conductivity effects of a transcranial photobiomodulation (tPBM) treatment using a photobiomodulation therapy garment disclosed herein. Each participant underwent an EEG analysis for 8 minutes before a tPBM treatment in order to establish a baseline. Each participant was then administered tPBM treatments using a photobiomodulation therapy garment disclosed herein. Each tPBM treatment was bilateral and applied to the frontal areas with two application sites on the left side, two on the right side and two on the midline [left, right and center forehead on the frontal EEG sites on F3, Fpl, F4, Fp2 and Fz, Fpz]. Once accurate placement is ensured, a tPBM treatment was initiated by a button press on a specific phone application to activate the probes delivering the LED light. The duration of irradiation was 40 min per treatment. The tPBM treatment followed these specifications: the energy was administered with a radiation wavelength of 850 nm, the irradiance (IR) was 18 mW/cm²; the fluence was up to 43 Joules/cm²; the energy delivered per session was up to 2.4 kJ; and each treatment window area was 55 cm². After completion of the tPBM treatment, each participant underwent a second EEG analysis for 8 minutes.

The results of this research study showed that participants exhibiting increased functional connectivity of their neurons (as measured with EEG activity) compared to sham. For example, FIGS. 17A-C shows the results of five (5) participants. Scans of the EEG analysis conducted after the tPPB treatment exhibit focused points of light (FIG. 17B) as compared to scans taken before the tPBM treatment (FIG. 17A). These differences are further underscored by FIG. 17C, which illustrates the focused light of the before and after scans. These findings is indicative of improved connections between neurons. Increased functional connectivity allow neurons to transmit information faster and more accurately. The results were reproducible and not evident with the sham.

Example 7 tPBM Treatment Increases Brain Activity

A research study was conducted to assess brain activity effects of a transcranial photobiomodulation (tPBM) treatment using a photobiomodulation therapy garment disclosed herein. Each participant underwent an EEG analysis for 8 minutes before a tPBM treatment in order to establish a baseline. Each participant was then administered tPBM treatments using a photobiomodulation therapy garment disclosed herein. Each tPBM treatment was bilateral and applied to the frontal areas with two application sites on the left side, two on the right side and two on the midline [left, right and center forehead on the frontal EEG sites on F3, Fpl, F4, Fp2 and Fz, Fpz]. Once accurate placement is ensured, a tPBM treatment was initiated by a button press on a specific phone application to activate the probes delivering the LED light. The duration of irradiation was 40 min per treatment. The tPBM treatment followed these specifications: the energy was administered with a radiation wavelength of 850 nm, the irradiance (IR) was 18 mW/cm²; the fluence was up to 43 Joules/cm²; the energy delivered per session was up to 2.4 kJ; and each treatment window area was 55 cm². After completion of the tPBM treatment, each participant underwent a second EEG analysis for 8 minutes.

The results of this research study showed that participants exhibited increased brain gamma oscillation increased during a 40 Hz pulse wave therapy compared to sham. For example, FIGS. 18A-18B shows a representative result from one participant. As shown in FIG. 18A by the shaded block, there was a significant increase of over 35% in brain gamma oscillations at a frequency of 40 Hz. In addition, as shown in FIG. 18B, there is a significant peak of gamma power between about 250 seconds to about about 350 seconds, at which point gamma power levels decline but are maintained at a higher level as compared to baseline gamma power levels. These findings are indicative of brain gamma wave stimulation which underlie many cognitive operations including perception. Increased brain gamma wave stimulation promotes brain activity to transmit information faster and more accurately. The results were reproducible and not evident with the sham.

Example 8 tPBM Treatment for Depression in Adults

An 8-week open-label pilot clinical study was conducted to assess the safety, and efficacy of a tPBM treatment using a photobiomodulation therapy garment disclosed herein in adults with active depressive symptoms. The study enrolled 19 participants clinically diagnosed with moderate to severe depressive symptoms according to the Beck's Depressive Inventory (BDI, baseline score of 25).

Participants were administered tPBM treatments twice daily at home for 8 weeks using a photobiomodulation therapy garment disclosed herein. Each tPBM treatment was bilateral and applied to the frontal areas with two application sites on the left side, two on the right side and two on the midline [left, right and center forehead on the frontal EEG sites on F3, Fpl, F4, Fp2 and Fz, Fpz]. Once accurate placement is ensured, a tPBM treatment was initiated by a button press on a specific phone application to activate the probes delivering the LED light. The duration of irradiation was 40 min per treatment. The tPBM treatment will follow these specifications: the energy will be administered with a radiation wavelength of 850 nm, the irradiance (IR) will be 18 mW/cm$^2$; the fluence will be up to 43 Joules/cm$^2$; the energy delivered per session will be up to 2.4 kJ; and each treatment window area will be 55 cm$^2$.

At the end of the 8-week clinical study of tPBM treatment of depression using a photobiomodulation therapy garment disclosed herein, investigators detected a significant reduction in depressive symptoms among participants. For example, participants experienced a 43% decrease in depressive symptoms at week 8 as assessed by the Beck's Depression Inventory. The finding was a statistically significant change from baseline (significance p=0.001). Interestingly, the improvement was maintained for at least 4 weeks after stopping the tPBM treatment. In fact, at week 12 the investigators still detected an average decrease of 48% in depressive symptoms, compared to baseline, as assessed by the Beck's Depression Inventory. The finding was also a significant change from baseline (significance p<0.0001). Subsequent analyses revealed that the improvements in depression were at least partially explained by improvement in sleep quality.

Example 9 tPBM Treatment for Pediatric Depression

An 8-week open-label pilot clinical study will be conducted to assess the safety, and efficacy of a tPBM treatment using a photobiomodulation therapy garment disclosed herein in children with active depressive symptoms as assessed through the Child Behavior Checklist (CBCL). The study will enroll 20-30 participants, ages 6 to 17 years, who currently experience a CBCL T score of 60 or higher on the Anxious/Depressed scale. Each participant will be clinically assessed by completing a series of clinical intake questionnaires and scales, including 1) CBCL, a parent-report questionnaire that evaluates maladaptive behavioral and emotional problems, both internalizing and externalizing, in children ages 6-18; 2) the Pediatric Quality Of Life Enjoyment and Satisfaction Questionnaire (PQ-LES-Q), a 15 question parent-report form designed to help assess the degree of enjoyment and satisfaction the child is experiencing during the past week; 3) the Behavior Rating Inventory of Executive Function-Parent Report (BRIEF-P), a 78-item rating scale to assess level of executive function deficits; and 4) the Social Responsiveness Scale (SRS), a 65-item rating scale completed by the parent used to measure social deficits as they occur in natural settings.

Participants will be administered daily tPBM treatments for 8 weeks. tPBM treatment will use a photobiomodulation therapy garment disclosed herein will be bilateral and applied to the frontal areas with two application sites on the left side, two on the right side and two on the midline [left, right and center forehead on the frontal EEG sites on F3, Fp1, F4, Fp2 and Fz, Fpz]. Once accurate placement is ensured, a tPBM treatment will be initiated by a button press on a specific phone application to activate the probes delivering the LED light. The duration of irradiation will start at 10 min per treatment for the first week (days 1-7), increase to 20 min per treatment during the second week of treatment (days 7-14) and to 30 min per treatment at week 3 (days 14-21) of treatment. If side-effects prevent increase (or if treatment response already occurred), a lower dose will be kept in order to ensure good tolerability and treatment adherence. At day 21, the clinician will recommend 40 min daily treatment if no improvement in the context of good tolerability. The tPBM treatment will follow these specifications: the energy will be administered with a radiation wavelength of 850 nm, the irradiance (IR) will be 18 mW/cm$^2$ ; the fluence will be up to 43 Joules/cm$^2$; the energy delivered per session will be up to 2.4 kJ; and each treatment window area will be 55 cm$^2$.

Subjects will be evaluated at weekly intervals for the first four weeks, and biweekly thereafter. At each visit, measures of safety and efficacy will be obtained using assessments of psychiatric symptoms and functioning and measures of adverse effects. At the midpoint (end of week 4) and final study visits (week 8 or Endpoint), additional clinician-and subject-rated assessments will be completed. Response to treatment will be assessed by the following assessment measures 1) a Clinician completed Depression Specific Clinical Global Impression (CGI-Depression), including Clinical Global Severity (CGI-S), Clinical Global Improvement (CGI-I), and the CGI-Efficacy Index (CGI-EI) Scale, will be completed by the physician at every visit; 2) an Affective Reactivity Index-Parent Report (ARI-P), a concise, 7 question parent-report form assessing irritability and temper, will be completed by the parent at week 0 (baseline), week 4 and week 8; 3) a Childhood Anxiety Sensitivity Index (CASI-Anx), a 38-item scale that assesses symptoms of anxiety, will be completed by the parent at week 0 (baseline), week 4 and week 8; and 4) a Children's Depression Inventory (CDI), a 27-item scale that assesses symptoms of depression, will be completed by the parent at week 0 (baseline), week 4 and week 8.

The results are expected to show that a tPBM treatment will be safe and effective in reducing symptoms of pediatric depression.

Example 10 tPBM Treatment of Autistic Traits in Children with Attention Deficit Hyperactivity Disorder (ADHD)

A 10-week open-label pilot clinical study will be conducted to assess the tolerability, safety, and efficacy of a tPBM treatment using a photobiomodulation therapy garment disclosed herein in children diagnosed with ADHD who also present with at least moderate level of autistic traits. The study will enroll 90-100 participants, ages 9 to 17 years, who fulfill the DSM-5 diagnostic criteria for ADHD and present with moderately severe autistic spectrum disorder symptoms as established by a Social Responsiveness Scale, $2^{nd}$ Edition (SRS-2) raw score of 75 or higher or a Clinical Global Impressions—Autistic Traits (CGI-AT) severity score of 4 or higher. Each participant will be clinically assessed by a board-certified clinician for ADHD and autism traits and all participant's parent/guardian will be administered an assessment battery including a brief demographic interview and the Autism Trait Specific Clinical Global Impression (CGI-AT), including Clinical Global Severity (CGI-S), Clinical Global Improvement (CGI-I), and the CGI-Efficacy Index (CGI-EI) Scale, the Behavior Rating Inventory of Executive Function-Parent Version (BRIEF-P), the Child Behavior Checklist (CBCL), the Clinician-Rated Treatment Emergent Adverse Events Log (CTAE), the Global Assessment of Functioning Scale (GAF), the Massachusetts General Hospital Social-Emotional Competence Scale (MGH-SECS) questionnaires including MGH-SECS-Informant Rated (MGH-SECS-I) and MGH-SECS Clinician Rated (MGH-SECS-C), the MGH Autism Spectrum Disorder DSM-5 Diagnostic Symptom Checklist (MGH-ASD-SCL), and the SRR-2 questionnaires.

Participants will be administered daily tPBM treatments for 8 weeks and a post-study follow-up will occur at week 10. tPBM treatment will use a photobiomodulation therapy garment disclosed herein will be bilateral and applied to the frontal areas with two application sites on the left side, two on the right side and two on the midline [left, right and center forehead on the frontal EEG sites on F3, Fp1, F4, Fp2 and Fz, Fpz]. Once accurate placement is ensured, a tPBM treatment will be initiated by a button press on a specific phone application to activate the probes delivering the LED light. The duration of irradiation will start at 10 min per treatment for the first week (days 1-7), increase to 20 min per treatment during the second week of treatment (days 7-14) and to 30 min per treatment at week 3 (days 14-21) of treatment. If side-effects prevent increase (or if treatment response already occurred), a lower dose will be kept in order to ensure good tolerability and treatment adherence. At day 21, the clinician will recommend 40 min daily treatment if no improvement in the context of good tolerability. The tPBM treatment will follow these specifications: the energy will be administered with a radiation wavelength of 850 nm, the irradiance (IR) will be 18 mW/cm$^2$; the fluence will be up to 43 Joules/cm$^2$; the energy delivered per session will be up to 2.4 kJ; and each treatment window area will be 55 cm$^2$.

Subjects will be evaluated at weekly intervals for the first four weeks, and biweekly thereafter. At each visit, measures of safety and efficacy will be obtained using assessments of psychiatric symptoms and functioning and measures of adverse effects. At the midpoint (end of week 4) and final study visits (week 8 or Endpoint), additional clinician-and subject-rated assessments will be completed. Response to treatment will be assessed by the following assessment measures 1) an CGI-AT, including CGI-S, CGI-I, and CGI-EI Scale, will be completed by the physician at weeks 0 (baseline), 1, 2, 3, 4, 6, and 8; 2) a GAF and CTAE will be completed by the physician at weeks 0 (baseline), 1, 2, 3, 4, 6, and 8; 3) an Attention Deficit Hyperactivity Disorder Symptom Checklist (ADHD-SC) will be completed by the physician at weeks 0 (baseline), 4, and 8; 4) a tPBM Self-Report Questionnaire (TSRQ) will be completed by the parent/guardian at weeks 1, 2, 3, 4, 6, and 8; 5) a SRS-2 and CBCL will be completed by the physician at weeks 4 and 8; 5) a BRIEF-P and MGH-SECS-I will be completed by the parent/guardian at week 8; and 6) a MGH-SECS-C will be completed by the physician at week 8. At week 10, each participant will be assessed by CGI-AT, including CGI-S, CGI-I, and CGI-EI Scale, GAF, CTAE, SRS-1, ADHD-SC, and TSRQ, The results are expected to show that a tPBM treatment will be safe and effective in reducing autistic traits in children diagnosed with ADHD.

In closing, foregoing descriptions of embodiments of the present invention have been presented for the purposes of illustration and description. It is to be understood that, although aspects of the present invention are highlighted by referring to specific embodiments, one skilled in the art will readily appreciate that these described embodiments are only illustrative of the principles comprising the present invention. As such, the specific embodiments are not intended to be exhaustive or to limit the invention to the precise forms disclosed. Therefore, it should be understood that embodiments of the disclosed subject matter are in no way limited to a particular element, compound, composition, component, article, apparatus, methodology, use, protocol, step, and/or limitation described herein, unless expressly stated as such.

In addition, groupings of alternative embodiments, elements, steps and/or limitations of the present invention are not to be construed as limitations. Each such grouping may be referred to and claimed individually or in any combination with other groupings disclosed herein. It is anticipated that one or more alternative embodiments, elements, steps and/or limitations of a grouping may be included in, or deleted from, the grouping for reasons of convenience and/or patentability. When any such inclusion or deletion occurs, the specification is deemed to contain the grouping as modified, thus fulfilling the written description of all Markush groups used in the appended claims.

Furthermore, those of ordinary skill in the art will recognize that certain changes, modifications, permutations, alterations, additions, subtractions and sub-combinations thereof can be made in accordance with the teachings herein without departing from the spirit of the present invention. Furthermore, it is intended that the following appended claims and claims hereafter introduced are interpreted to include all such changes, modifications, permutations, alterations, additions, subtractions and sub-combinations as are within their true spirit and scope. Accordingly, the scope of the present invention is not to be limited to that precisely as shown and described by this specification.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

The words, language, and terminology used in this specification is for the purpose of describing particular embodiments, elements, steps and/or limitations only and is not intended to limit the scope of the present invention, which is defined solely by the claims. In addition, such words, language, and terminology are to be understood not only in the sense of their commonly defined meanings, but to include by special definition in this specification structure, material or acts beyond the scope of the commonly defined meanings. Thus, if an element, step or limitation can be understood in the context of this specification as including more than one meaning, then its use in a claim must be understood as being generic to all possible meanings supported by the specification and by the word itself.

The definitions and meanings of the elements, steps or limitations recited in a claim set forth below are, therefore, defined in this specification to include not only the combination of elements, steps or limitations which are literally set forth, but all equivalent structure, material or acts for performing substantially the same function in substantially the same way to obtain substantially the same result. In this sense it is therefore contemplated that an equivalent substitution of two or more elements, steps or limitations may be made for any one of the elements, steps or limitations in a claim set forth below or that a single element, step or limitation may be substituted for two or more elements, steps or limitations in such a claim. Although elements, steps or limitations may be described above as acting in certain combinations and even initially claimed as such, it is to be expressly understood that one or more elements, steps or limitations from a claimed combination can in some cases be excised from the combination and that the claimed combination may be directed to a sub-combination or variation of a sub-combination. As such, notwithstanding the fact that the elements, steps and/or limitations of a claim are set forth below in a certain combination, it must be expressly understood that the invention includes other combinations of fewer, more or different elements, steps and/or limitations, which are disclosed in above even when not initially claimed in such combinations. Furthermore, insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements. Accordingly, the claims are thus to be understood to include what is specifically illustrated and described above, what is conceptually equivalent, what can be obviously substituted and also what essentially incorporates the essential idea of the invention.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as, e.g., "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising", variations thereof such as, e.g., "comprise" and "comprises", and equivalent open-ended transitional phrases thereof like "including," "containing" and "having", encompass all the expressly recited elements, limitations, steps, integers, and/or features alone or in combination with unrecited subject matter; the named elements, limitations, steps, integers, and/or features are essential, but other unnamed elements, limitations, steps, integers, and/or features may be added and still form a construct within the scope of the claim. Specific embodiments disclosed herein may be further limited in the claims using the closed-ended transitional phrases "consisting of" or "consisting essentially of" (or variations thereof such as, e.g., "consist of", "consists of", "consist essentially of", and "consists essentially of") in lieu of or as an amendment for "comprising." When used in the claims, whether as filed or added per amendment, the closed-ended transitional phrase "consisting of" excludes any element, limitation, step, integer, or feature not expressly recited in the claims. The closed-ended transitional phrase "consisting essentially of" limits the scope of a claim to the expressly recited elements, limitations, steps, integers, and/or features and any other elements, limitations, steps, integers, and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps, integers, and/or features specifically recited in the claim, whereas the meaning of the closed-ended transitional phrase "consisting essentially of" is being defined as only including those elements, limitations, steps, integers, and/or features specifically recited in the claim and those elements, limitations, steps, integers, and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such, the embodiments described herein or so claimed with the phrase "comprising" expressly and unambiguously provide description, enablement, and support for the phrases "consisting essentially of" and "consisting of."

Lastly, all patents, patent publications, and other references cited and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard is or should be construed as an admission that the inventors are not entitled to antedate such disclosure by virtue of prior invention or for any other reason. All statements as to the date or representation as to the contents of these documents are based on the information available to the applicant and do not constitute any admission as to the correctness of the dates or contents of these documents.

The invention claimed is:

1. A photobiomodulation therapy garment headband comprising:
   headband configured to be donned by a user atop a skin surface, the headband comprising a first surface and a second surface opposite the first surface, the first surface being configured to face the skin surface once the headband is donned, and
   a photobiomodulation unit integrated within the headband, the photobiomodulation unit comprising a connection terminal, one or more near-infrared light sources, and one or more sensors, the connection terminal in electronic communication with the one or more near-infrared light sources and one or more sensors, wherein the one or more near-infrared light sources are each configured to emit near-infrared light at a wavelength between 800 nm to 1100 nm and at a predetermined dosimetry and wherein the one or more near-infrared light sources are configured to generate an irradiance or flux density of at least 25 mW/cm$^2$ to at most 400 mW/cm$^2$,
   a controller, the controller including a processor and a memory, the controller configured to operationally engage a terminal rail of the connection terminal in a manner that establishes electronic communication between the controller and the connection terminal;
   wherein the first surface of the headband includes a first portion comprising one or more light openings, with each of the one or more near-infrared light sources being in operational alignment with the one or more light openings to permit proper passage of near-infrared light from the one or more near-infrared light sources therethrough,
   wherein the first surface of the headband includes a second portion comprising one or more sensor openings with each of the one or more sensors being in operational alignment with the one or more sensor openings to permit proper functionality of the one or more sensors therethrough, and
   wherein the processor and the memory are configured with executable instructions for independently controlling each of the one or more near-infrared light sources and each of the one or more sensors.

2. The photobiomodulation therapy headband of claim 1, wherein the irradiance or flux density is at least 50 mW/cm$^2$.

3. The photobiomodulation therapy garment headband of claim 1, wherein the irradiance or flux density is at most 300 mW/cm$^2$.

4. The photobiomodulation therapy headband of claim 1, wherein each of the one or more near-infrared light sources is a near-infrared light emitting diode.

5. The photobiomodulation therapy headband of claim 1, wherein each of the one or more sensors is configured to detect and collect information on one or more parameters of the headband, the photobiomodulation unit and components therein, the controller and components therein, and the user, and thereafter transmit the information to the controller.

6. The photobiomodulation therapy headband of claim 5, wherein the one or more parameters includes operational information of the headband, the photobiomodulation unit and components therein, and the controller and components therein, biometric information on the user, or any combination thereof.

7. The photobiomodulation therapy headband of claim 1, wherein the executable instructions independently control each of the one or more near-infrared light sources.

8. The photobiomodulation therapy headband of claim 7, wherein the executable instructions control activation, duration of activation, deactivation, duration of deactivation, a pattern and timing of activation, a pattern and timing of deactivation, a fluence level, an irradiance level, a dosimetry level, a pulsed operation, a continuous operation, an operation time, a cycle duration, or any combination thereof for each of the one or more near-infrared light sources.

9. The photobiomodulation therapy headband of claim 1, wherein the executable instructions independently control each of the one or more sensors.

10. The photobiomodulation therapy headband of claim 9, wherein the executable instructions control collection and analysis of information obtained from each of the one or more sensors.

11. The photobiomodulation therapy headband of claim 1, wherein the one or more near-infrared light sources are a plurality of spaced apart near-infrared light sources.

12. The photobiomodulation therapy headband of claim 11, wherein the plurality of near-infrared light sources are arranged in a plurality of spaced apart near-infrared light source groups, each of the plurality of near-infrared light source groups comprising a subset of the one or more near-infrared light sources.

13. The photobiomodulation therapy headband of claim 1 further comprising one or more stimulators.

14. The photobiomodulation therapy headband of claim 13, wherein the one or more stimulators include a component that can generate a magnetic field.

15. The photobiomodulation therapy headband of claim 1, wherein the processor and the memory are configured with executable instructions for dynamically controlling each of the one or more near-infrared light sources and each of the one or more sensors.

16. The photobiomodulation therapy headband of claim 1, wherein the one or more near-infrared light sources are configured to generate a radiant flux or power of at least 900 mW.

17. The photobiomodulation therapy headband of claim 1, wherein the one or more near-infrared light sources are configured to generate a radiant exposure or fluence of at least 20 J/cm² to at most 200 J/cm².

18. The photobiomodulation therapy headband of claim 17, wherein the radiant exposure or fluence generated is at least 30 J/cm².

19. The photobiomodulation therapy headband of claim 1, wherein the irradiance or flux density generated is at least 50 mW/cm² to at most 300 mW/cm².

20. The photobiomodulation therapy headband of claim 1, wherein the one or more near-infrared light sources are configured to generate a radiant flux or power of at least 900 mW, a radiant exposure or fluence in a range of at least 20 J/cm² to at most 200 J/cm², and the irradiance or flux density generated is at least 50 mW/cm² to at most 300 mW/cm².

* * * * *